United States Patent
Pastorin et al.

(10) Patent No.: US 11,129,782 B2
(45) Date of Patent: Sep. 28, 2021

(54) DERIVATIVES OF PPD USEFUL FOR COLORING HAIR AND SKIN

(71) Applicants: National University of Singapore, Singapore (SG); Agency for Science, Technology and Research, Singapore (SG); National University Hospital (Singapore) Pte Ltd, Singapore (SG)

(72) Inventors: Giorgia Pastorin, Singapore (SG); Paul Bigliardi, Minneapolis, MN (US); Suresh Valiyaveettil, Singapore (SG); Gopalakrishnan Venkatesan, Singapore (SG); Arup Sinha, Singapore (SG); Yuri Herbert Dancik, Singapore (SG); Mei Bigliardi-Qi, Minneapolis, MN (US)

(73) Assignees: National University of Singapore, Singapore (SG); Agency for Science, Technology and Research, Singapore (SG); National University Hospital (Singapore) Pte Ltd, Singapore (SG)

( * ) Notice: Subject to any disclaimer, the term of this patent is extended or adjusted under 35 U.S.C. 154(b) by 0 days.

(21) Appl. No.: 16/875,189

(22) Filed: May 15, 2020

(65) Prior Publication Data

US 2020/0390670 A1  Dec. 17, 2020

Related U.S. Application Data

(63) Continuation of application No. PCT/SG2018/050571, filed on Nov. 15, 2018.

(30) Foreign Application Priority Data

Nov. 15, 2017 (SG) .......................... 10201709422Q

(51) Int. Cl.
*A61Q 5/10* (2006.01)
*A61K 8/41* (2006.01)
*A61Q 5/06* (2006.01)

(52) U.S. Cl.
CPC .............. *A61K 8/418* (2013.01); *A61K 8/411* (2013.01); *A61Q 5/065* (2013.01); *A61Q 5/10* (2013.01);

(Continued)

(58) Field of Classification Search
CPC .......... A61Q 5/10; A61Q 5/065; A61K 8/411; A61K 2800/4324; A61K 8/418; A61K 2800/10

(Continued)

(56) References Cited

U.S. PATENT DOCUMENTS 3,549,303 A   12/1970  L'Oreal
4,381,920 A    5/1983  Garlen (Continued)

FOREIGN PATENT DOCUMENTS

AU   2005284472 B2   7/2011
CA      2576189 A1   6/2007

(Continued)

OTHER PUBLICATIONS

STIC Search Report dated Feb. 12, 2021.*

(Continued)

*Primary Examiner* — Eisa B Elhilo
(74) *Attorney, Agent, or Firm* — Osha Bergman Watanabe & Burton LLP

(57) ABSTRACT

The is provided a compound of formula I or II or physiologically acceptable salts or solvates, or oxidised derivatives thereof:

(Continued)

US 11,129,782 B2

Page 2

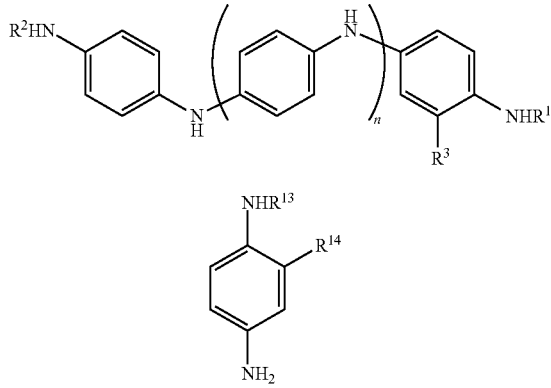

where $R^1$ to $R^3$, $R^{13}$ and $R^{14}$ are as defined herein. Also disclosed herein are methods of dyeing hair or (temporarily) tattooing the skin using the compounds of formula I or II (or physiologically acceptable salts or solvates, or oxidised derivatives thereof) in a suitable composition.

21 Claims, 15 Drawing Sheets

Specification includes a Sequence Listing.

(52) U.S. Cl.
CPC .. *A61K 2800/10* (2013.01); *A61K 2800/4324* (2013.01)

(58) Field of Classification Search
USPC ..................................... 8/405, 410
See application file for complete search history.

(56) References Cited

U.S. PATENT DOCUMENTS

| | | | |
|---|---|---|---|
| 5,928,385 | A | 7/1999 | Cotteret et al. |
| 6,554,870 | B1 | 4/2003 | Cotteret et al. |
| 6,558,433 | B2 | 5/2003 | Goettel et al. |
| 7,090,703 | B2 | 8/2006 | Sabelle et al. |
| 7,132,534 | B2 | 11/2006 | Sabelle et al. |
| 7,166,711 | B2 | 1/2007 | Eliu et al. |
| 7,384,432 | B2 | 6/2008 | Sabelle et al. |
| 2001/0002254 | A1 | 5/2001 | Duffer et al. |
| 2003/0159221 | A1 | 8/2003 | Lang |
| 2004/0064902 | A1 | 4/2004 | Sabelle et al. |
| 2004/0187231 | A1 | 9/2004 | Eliu et al. |
| 2004/0194227 | A9 | 10/2004 | Sabelle et al. |
| 2006/0005320 | A1 | 1/2006 | Sabelle et al. |
| 2007/0186357 | A1 | 8/2007 | Chalmers et al. |
| 2010/0275388 | A1* | 11/2010 | Audousset ............ A61Q 5/10 8/409 |
| 2015/0257994 | A1 | 9/2015 | Charrier et al. |
| 2017/0165166 | A1 | 6/2017 | Gebert-Schwarzwaelder et al. |
| 2017/0258695 | A1 | 9/2017 | Consoli et al. |

FOREIGN PATENT DOCUMENTS

| | | |
|---|---|---|
| CN | 104098770 A | 10/2014 |
| EP | 0891765 B1 | 6/2004 |
| FR | 1164366 A | 10/1958 |
| FR | 2866874 A1 | 9/2005 |
| FR | 3045603 A1 | 6/2017 |
| GB | 2018239 A | 10/1979 |
| GB | 2099838 A | 12/1982 |
| WO | 2007/048473 A1 | 5/2007 |
| WO | 2011/111054 A1 | 9/2011 |
| WO | 2014/020148 A1 | 2/2014 |
| WO | 2014/020167 A2 | 2/2014 |
| WO | 2016/020110 A1 | 2/2016 |
| WO | 2016/020111 A1 | 2/2016 |
| WO | 2016/096654 A1 | 6/2016 |
| WO | 2016/097022 A1 | 6/2016 |
| WO | 2016/097228 A1 | 6/2016 |

OTHER PUBLICATIONS

Database Registry, Chemical Abstract Service, STN Accession No. 748071-47-8 (Sep. 19, 2004).*
Database Registry, Chemical Abstract Service, STN Accession No. 4958-10-5 (Nov. 16, 1984).*
Database Registry, Chemical Abstract Service, STN Accession No. 137730-90-6 (Dec. 6, 1991).*
International Search Report issued in corresponding International Application No. PCT/SG2018/050571, dated Feb. 1, 2019 (8 pages).
Written Opinion issued in corresponding International Application No. PCT/SG2018/050571, dated Feb. 1, 2020 (7 pages).
Database Registry, Chemical Abstract Services, STN Accession No. 748071-47-8, Sep. 19, 2004 (2 pages).
Database Registry, Chemical Abstracts Services, STN Accession No. 209252-25-5, Jul. 30, 1998 (2 pages).
Database Registry, Chemical Abstracts Services, STN Accession No. 189251-75-0, May 23, 1997 (2 pages).
Database Registry, Chemical Abstracts Services, STN Accession No. 17558-86-0, Nov. 16, 1984 (2 pages).
Database Registry, Chemical Abstracts Services, STN Accession No. 17480-17-0, Nov. 16, 1984 (2 pages).
Database Registry, Chemical Abstracts Services, STN Accession No. 16241-54-6, Nov. 16, 1984 (2 pages).
Database Registry, Chemical Abstracts Services, STN Accession No. 137730-90-6, Dec. 6, 1991 (2 pages).
Database Registry, Chemical Abstracts Services, STN Accession No. 4958-10-5, Nov. 16, 1984 (2 pages).
Database Registry, Chemical Abstracts Services, STN Accession No. 1231977-17-5, Jul. 14, 2010 (2 pages).
Meyer, Alex and Klaus Fischer, "Oxidative transformation processes and products of para-phenylenediamine (PPD) and para-toluenediamine (PTD)—a review", Environmental Sciences Europe, vol. 27, No. 1, May 27, 2015 <DOI: 10.1186/S12302-015-0044-7> (16 pages).
Yuan, X. et al.; "Influence of Physicochemical Properties on the In Vitro Skin Permeation of the Enantiomers, Racemate, and Eutectics of Ibuprofen for Enhanced Transdermal Drug Delivery;" Journal of Pharmaceutical Sciences; vol. 102; No. 6; Jun. 2013; pp. 1,957-1,969 (13 pages).
Golla, S. et al.; "Virtual Design of Chemical Penetration Enhancers for Transdermal Drug Delivery;" Chem Biol Drug Des; 2012; pp. 478-487 (10 pages).
Alvarez-Sánchez, R. et al.; "Studies of Chemical Selectivity of Hapten, Reactivity, and Skin Sensitization Potency. 3. Synthesis and Studies on the Reactivity toward Model Nucleophiles of the 13C-Labeled Skin Sensitizers, 5-Chloro-2-methylisothiazol-3-one (MCI) and 2-Methylisothiazol-3-one (MI);" Chem. Res. Toxicol.; vol. 16; No. 5; 2003; pp. 627-636 (10 pages).
Eilstein, J. et al.; "Sensitization to p-amino aromatic compounds: Study of the covalent binding of 2,5-dimethyl-p-benzoquinonediimine to a model peptide by electrospray ionization tandem mass spectrometry;" Bioorganic & Medicinal Chemistry; 2008; pp. 5,482-5,489 (8 pages).
Weltzien, H. U. et al.; "T cell immune responses to haptens. Structural models for allergic and autoimmune reactions;" Toxicology; 1996; pp. 141-151 (11 pages).
Gerberick, G. F. et al.; "Development of a Peptide Reactivity Assay for Screening Contact Allergens;" Toxicological Sciences; 2004; pp. 332-343 (12 pages).
Gerberick, G. F. et al.; "Quantification of Chemical Peptide Reactivity for Screening Contact Allergens: A Classification Tree Model Approach;" Toxicological Sciences; 2007; pp. 417-427 (11 pages).

(56) References Cited

OTHER PUBLICATIONS

Bracher, M. et al.; "Studies on the potential mutagenicity of p-phenylenediamine in oxidative hair dye mixtures;" Mutation Research; 1990; pp. 313-323 (11 pages).

Burnett, C. M. et al.; "Multigeneration Reproduction and Carcinogenicity Studies in Sprague-Dawley Rats Exposed Topically to Oxidative Hair-Colouring Formulations Containing P-Phenylenediamine and Other Aromatic Amines;" Food Chem. Toxicol; vol. 26; No. 5; 1988; pp. 467-474 (8 pages).

Pot, L. M. et al.; "Penetration and haptenation of p-phenylenediamine;" Contact Dermatitis; 2013; pp. 193-207 (15 pages).

Blomeke, B. et al.; "Elicitation response characteristics to mono- and to N,N'-diacetyl-para-phenylenediamine;" Contact Dermatitis; 2008; pp. 355-358 (4 pages).

Aeby, P. et al.; "Skin Sensitization to p-Phenylenediamine: The Diverging Roles of Oxidation and N-Acetylation for Dendritic Cell Activation and the Immune Response;" The Society for Investigative Dermatology; 2009; pp. 99-129 (11 pages).

Krasteva, M. et al.; "Dissociation of Allergenic and Immunogenic Functions in Contact Sensitivity to Para-Phenylenediamine;" In. Arch. Allergy Immunol; 1993; pp. 200-204 (5 pages).

Sousa, A. C. et al.; "Eco-friendly synthesis of indo dyes mediated by a bacterial laccase;" Green Chemistry; 2016; pp. 6,063-6,070 (8 pages).

Database Registry, Chemical Abstracts Services, STN Accession No. 537-65-5, 2021 (5 pages).

OECD/OCDE; "OECD Guideline for the Testing of Chemicals, In Chemico Skin Sensitisation: Direct Peptide Reactivity Assay (DPRA);" Feb. 4, 2015 (19 pages).

Gerberick, F. et al.; "Chemical Reactivity Measurement and the Predictive Identification of Skin Sensitisers;" ECVAM Workshop 64; 2008; pp. 215-242 (28 pages).

Kawakubo, Y. et al.; "N-Acetylation of Paraphenylenediamine in Human Skin and Keratinocytes;" The Journal of Pharmacology and Experimental Therapeutics; vol. 292; No. 1; 2000; pp. 150-155 (6 pages).

Kulszewicz-Bajer, I. et al.; "Synthesis and spectroscopic properties of aniline tetramers. Comparative studies;" New J. Chem.; 2004; pp. 669-675 (7 pages).

\* cited by examiner

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Cysteine peptide
<220> FEATURE:
<221> NAME/KEY: MISC_FEATURE
<222> LOCATION: (1)..(1)
<223> OTHER INFORMATION: Arg is acetylated.

<400> SEQUENCE: 1

Arg Phe Ala Ala Cys Ala Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Lysine peptide
<220> FEATURE:
<221> NAME/KEY: MISC_FEATURE
<222> LOCATION: (1)..(1)
<223> OTHER INFORMATION: Arg is acetylated.

<400> SEQUENCE: 2

Arg Phe Ala Ala Lys Ala Ala
1               5
```

US 11,129,782 B2

DERIVATIVES OF PPD USEFUL FOR COLORING HAIR AND SKIN

FIELD OF INVENTION

The current invention relates to compounds and compositions containing said compounds that may act to provide a colouring to the skin or hair of a subject. The compounds disclosed herein may be less prone to causing an allergic or other immune response in a subject.

BACKGROUND

Hair and temporary skin colourings are among the most widely used cosmetic treatments today. Many of the dyes used in these treatments contain unstable di-/tri-functional aromatic amines that undergo oxidative polymerization to provide the desired pigmentation. However, the main component in dark dyes, para-phenylenediamine (PPD) or oxidative and enzymatic alterations of this diamine, can be irritants and very potent contact allergens. These potentially life-threatening allergies can appear as localized or generalized contact allergies with sometimes severe blister formations, itch and facial swellings and a potential to develop systemic reactions such as lymphadenopathy, asthma or methemoglobinemia, as well as fevers.

Para-phenylenediamine was nominated in 2006 as "allergene of the year". It is a common amine-containing compound used particularly in hair dyes and non-permanent tattoos. PPD can penetrate easily through skin, where it can damage cells of the viable epidermis and interact with immune cells in the skin. This is also true for PPD derivatives produced by metabolic processes in the skin or by non-ionizing radiation (ultraviolet/visible/infrared light). In addition, the interaction of PPD and its derivatives with keratin proteins in the stratum corneum can form a depot, prolonging the release of PPD deeper into the skin, and making allergic reactions, particularly to PPD, a dangerous and long-lasting condition.

As discussed below, PPD (32A) can be oxidised readily using hydrogen peroxide, resulting in several products. The major product isolated from PPD oxidation was the trimeric form of PPD, commonly known as Bandrowski's base (BB; 32). In addition to BB, a small amount of p-nitroaniline (33) and 4,4'-diaminoazobenzene (34) were also isolated (FIG. 1).

Our own experiments using 1% PPD solution from a standardized hair dresser patch test series (Chemotechnique) showed that when the PPD is contained within paraffin (as supplied), it is protected against oxidation. This is true even after 2 days of patch test as the test field remains colourless. Our mass spectrometry measurements have shown that even after several days in air the PPD patch test formulation in paraffin does not show any Bandrowski base or other oxidation/metabolic derivatives in this formulation—only the parent compound PPD is present.

However, sensitized patients develop a clear localised contact dermatitis in response to this PPD formulation. This suggests that PPD itself is the major allergen, either by haptenation or on its own (maybe through Toll-like receptor activation). Therefore, application of coloured polymers that cannot cross the skin barrier and which do not contain any PPD may potentially avoid the serious toxic and allergenic effects of hair dyes and temporary tattoos on skin and immune cells. Thus there remains a need for hair and temporary skin colourings that avoid such allergic responses and may be suitable for use in subjects who show sensitivity to conventional colouring materials.

DRAWINGS

FIG. 1 depicts the reaction of PPD with hydrogen peroxide to form a number of reaction products.

FIG. 2: Multiple reaction monitoring chromatograms for p-phenyenediamine (PPD; m/z 109.20-92.0), N-acetyl-p-phenylenediamine (MAPPD; m/z 151.40-92.0), Bandrowski's base (BB; m/z 319.23-303.30), N,N'-diacety-p-phenyenediamine (DAPPD; m/z 193.20-109.10), and internal standard 2-amino-5-nitro pyridine (ANP; m/z 140.20-94.20) after the analysis in Dulbecco's phosphate buffer saline (DPBS) medium.

FIG. 3: Multiple reaction monitoring chromatograms for N-(4-aminophenyl)benzene-1,4-diamine (dimer; m/z 198.20-182.0), N-[4-(4-aminoanilino)phenyl]acetamide (monoacetyl dimer; m/z 242.30-142.20), N,N-[azanediyldi (1,4-phenyene)]diacetamide (diacetyl dimer; m/z 284.30-107.0), and Internal standard, 2-amino-5-nitro pyridine (ANP; m/z 140.20-94.20) after the analysis in DPBS medium.

FIG. 4: LCMS spectrum for the identification of PPD (m/z [M+H]+ 109.2), and metabolites MAPPD (m/z [M+H]+ 151.4), DAPPD (m/z [M+H]+ 193.2) and BB (m/z [M+H]+ 319.2) in receiver DPBS medium at the end of the experiment. Comparative DPBS medium did not show any signal at the corresponding m/z values.

FIG. 5: LCMS spectrum for the identification of PPD (m/z [M+H]+ 198.2), and metabolites: monoacetyl dimer (m/z [M+H]+ 242.30) and diacetyl dimer (m/z [M+H]+ 284.30) in receiver DPBS medium at the end of the experiment. Comparative DPBS medium did not show any signal at the corresponding m/z values.

FIG. 6: Concentration dependent cytotoxicity of the PPD and its analogues on HaCaT cells after 72 hours of incubation at 37° C.

FIG. 7: Cumulative amount profiles (n=3) of (a) PPD and associated metabolites (b) Bandrowski's base (c) Diacetyl-PPD and (d) Monoacetyl-PPD.

FIG. 8: juxtaposes the PPD derivatives and their metabolites (monoacetyl & diacetyl) permeation (a. PPD derivative 1, b. PPD derivative 2, c. PPD derivative 3, d. PPD derivative 4)

FIG. 9: (a) Comparison of cumulative amount profile of PPD, ME PPD vs PPD derivatives 1-4, 6 and 15. PPD derivative 5 was not detectable as it did not permeate the skin at all.

FIG. 10: Raman spectra of (a) PPD and (b) PPD-1 solution (1% w/v in water) at different depths in the solution.

FIG. 11: Raman spectra of PPD-1 solution (1% w/v in water) in a skin organotypic culture at depths (a) 0.5 to 30.5 μm and (b) 36.5 to 40.5 μm.

FIG. 12: Direct Cysteine (1:10)/Lysine (1:50) mean peptide reactivity at 20 min & 24 hr of incubation. Recommended thresholds (6.38%, 22.62%, 42.47%, 100%) of the mean peptide depletion, Note: There is no classification for sensitizing potentials at 20 min DPRA. The experiment was performed in triplicate.

DESCRIPTION

Figure 1:
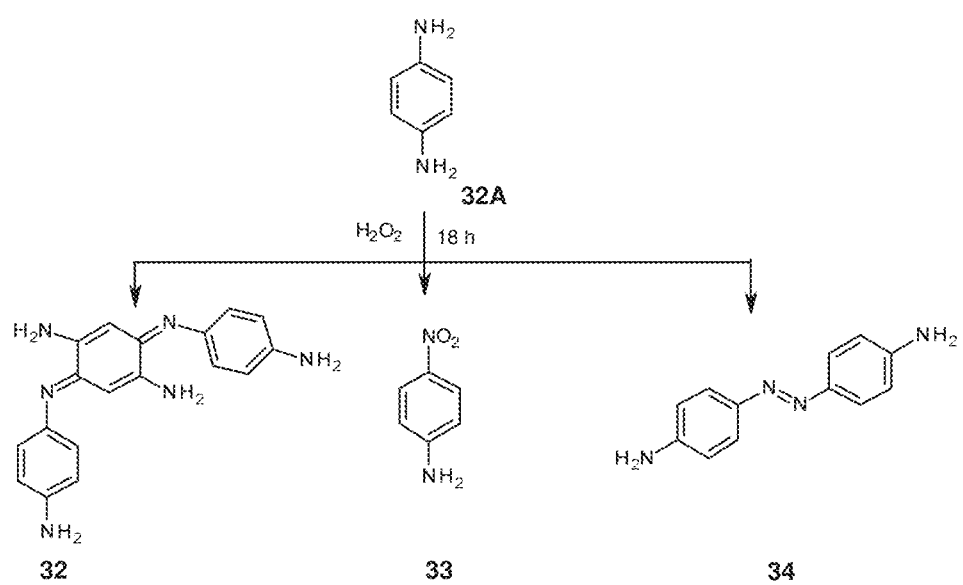

The current invention overcomes the problems identified above through the use of analogues of PPD that retain the dyeing effect (with or without oxidation), but avoid the sensitizing issues associated with PPD and/or its oxidation products. That is, the compounds disclosed hereinbelow may not provoke an allegoric or other immune reaction from a subject when used for the purposes of dyeing hair or colouring the skin.

Thus, according to a first aspect of the invention, there is provided a compound of formula I:

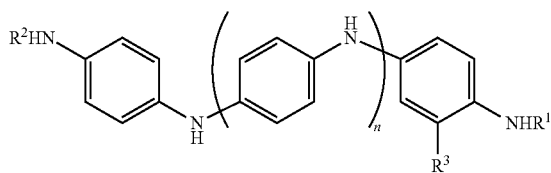

wherein:
$R^1$ and $R^2$ independently represent H or $C_{5-10}$ alkyl, which latter group is unsubstituted or substituted with one or more substituents selected from:
- $C_{1-10}$ alkyl (which group is unsubstituted or substituted by one or more substituents selected from OH, nitro, CN, $OR^{4a}$, $NR^{4b}R^{4c}$, aryl and $Het^1$);
- $Cy^1$ (which $Cy^1$ group is unsubstituted or substituted by one or more substituents selected from nitro, CN, $C_{1-10}$ alkyl (which latter group is unsubstituted or substituted by one or more substituents selected from OH, =O, $C_{1-4}$ alkyl and $C_{1-4}$ alkoxy), and $OR^{5a}$, $S(O)_qR^{5b}$, $S(O)_2NR^{5c}R^{5d}$, $NR^{5e}S(O)_2R^{5f}$, $NR^{5g}R^{5h}$);
- $Het^a$ (which $Het^a$ group is unsubstituted or substituted by one or more substituents selected from nitro, CN, $C_{1-6}$ alkyl (which latter group is unsubstituted or substituted by one or more substituents selected from OH, =O, halo, $C_{1-4}$ alkyl and $C_{1-4}$ alkoxy), $OR^{6a}$, $S(O)R^{6b}$, $S(O)_2NR^{6c}R^{6d}$, $NR^{6e}S(O)_2R^{6f}$, $NR^{6g}R^{6h}$); and $OR^{7a}$, $S(O)_qR^{7b}$, $S(O)_2NR^{7c}R^{7d}$, $NR^{7e}S(O)_2R^{7f}$ and $NR^{7g}R^{7h}$, $R^3$ represents H, $C_{1-10}$ alkyl, $OC_{1-10}$ alkyl, $C(O)OC_{1-10}$ alkyl or $OC(O)C_{1-10}$ alkyl, which latter four groups are unsubstituted or substituted with one or more substituents selected from:
- $C_{1-10}$ alkyl (which group is unsubstituted or substituted by one or more substituents selected from OH, nitro, CN, $OR^{8a}$, $NR^{8b}R^{8c}$, aryl and $Het^2$);
- $Cy^2$ (which $Cy^2$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{9a}$, $S(O)_qR^{9b}$, $S(O)_2NR^{9c}R^{9d}$, $NR^{9e}S(O)_2R^{9f}$, $NR^{9g}R^{9h}$);
- $Het^b$ (which $Het^b$ group is unsubstituted or substituted by one or more substituents selected from nitro, CN, $C_{1-6}$ alkyl (which latter group is unsubstituted or substituted by one or more substituents selected from OH, =O, halo, $C_{1-4}$ alkyl and $C_{1-4}$ alkoxy), $OR^{10a}$, $S(O)_qR^{10b}$, $S(O)_2NR^{10c}R^{10d}$, $NR^{10e}S(O)_2R^{10f}$, $NR^{10g}R^{10h}$); and $OR^{11a}$, $S(O)_qR^{11b}$, $S(O)_2NR^{11c}R^{11d}NR^{11e}S(O)_2R^{11f}$ and $NR^{11g}R^{11h}$, $Het^1$ and $Het^2$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{12a}$ and $C_{1-10}$ alkyl, which latter group is unsubstituted;

$Cy^1$ and $Cy^2$ represent, independently at each occurrence, a 3- to 6-membered aromatic, fully saturated or partially unsaturated carbocyclic ring;

$R^{4a}$ to $R^{4c}$, $R^{5a}$ to $R^{5h}$, $R^{6a}$ to $R^{6h}$, $R^{7a}$ to $R^{7h}$, $R^{8a}$ to $R^{8c}$, $R^{9a}$ to $R^{9h}$, $R^{10a}$ to $R^{10h}$, $R^{11a}$ to $R^{11h}$, independently represent, at each occurrence, H, or $C_{1-10}$ alkyl (which latter group is unsubstituted or substituted by one or more substituents selected from $C_{1-6}$ alkyl, $OR^{12b}$), or $R^{5-7c}$ and $R^{5-7d}$, $R^{9-11c}$ and $R^{9-11d}$, $R^{5-7g}$ and $R^{5-7h}$, $R^{9-11g}$ and $R^{9-11h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and $C_{1-6}$ alkyl;

$Het^a$ and $Het^b$ independently represent 4- to 14-membered heterocyclic groups containing one or more heteroatoms selected from O, S and N;

$R^{12a-b}$ independently represents, at each occurrence, H or $C_{1-4}$ alkyl, n represents 0 to 4, or a physiologically acceptable salt or solvate, or an oxidised derivative thereof, provided that when $R^1$ and $R^2$ are H, and n is 0, 1 or 2, $R^3$ is not H.

In a second aspect according to the invention there is provided a method of dyeing hair or of applying a temporary tattoo, which method comprises applying a composition comprising a compound of formula I or a physiologically acceptable salt or solvate, or an oxidised derivative thereof, to the hair or skin of a subject, wherein the compound of formula I has the structure:

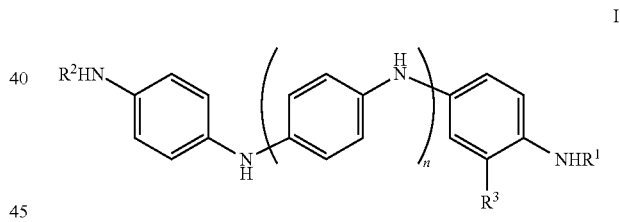

wherein:
$R^1$ and $R^2$ independently represent H or $C_{5-10}$ alkyl, which latter group is unsubstituted or substituted with one or more substituents selected from:
- $C_{1-10}$ alkyl (which group is unsubstituted or substituted by one or more substituents selected from OH, nitro, CN, $OR^{4a}$, $NR^{4b}R^{4c}$, aryl and $Het^1$);
- $Cy^1$ (which $Cy^1$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{5a}$, $S(O)_qR^{5b}$, $S(O)_2NR^{5c}R^{5d}$, $NR^{5e}S(O)_2R^{5f}$, $NR^{5g}R^{5h}$);
- $Het^a$ (which $Het^a$ group is unsubstituted or substituted by one or more substituents selected from nitro, CN, $C_{1-6}$ alkyl (which latter group is unsubstituted or substituted by one or more substituents selected from OH, =O, halo, $C_{1-4}$ alkyl and $C_{1-4}$ alkoxy), $OR^{6a}$, $S(O)_qR^{6b}$, $S(O)_2NR^{6c}R^{6d}$, $NR^{6e}S(O)_2R^{6f}$, $NR^{6g}R^{6h}$); and $OR^{7a}$, $S(O)_qR^{7b}$, $S(O)_2NR^{7c}R^{7d}$, $NR^{7e}S(O)_2R^{7f}$ and $NR^{7g}R^{7h}$, R³ represents H, $C_{1-10}$ alkyl, $OC_{1-10}$ alkyl, $C(O)OC_{1-10}$ alkyl or $OC(O)C_{1-10}$ alkyl, which latter four groups are unsubstituted or substituted with one or more substituents selected from:
- $C_{1-10}$ alkyl (which group is unsubstituted or substituted by one or more substituents selected from OH, nitro, CN, $OR^{8a}$, $NR^{8b}R^{8c}$, aryl and $Het^2$);
- $Cy^2$ (which $Cy^2$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{9a}$, $S(O)_qR^{9b}$, $S(O)_2NR^{9c}R^{9d}$, $NR^{9e}S(O)_2R^{9f}$, $NR^{9g}R^{9h}$);
- $Het^b$ (which $Het^b$ group is unsubstituted or substituted by one or more substituents selected from nitro, CN, $C_{1-6}$ alkyl (which latter group is unsubstituted or substituted by one or more substituents selected from OH, =O, halo, $C_{1-4}$ alkyl and $C_{1-4}$ alkoxy), $OR^{10a}$, $S(O)_qR^{10b}$, $S(O)_2NR^{10c}R^{10d}$, $NR^{10e}S(O)_2R^{10f}$, $NR^{10g}R^{10h}$); and $OR^{11a}$, $S(O)_qR^{11b}$, $S(O)_2NR^{11c}R^{11d}NR^{11e}S(O)_2R^{11f}$ and $NR^{11g}R^{11h}$, $Het^1$ and $Het^2$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{12a}$ and $C_{1-10}$ alkyl, which latter group is unsubstituted;

$Cy^1$ and $Cy^2$ represent, independently at each occurrence, a 3- to 6-membered aromatic, fully saturated or partially unsaturated carbocyclic ring;

$R^{4a}$ to $R^{4c}$, $R^{5a}$ to $R^{5h}$, $R^{6a}$ to $R^{6h}$, $R^{7a}$ to $R^{7h}$, $R^{8a}$ to $R^{8c}$, $R^{9a}$ to $R^{9h}$, $R^{10a}$ to $R^{10h}$, $R^{11a}$ to $R^{11h}$ independently represent, at each occurrence, H, or $C_{1-10}$ alkyl (which latter group is unsubstituted or substituted by one or more substituents selected from $C_{1-6}$ alkyl, $OR^{12b}$), or $R^{5-7c}$ and $R^{5-7d}$, $R^{9-11c}$ and $R^{9-11d}$, $R^{5-7g}$ and $R^{5-7h}$, $R^{9-11g}$ and $R^{9-11h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and $C_{1-10}$ alkyl;

$Het^a$ and $Het^b$ independently represent 4- to 14-membered heterocyclic groups containing one or more heteroatoms selected from O, S and N;

$R^{12a-b}$ independently represents, at each occurrence, H or $C_{1-4}$ alkyl, n represents 0 to 4, or a physiologically acceptable salt or solvate, or an oxidised derivative thereof, provided that when $R^1$ and $R^2$ are H, and n is 0, $R^3$ is not H.

References herein (in any aspect or embodiment of the invention) to compounds of formula I includes references to such compounds per se, to tautomers of such compounds, as well as to physiologically acceptable salts or solvates, or oxidised derivatives of such compounds.

Physiologically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of physiologically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-12-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), a-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs*, Second Edition, published by SSCI, Inc of West Lafayette, Ind., USA, 1999, ISBN 0-967-06710-3.

"Oxidised derivatives" of compounds of formula I as defined herein are compounds that may be obtained from the compounds of formula I that are exposed to an oxidising agent, such as hydrogen peroxide. It will be appreciated that the resulting oxidised compounds may be analogous to the oxidation products of PPD.

Compounds of formula I, as well as physiologically acceptable salts, solvates and oxidised derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention.

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

For the avoidance of doubt, in the context of the present invention, the terms "dyeing" and "tattooing" refers to the application of a cosmetic treatment to a body part of a subject, such as the skin (in the case of tattooing) or the hair (in the case of dyeing).

As used herein the terms "subject" is well-recognized in the art, and, is used herein to refer to a mammal, including dog, cat, rat, mouse, monkey, cow, horse, goat, sheep, pig, camel, and, most preferably, a human. The term does not denote a particular age or sex. Thus, adult and newborn (in some cases) subjects, whether male or female, are intended to be covered.

It will be appreciated that an effective amount of the compound of formula I, may be used to effect the dyeing and/or temporary tattooing of a subject. The term "effective amount" refers to an amount of a compound, which confers the desired colouring effect on the treated subject (e.g. sufficient to dye hair or temporarily tattoo skin). The effect may be objective (i.e. measurable by some test or marker) or subjective (i.e. the subject can see the difference).

The term "halo", when used herein, includes references to fluoro, chloro, bromo and iodo.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Unless otherwise stated, the term "alkyl" refers to an unbranched or branched, cyclic, saturated or unsaturated (so forming, for example, an alkenyl or alkynyl)hydrocarbyl radical, which may be substituted or unsubstituted (with, for example, one or more halo atoms). Where the term "alkyl" refers to an acyclic group, it is preferably C1-10 alkyl and, more preferably, C1-6 alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably C3-12 cycloalkyl and, more preferably, C5-10 (e.g. C5-7) cycloalkyl.

The term "heteroaryl" when used herein refers to an aromatic group containing one or more heteroatom(s) (e.g. one to four heteroatoms) preferably selected from N, O and S (so forming, for example, a mono-, bi-, or tricyclic heteroaromatic group). Heteroaryl groups include those which have between 5 and 14 (e.g. 10) members and may be monocyclic, bicyclic or tricyclic, provided that at least one of the rings is aromatic. However, when heteroaryl groups are bicyclic or tricyclic, they are linked to the rest of the molecule via an aromatic ring. Heterocyclic groups that may be mentioned include benzothiadiazolyl (including 2,1,3-benzothiadiazolyl), isothiochromanyl and, more preferably, acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Particularly preferred heteroaryl groups include pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, thiophenetyl, thiophenyl, pyranyl, carbazolyl, acridinyl, quinolinyl, benzoimidazolyl, benzthiazolyl, purinyl, cinnolinyl and pterdinyl. Particularly preferred heteroaryl groups include monocylic heteroaryl groups.

In certain embodiments, compounds of formula I that may be mentioned herein include ones in which at least one of $R^1$ and $R^2$ is not H.

In embodiments of formula I that may be mentioned herein:
(a) $R^1$ and $R^2$ may independently represent H or $C_{6-8}$ alkyl, which latter group is unsubstituted or substituted with one or more substituents selected from $C_{1-3}$ alkyl, $Cy^1$ (which $Cy^1$ group is unsubstituted or substituted by one or more substituents selected from nitro, $C_{1-3}$ alkyl, and $OR^{5a}$), $Het^a$ (which $Het^a$ group is unsubstituted or substituted by one or more substituents selected from nitro, $C_{1-3}$ alkyl, and $OR^{6a}$), and $OR^{7a}$ (e.g. $R^1$ and $R^2$ represent H or $C_{6-8}$ alkyl, which latter group is unsubstituted or substituted by a phenyl ring, which phenyl ring is unsubstituted or substituted by one or more substituents selected from nitro, methyl, OH and $OCH_3$, optionally wherein $R^2$ represents H);
(b) $R^3$ may represent H, $C_{1-6}$ alkyl, O—$C_{1-6}$ alkyl, or $C(O)OC_{1-6}$ alkyl, which latter two groups are unsubstituted or substituted with one or more substituents selected from $C_{1-3}$ alkyl;
(c) $Cy^1$ when present represents independently a phenyl ring.
(d) $R^{4a}$ to $R^{4c}$, $R^{5a}$ to $R^{5h}$, $R^{6a}$ to $R^{6h}$, $R^{7a}$ to $R^{7h}$, $R^{8a}$ to $R^{8c}$, $R^{9a}$ to $R^{9h}$, $R^{10a}$ to $R^{10h}$, $R^{11a}$ to $R^{11h}$, independently represent, at each occurrence when present, H, or $C_{1-6}$ alkyl;
(e) n represents 1 to 3.

In further embodiments of formula I:
(a) $R^1$ and $R^2$ independently represent H or $C_{6-8}$ alkyl, which latter group is unsubstituted or substituted by a phenyl ring, which phenyl ring is unsubstituted or substituted by one or more substituents selected from nitro, $C_{1-3}$ alkyl, and $OR^{5a}$, or
$R^1$ may represents $C_{6-8}$ alkyl, which latter group is unsubstituted or substituted with one or more substituents selected from $C_{1-3}$ alkyl, $Cy^1$ (which $Cy^1$ group is unsubstituted or substituted by one or more substituents selected from nitro, $C_{1-3}$ alkyl, and $OR^{5a}$), $Het^a$ (which $Het^a$ group is unsubstituted or substituted by one or more substituents selected from nitro, $C_{1-3}$ alkyl, and $OR^{6a}$), and $OR^{7a}$, and
$R^2$ may represent H or $C_{6-8}$ alkyl, which latter group is unsubstituted or substituted with one or more substituents selected from $C_{1-3}$ alkyl, $Cy^1$ (which $Cy^1$ group is unsubstituted or substituted by one or more substituents selected from nitro, $C_{1-3}$ alkyl, and $OR^{5a}$), $Het^a$ (which $Het^a$ group is unsubstituted or substituted by one or more substituents selected from nitro, $C_{1-3}$ alkyl, and $OR^{6a}$), and $OR^{7a}$;
(b) n represents 0 to 3.

Other compounds of formula I that may be mentioned per se include compounds of the examples described hereinafter. Thus, embodiments of the invention that may be mentioned include those in which the compound of formula I is a compound selected from the list:
(i) 4-Amino-(3-hexyloxy)-4'-aminodiphenylamine;
(ii) hexyl [2-amino-5-(4-aminophenylamino)]benzoate;
(iii) 4-hexylamino-(3-hexyloxy)-4'-aminodiphenylamine;
(iv) 4-Amino-4'-[(4-tolylaminomethyl)phenyl]diphenylamine;
(v) $N^1$-[4-(4-tolylaminomethyl)phenyl]-$N^4$-(4-aminophenyl)-1,4-benzenediamine;
(vi) $N^4$-[(4-nitrophenyl)methyl]-$N^1$-[4-[(4-nitrophenyl)methylamino]phenyl]-benzene-1,4-diamine;
(vii) $N^4$-[(4-methoxyphenyl)methyl]-$N^1$-[4-[(4-ethoxyphenyl)methylamino]-phenyl]benzene-1,4-diamine;
(viii) $N^4$-(p-tolylmethyl)-$N^1$-[4-(p-tolylmethylamino)phenyl]benzene-1,4-diamine; and
(ix) 4-[[4-[4-[(4-hydroxyphenyl)methylamino]anilino]anilino]methyl]phenol.

Similarly, compounds of formula I that may be used in the method described hereinbefore may include those in which the compound of formula I is a compound selected from the list:
(a) $N^1,N^4$-bis(4-aminophenyl)-1,4-benzenediamine; (b) 4-Amino-(3-hexyloxy)-4'-aminodiphenylamine;
(c) hexyl [2-amino-5-(4-aminophenylamino)]benzoate;
(d) 4-hexylamino-(3-hexyloxy)-4'-aminodiphenylamine;
(e) 4,4'-Bis[(4-aminophenyl)amino]diphenylamine;
(f) 4-Amino-4'-[(4-tolylaminomethyl)phenyl]diphenylamine;
(g) $N^1$-[4-(4-tolylaminomethyl)phenyl]-$N^4$-(4-aminophenyl)-1,4-benzenediamine;
(h) $N^4$-[(4-nitrophenyl)methyl]-$N^1$-[4-[(4-nitrophenyl)methylamino]phenyl]-benzene-1,4-diamine;
(i) $N^4$-[(4-methoxyphenyl)methyl]-$N^1$-[4-[(4-ethoxyphenyl)methylamino]-phenyl]benzene-1,4-diamine;
(j) $N^4$-(p-tolylmethyl)-$N^1$-[4-(p-tolylmethylamino)phenyl]benzene-1,4-diamine; and
(k) 4-[[4-[4-[(4-hydroxyphenyl)methylamino]anilino]anilino]methyl]phenol.

Similarly, compounds of formula I that may be mentioned herein in relation to the method may include those in which the compound of formula I is a compound selected from the list:
(a) 4,4'-Bis[(4-aminophenyl)amino]diphenylamine;
(b) 4-Amino-4'-[(4-tolylaminomethyl)phenyl]diphenylamine; and
(c) $N^1$-[4-(4-tolylaminomethyl)phenyl]-$N^4$-(4-aminophenyl)-1,4-benzenediamine.

A particular compound of formula I that may be mentioned herein per se or in relation to the method is hexyl [2-amino-5-(4-aminophenylamino)]benzoate.

Additional compounds of the invention may have a different structure, while still providing the benefits that will be discussed in more detail herein. Thus, according to a third aspect of the invention, there is provided a compound of formula II:

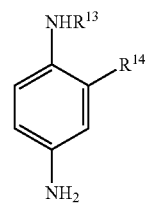

II wherein:
$R^{13}$ represents H or $C_{6-10}$ alkyl, which latter group is unsubstituted or substituted with one or more substituents selected from:
$C_{1-10}$ alkyl (which group is unsubstituted or substituted by one or more substituents selected from OH, nitro, CN, $OR^1$, $NR^{15b}R^{15c}$, aryl and $Het^3$);
$Cy^3$ (which $Cy^3$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{16a}$, $S(O)_qR^{16b}$, $S(O)_2NR^{16c}R^{16d}$, $NR^{16e}S(O)_2R^{16f}$, $NR^{16g}R^{16h}$);
$Het^c$ (which $Het^c$ group is unsubstituted or substituted by one or more substituents selected from nitro, CN, $C_{1-6}$ alkyl (which latter group is unsubstituted or substituted by one or more substituents selected from OH, =O, halo, $C_{1-4}$ alkyl and $C_{1-4}$ alkoxy), $OR^{17a}$, $S(O)_qR^{17b}$, $S(O)_2NR^{17c}R^{17d}$, $NR^{17e}S(O)_2R^{17f}$, $NR^{17g}R^{17h}$); and $OR^{18a}$, $S(O)_qR^{18b}$, $S(O)_2NR^{18c}R^{18d}$, $NR^{18e}S(O)_2R^{18f}$ and $NR^{18g}R^{18h}$, $R^{14}$ represents H, $C_{1-10}$ alkyl, $OC_{1-10}$ alkyl, $C(O)OC_{1-10}$ alkyl or $OC(O)C_{1-10}$ alkyl, which latter four groups are unsubstituted or substituted with one or more substituents selected from:

$C_{1-10}$ alkyl (which group is unsubstituted or substituted by one or more substituents selected from OH, nitro, CN, $OR^{19a}$, $NR^{19b}R^{19c}$, aryl and $Het^4$);

$Cy^4$ (which $Cy^4$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{20a}$, $S(O)R^{20b}$, $S(O)_2NR^{20c}R^{20d}$, $NR^{20e}S(O)_2R^{20f}$, $NR^{20g}R^{20h}$)

$Het^d$ (which $Het^d$ group is unsubstituted or substituted by one or more substituents selected from nitro, CN, $C_{1-10}$ alkyl (which latter group is unsubstituted or substituted by one or more substituents selected from OH, =O, halo, $C_{1-4}$ alkyl and $C_{1-4}$ alkoxy), $OR^{21a}$, $S(O)_qR^{21b}$, $S(O)_2NR^{21c}R^{21d}$, $NR^{21e}S(O)_2R^{21f}$, $NR^{21g}R^{21h}$); and $OR^{22a}$, $S(O)_qR^{22b}$, $S(O)_2NR^{22c}R^{22d}$, $NR^{22e}S(O)_2R^{22f}$ and $NR^{22g}R^{22h}$, $Het^3$ and $Het^4$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{23a}$ and $C_{1-10}$ alkyl, which latter group is unsubstituted;

$Cy^3$ and $Cy^4$ represent, independently at each occurrence, a 3- to 6-membered fully saturated or partially unsaturated carbocyclic ring;

$R^{15a}$ to $R^{15c}$, $R^{16a}$ to $R^{16h}$, $R^{17a}$ to $R^{17h}$, $R^{18a}$ to $R^{18h}$, $R^{19a}$ to $R^{19c}$, $R^{20a}$ to $R^{20h}$, $R^{21a}$ to $R^{21h}$, $R^{22a}$ to $R^{22h}$ independently represent, at each occurrence, H, or $C_{1-10}$ alkyl (which latter group is unsubstituted or substituted by one or more substituents selected from $C_{1-6}$ alkyl, $OR^{23b}$), or $R^{16-18c}$ and $R^{16-18d}$, $R^{20-22c}$ and $R^{20-22d}$, $R^{16-18g}$ and $R^{16-18h}$, $R^{20-22g}$ and $R^{20-22h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and $C_{1-6}$ alkyl;

$Het^c$ and $Het^d$ independently represent 4- to 14-membered heterocyclic groups containing one or more heteroatoms selected from O, S and N; $R^{23a-b}$ independently represents, at each occurrence, H or $C_{1-4}$ alkyl, or an oxidised derivative thereof, provided that when $R^{13}$ is H, $R^{14}$ is not n-hexyl.

In a fourth aspect according to the invention there is provided method of dyeing hair or of applying a temporary tattoo, which method comprises applying a composition comprising a compound of formula II or a physiologically acceptable salt or solvate, or an oxidised derivative thereof, to the hair or skin of a subject, wherein the compound of formula II has the structure:

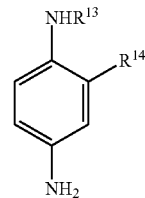

II wherein:
$R^{13}$ represents H or $C_{6-10}$ alkyl, which latter group is unsubstituted or substituted with one or more substituents selected from:

$C_{1-10}$ alkyl (which group is unsubstituted or substituted by one or more substituents selected from OH, nitro, CN, $OR^{15a}$, $NR^{15b}R^{15c}$, aryl and $Het^3$);

$Cy^3$ (which $Cy^3$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{16}$, $S(O)_qR^{16b}$, $S(O)_2NR^{16c}R^{16d}$, $NR^{16e}S(O)_2R^{16f}$, $NR^{16g}R^{16h}$);

$Het^c$ (which $Het^c$ group is unsubstituted or substituted by one or more substituents selected from nitro, CN, $C_{1-6}$ alkyl (which latter group is unsubstituted or substituted by one or more substituents selected from OH, =O, halo, $C_{1-4}$ alkyl and $C_{1-4}$ alkoxy), $OR^{17a}$, $S(O)_qR^{17b}$, $S(O)_2NR^{17c}R^{17d}$, $NR^{17e}S(O)_2R^{17f}$, $NR^{17g}R^{17h}$); and $OR^{18a}$, $S(O)_qR^{18b}$, $S(O)_2NR^{18c}R^{18d}$, $NR^{18e}S(O)_2R^{18f}$ and $NR^{18g}R^{18h}$, $R^{14}$ represents H, $C_{1-10}$ alkyl, $OC_{1-10}$ alkyl, $C(O)OC_{1-10}$ alkyl or $OC(O)C_{1-10}$ alkyl, which latter four groups are unsubstituted or substituted with one or more substituents selected from:

$C_{1-10}$ alkyl (which group is unsubstituted or substituted by one or more substituents selected from OH, nitro, CN, $OR^{19a}$, $NR^{19b}R^{19c}$, aryl and $Het^4$);

$Cy^4$ (which $Cy^4$ group is unsubstituted or substituted by one or more substituents selected from nitro, CN, $C_{1-6}$ alkyl (which latter group is unsubstituted or substituted by one or more substituents selected from OH, =O, $C_{1-4}$ alkyl and $C_{1-4}$ alkoxy), and $OR^{20a}$, $S(O)_qR^{20b}$, $S(O)_2NR^{20c}R^{20d}$, $NR^{20e}S(O)_2R^{20f}$, $NR^{20g}R^{20h}$)

$Het^d$ (which $Het^d$ group is unsubstituted or substituted by one or more substituents selected from nitro, CN, $C_{1-10}$ alkyl (which latter group is unsubstituted or substituted by one or more substituents selected from OH, =O, halo, $C_{1-4}$ alkyl and $C_{1-4}$ alkoxy), $OR^{21a}$, $S(O)_qR^{21b}$, $S(O)_2NR^{21c}R^{21d}$, $NR^{21e}S(O)_2R^{21f}$, $NR^{21g}R^{21h}$); and $OR^{22a}$, $S(O)_qR^{22b}$, $S(O)_2NR^{22c}R^{22d}$, $NR^{22e}S(O)_2R^{22f}$ and $NR^{22g}R^{22h}$, $Het^3$ and $Het^4$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{23a}$ and $C_{1-10}$ alkyl, which latter group is unsubstituted;

$Cy^3$ and $Cy^4$ represent, independently at each occurrence, a 3- to 6-membered fully saturated or partially unsaturated carbocyclic ring;

$R^{15a}$ to $R^{15c}$, $R^{16a}$ to $R^{16h}$, $R^{17a}$ to $R^{17h}$, $R^{18a}$ to $R^{18h}$, $R^{19a}$ to $R^{19c}$, $R^{20a}$ to $R^{20h}$, $R^{21a}$ to $R^{21h}$, $R^{22a}$ to $R^{22h}$, independently represent, at each occurrence, H, or $C_{1-10}$ alkyl (which latter group is unsubstituted or substituted by one or more substituents selected from $C_{1-6}$ alkyl, $OR^{23b}$), or $R^{16-18c}$ and $R^{16-18d}$, $R^{20-22c}$ and $R^{20-22d}$, $R^{16-18g}$ and $R^{16-18h}$, $R^{20-22g}$ and $R^{20-22h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and $C_{1-6}$ alkyl;

Het$^c$ and Het$^d$ independently represent 4- to 14-membered heterocyclic groups containing one or more heteroatoms selected from O, S and N;

$R^{23a-b}$ independently represents, at each occurrence, H or $C_{1-4}$ alkyl, or an oxidised derivative thereof.

References herein (in any aspect or embodiment of the invention) to compounds of formula II includes references to such compounds per se, to tautomers of such compounds, as well as to physiologically acceptable salts or solvates, or oxidised derivatives of such compounds.

The terms "physiologically acceptable salts and solvates" and "oxidised derivatives" take the same meanings, by analogy, to the definitions provided hereinbefore for the compounds of formula I.

Compounds of formula II may contain double bonds and may thus exist as E (entgegen) and Z (zusammen) geometric isomers about each individual double bond. All such isomers and mixtures thereof are included within the scope of the invention. Compounds of formula II may exist as regioisomers and may also exhibit tautomerism. All tautomeric forms and mixtures thereof are included within the scope of the invention.

Compounds of formula II may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

It will be appreciated that an effective amount of the compound of formula II, may be used to effect the dyeing and/or temporary tattooing of a subject. The term "effective amount" refers to an amount of a compound, which confers the desired colouring effect on the treated subject (e.g. sufficient to dye hair or temporarily tattoo skin). The effect may be objective (i.e. measurable by some test or marker) or subjective (i.e. the subject can see the difference).

For the avoidance of doubt, the terms "halo", "aryl", "alkyl", "cycloalkyl", and "heteroaryl" take the meanings described hereinbefore.

In embodiments of formula II that may be mentioned herein:

(a) $R^{13}$ represents H or $C_{6-10}$ alkyl, which latter group is unsubstituted or substituted with one or more substituents selected from unsubstituted $C_{1-3}$ alkyl;

(b) $R^{14}$ represents H, $C_{1-6}$ alkyl, $OC_{1-6}$ alkyl, or $C(O)$ $OC_{1-6}$ alkyl, which latter three groups are unsubstituted or substituted with one or more substituents selected from $C_{1-3}$ alkyl;

(c) wherein $R^{15a}$ to $R^{15c}$, $R^{16a}$ to $R^{16h}$, $R^{17a}$ to $R^{17h}$, $R^{18a}$ to $R^{18h}$, $R^{19a}$ to $R^{19c}$, $R^{20a}$ to $R^{20h}$, $R^{21a}$ to $R^{21h}$, $R^{22a}$ to $R^{22h}$, independently represent, at each occurrence when present, H, or $C_{1-6}$ alkyl.

Other compounds of formula II that may be mentioned include compounds of the examples described hereinafter. Thus, embodiments of the invention that may be mentioned per se include those in which the compound of formula II is a compound selected from the list:

(i) 4-2-((2-ethylhexyl)oxy)benzene-1,4-diamine;
(ii) hexyl-2,5-diaminobenzoate; and
(iii) ($N^1$-hexyl)(2-hexyloxy)-1,4-diaminobenzene Specific compounds of formula II that may be mentioned herein per se include:

wherein the compound of formula II is selected from the list:

(i) 4-2-((2-ethylhexyl)oxy)benzene-1,4-diamine; and
(iii) hexyl-2,5-diaminobenzoate.

Similarly, compounds of formula II that may be used in the method described hereinbefore may include those in which the compound of formula II is a compound selected from the list:

(i) 4-2-((2-ethylhexyl)oxy)benzene-1,4-diamine;
(ii) 2-hexyloxy-1,4-diaminobenzene;
(iii) hexyl-2,5-diaminobenzoate; and
(iv) ($N^1$-hexyl)(2-hexyloxy)-1,4-diaminobenzene.

Specific compounds of formula II that may be mentioned herein in association with the above-described method include:

(i) 4-2-((2-ethylhexyl)oxy)benzene-1,4-diamine; and
(ii) ($N^1$-hexyl)(2-hexyloxy)-1,4-diaminobenzene.

A compound of formula II that may be mentioned herein per se and in relation to the method is hexyl-2,5-diaminobenzoate.

It will be appreciated that the compounds of formula I and of formula II may be useful in a composition for dyeing hair or (temporarily) tattooing the skin. Thus, in a fifth aspect of the invention, there is disclosed a composition for dyeing hair or tattooing skin, comprising:

a compound of formula I as defined above, or a compound of formula II as defined above; and
water.

The term "temporary" in the context of tattoos in this invention is understood to mean a temporary colouring of the skin, which can be removed completely or nearly completely by washing (e.g. washing the tattoo with a soap) or by the natural shedding of the epidermis over a period of time.

In the context of the currently claimed invention, "dyeing hair" refers to the application of a formulation containing a compound of formula I or II to effect a permanent or semi-permanent colour change to the hair so dyed. This effect may be achieved without the presence of oxidative materials to blonde/bleach the hair and/or oxidise the compounds of formula I and II, though an oxidising material may be present in some embodiments described herein.

It will be appreciated that the compounds and compositions mentioned herein may be used for permanently dyeing hair. In which case, the effect is essentially permanent until the hair grows out or is dyed a different colour.

The composition may comprise from 0.0001 to 20 wt % of a compound of formula I or a compound of formula II, with the balance water. It will be appreciated that other components may form part of the composition, as discussed below, as such water is typically provided in an amount ranging from about 15% to about 99% by weight relative to the total weight of the composition. The pH range of the composition may be from about 1.0 to 14.0, though more typically, the pH range of the composition will be from about 3.0 to about 11.0. It will be appreciated that a combination of compounds of formula I, combinations of compounds of formula II and combinations of compounds of formula I and II are specifically contemplated herein. For the avoidance of doubt, reference to "compounds of formula I" and "compounds of formula II" also relates to physiologically acceptable salts or solvates, or an oxidised derivatives thereof.

It will be appreciated that the compositions discussed herein may comprise additional components, which additional components may include, but are not limited to, coupling agents, surfactants, additional diluents/solvents, thickening agents, and alkalinising agents.

Any suitable coupling agent that may be used with PPD may be used herein, with the coupling agent forming from 0.0001 to 20 wt % of the entire composition. Suitable coupling agents may be selected from the group including, but not limited to, phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include 3,4-methylenedioxyphenol, 3,4-methylenedioxy-1-[(beta-hydroxyethyl)amino]benzene, 1-methoxy-2-amino-4-[(beta-hydroxyethyl)amino]-benzene, 1-hydroxy-3-(dimethylamino)benzene, 6-methyl-1-hydroxy-3[(beta-hydroxyethyl)-amino]benzene, 2,4-dichloro-1-hydroxy-3-aminobenzene, 1-hydroxy-3-(diethylamino)-benzene, 1-hydroxy-2-methyl-3-amninobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diamino-benzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, and mixtures thereof. Specific coupling agents that may be mentioned herein include resorcinol, 1-naphthol, 5-amino-o-cresol, 2-methylresorcinol, m-aminophenol, m-phenylenediamine, 1-phenyl-3-methyl-pyrazol-5-one, their salts, or mixtures If the composition comprises a surfactant, the surfactant may be anionic, cationic, nonionic, zwitterionic or ampho-teric. It will be appreciated that one or more surfactants may form part of the composition. When present, the surfactant(s) may form from 0.01 to 20 wt % of the composition.

Suitable nonionic surfactants that may be mentioned herein include, but are not limited to, alkyl polyglycosides, cetomacrogol 1000, cetostearyl alcohol, cetyl alcohol, cocamide DEA, cocamide MEA, decyl glucoside, decyl polyglucose, ethoxylates, glycerol monostearate, IGEPAL CA-630, isoceteth-20, lauryl glucoside, maltosides, monolaurin, mycosubtilin, nonidet P-40, nonoxynols, octaethylene glycol monododecyl ether, N-octyl beta-D-thioglucopyranoside, octyl glucoside, oleyl alcohol, PEG-10 sunflower glycerides, pentaethylene glycol monododecyl ether, polidocanol, poloxamers, polyethoxylated tallow amine, polyglycerol polyricinoleate, polysorbates, sorbitan, sorbitan monolaurate, sorbitan monostearate, sorbitan tristearate, stearyl alcohol, surfactin, Triton X-100, and Tween 80.

Suitable cationic surfactants that may be mentioned herein include, but are not limited to, behentrimonium chloride, benzalkonium chloride, benzethonium chloride, benzododecinium bromide, bronidox, carbethopendecinium bromide, cetalkonium chloride, cetrimonium bromide, cetrimonium chloride, cetylpyridinium chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, octenidine dihydrochloride, olaflur, N-oleyl-1,3-propanediamine, pahutoxin, stearalkonium chloride, tetramethylammonium hydroxide, and thonzonium bromide.

Suitable zwitterionic surfactants that may be mentioned herein include, but are not limited to, betaines, N-alkyl-N, N-dimethylammonium glycinates, N-acylaminopropyl-N, N-dimethyl-ammonium glycinates, and 2-alkyl-3-carboxymethyl-3-hydroxyethyl imidazolines.

Suitable zwitterionic surfactants that may be mentioned herein include, but are not limited to, N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkyl aminopropionate, cocoacylaminoethyl aminopropionate, and $C_{12}$-$C_{18}$ acylsarcosine.

The compositions according to the present invention may include one or more solvents as additional diluent materials in addition to water. Generally, solvents suitable for use in the colouring compositions of the present invention are selected to be miscible with water and innocuous to the skin.

Solvents suitable for use as additional diluents herein include $C_1$-$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. These additional diluents/solvents may be present in an amount of from about 0.5% to about 20% by weight of the total composition.

Depending on the selected application, the composition's viscosity may need to be adjusted viscosity. For example, this may be to meet consumer expectations or for functional reasons (e.g. to make the composition more easy to handle for specific applications). This generally occurs through the use of one or more thickening agents. Any suitable thickening agent, such as organic and inorganic thickening agents may be used.

Suitable thickening agents include are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions, and derivatives such as amylose, amylopectin, and dextrins, as well as cellulose derivatives (which are different from the celluloses of the invention) such as, for example, methylcellulose, carboxyalkylcelluloses, and hydroxyalkylcelluloses; nonionic, fully synthetic polymers such as polyvinyl alcohol or polyvinylpyrrolidinone; as well as inorganic thickeners, in particular phyllosilicates such as, for example, bentonite, in particular smectites, such as montmorillonite or hectorite. It will be appreciated that one or more of the above thickening agents may be used in the compositions described herein.

In compositions described herein, the thickening agents may be used in a total amount of from 0.1 to 4.5% by weight, such as from 0.15 to 3.5% by weight, such as from 0.2 to 2.0% by weight, based on the total weight of the composition.

The composition may have a pH range of from 7.0-10.0 (e.g. from 9.5 to 10.0). If the composition does not have a pH within the desired pH range for the application in question, then the pH may be adjusted by the addition of one or more alkalinising agents. Suitable alkalinising agents that can be used to adjust the desired pH value can be selected from the group formed by ammonia, alkanolamines, basic amino acids, and inorganic alkalinizing agents such as alkali (alkaline earth) metal hydroxides, alkali (alkaline earth) metal metasilicates, alkali (alkaline earth) metal phosphates, and alkali (alkaline earth) metal hydrogen phosphates. For example, the alkalinising agent may be $Na_2CO_3$.

If the pH is too alkaline, it will be appreciated that the composition may further comprise one or more acids to adjust the pH value. Suitable acids are, for example, organic acids such as alpha-hydroxycarboxylic acids or inorganic acids.

Further, the compositions described above may also include other active substances, auxiliary substances, and additives such as, for example, linear cationic polymers such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidinone copolymers quaternized with diethyl sulfate, vinylpyrrolidone-imidazolinium-methochloride copolymers, and quaternized polyvinyl alcohol; zwitterionic and amphoteric polymers; anionic polymers such as, for example, polyacrylic acids or crosslinked polyacrylic acids; structurants such as glucose, maleic acid, and lactic acid, hair-conditioning compounds such as phospholipids, for example, lecithin and kephalins; perfume oils, dimethyl isosorbide, and cyclodextrins; fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; light stabilizers and UV blockers; active substances such as panthenol, pantothenic acid, pantolactone, allantoin, pyrrolidinone carboxylic acids and salts thereof, as well as bisabolol; polyphenols, particularly hydroxycinnamic acids, 6,7-dihydroxycoumarins, hydroxybenzoic acids, catechins, tannins, leukoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ethers, carbonates, hydrogen carbonates, guanidines, ureas, and primary, secondary, and tertiary phosphates; opacifiers such as latex, styrene/PVP and styrene/acrylamide copolymers, and PEG-3 distearate; propellants such as propane-butane mixtures, $N_2O$, dimethyl ether, $CO_2$, and air.

The selection of these additional substances is made by the skilled artisan according to the desired properties of the composition in question. In regard to other facultative components and the employed amounts of said components, reference is made expressly to relevant handbooks known to the skilled artisan. The additional active and auxiliary substances are used in the agents of the invention preferably in each case in amounts of 0.0001 to 25% by weight, in particular of 0.0005 to 15% by weight, based on the total weight of the composition in question.

The compositions disclosed herein may be produced, for example, in the form of a lotion, a gel, a spray, an aerosol, or a pump foam. Depending on the application form, they are therefore preferably filled into a tube, a container, a bottle, a box, a pressurized container, or into a container with a pump spray applicator.

In certain embodiments, the composition disclosed above may contain oxidised derivatives of the compounds of formula I or II. In which case, there may be no need to provide a separate oxidizing agent. While compositions where the compounds of formula I or II are in an unoxidized form may be used as is—and provide at least temporary hair dyeing effects. It is also contemplated that an oxidizing agent may also be included into the composition (or applied separately) in order to blonde the hair and provide a more consistent colouration, which may be permanent. Thus, in a sixth aspect of the invention, there is provided a kit of parts comprising:

(i) a composition as described above; and
(ii) a developing composition comprising an oxidising agent.

It will be appreciated that the composition described above preferably contains unoxidised forms of the compounds of formula I and II, though oxidised forms of the compounds of formula I and II may also be used.

In general, the compositions comprising the compounds of formula I or II described above may be used in these kits of parts. As such, reference to the above description of these compositions is made here.

The developing composition is added to a composition comprising the compounds of formula I or II in order to provide a blonding/bleaching effect on hair and, possibly, to cause oxidation of the compounds of formula I or II (if in an non-oxidised form). The developing composition may use any suitable oxidizing agent that is safe for use on skin and hair. A suitable oxidising agent that may be mentioned herein is hydrogen peroxide. The oxidising agent may be provided in a suitable amount that falls within regularoty guidelines. As such, in accordance with the Cosmetic Directive of the European Union (Council Directive of 27 Jul. 1976 r. Annex III p. 12), the maximum permitted concentration in a ready-to-use hair dye is 12% (40 volumes) and 4 wt % in skin-care preparations. It will be appreciated that the kit of parts mentioned here is intended for use in hair dye compositions, as such the oxidising agent may be present in an amount of from 0.5 to 45 wt % in the developer composition, with the balance being water.

In further embodiments of the invention, the developer composition may further comprise a surfactant, a thickening agent, and an acidifying agent.

When present in the developer composition, one or more surfactants may be selected from those mentioned hereinbefore. The surfactant(s) may be present in an amount of from 0.01 to 20 wt % of the developer composition.

When present in the developer composition, one or more thickening agents may be selected from those mentioned hereinbefore. The thickening agent(s) may be present in an amount of from 0.01 to 20 wt % of the developer composition.

The developer composition may have a pH range of from 2.5-6.9. If the developer composition does not have a pH within the desired pH range for the application in question, then the pH may be adjusted by the addition of one or more acidifying agents. Suitable acidifying agents include, for example, organic acids such as alpha-hydroxycarboxylic acids or inorganic acids.

Further, the developer compositions may also include other active substances, auxiliary substances, and additives, as described hereinbefore.

When used in hair dyeing, the hair dyeing method may have three steps:
- the first step requires contacting a subject's hair with the "composition" (upon optional mixing with a developer (e.g. a composition comprising an oxidizing agent));
- allowing the mixture to remain in the hair for a period of about 30 seconds to about 60 minutes; and
- then washing the hair extensively with water and surfactant-containing shampoos leaving the long-lasting hair colour change.

A temporary tattoo using compositions described herein, may be applied in a manner similar to henna tattoos to the skin of a subject.

The invention will be further described in connection with the following examples, which are set forth for the purposes of illustration only.

EXPERIMENTAL

General

All common reagents used were obtained from commercial suppliers and were used without further purification. NMR spectra were recorded using Bruker Avance 500 (AV500), Bruker Avance 300 (AV300) and Bruker Avance 400 (DRX400) NMR spectrometers.

Materials and Methods:

Reagents, Standards and Other Chemicals p-Phenylenediamine (99%) and 2 amino-5-nitro-pyridine (ANP) were purchased from Sigma-Aldrich.

Formic acid (98%) was purchased from Fluka Chemie (GmbH). Acetonitrile (99.9%) and ammonium hydroxide (30%), methylene chloride and methanol (99.9%) were purchased from Merck.

The test chemicals, with mentioned purity and CAS numbers, were purchased from Sigma Aldrich Chemical Company (Singapore): 1,4-phenylenediamine, 100% [106-50-3]; p-benzoquinone, 98% [106-51-4]; Deferoxamine mesylate, and DL-dithiothreitol. The cysteine peptide (Ac-RFAACAA-COOH) 100% [106-50-3]; and lysine peptide (Ac-RFAAKAA-COOH) 100% [106-50-3]; were purchased and purified by the Peptide 2.0 Inc (Chantilly, Va.). Leucine enkephalin internal standard was purchased from Sigma Aldrich Chemical Company (Singapore). The test chemical p-phenylenediamine (99%), was purchase from Sigma Aldrich Chemical Company (Singapore). Acetonitrile (99.9%) and methanol (99.9%) were purchased from Merck.

Instrumentation

An Agilent 1290 Infinity ultra-high pressure liquid chromatography (UHPLC) binary pump, autosampler, vacuum degasser, and column oven (Agilent Technologies Inc., Santa Clara, Calif., USA) and ACQUITY UPLC BEH C18, 1.7 µM, 2.1×100 mm column (Waters, Mildord, Mass., USA), were used for chromatographic separations. The mass spectrometric analysis was performed by use of an AB SCIEX QTRAP 5500 tandem mass spectrometry (MS/MS) system (AB SCIEX, Framingham, Mass., USA) operating in triple quadrupole positive mode (ESI+) equipped with an AB Sciex Turbo Ion Spray interface. Acquisition and analysis of data were performed with Analyst software ver. 1.6.2 (Applied Biosystems).

High Performance Liquid Chromatography

The analytical column was maintained at 40° C. A mobile phase gradient pumped at 0.4 mL/min was used to elute the analytes from the column. Mobile phase A consisted of 0.1% formic acid in acetonitrile. Mobile phase B consisted of 0.1% formic acid in Milli-Q water. The initial gradient of 90% B was maintained for 2 min, reduced to 70% B over 1 min, maintained for 4.0 min and increased to 90% B over 0.5 min. The column was equilibrated for 1 min resulting in a total run time of 5 min. The injection volume was 5.0 µL.

Tandem Mass Spectrometry

Analytes and IS were detected on a triple quadrupole mass spectrometer operating in the positive mode (ESI+) with multiple reaction monitoring (MRM). The abundant fragment for each analyte was selected by performing enhanced product ion (EPI) scans of the internal standard (IS) during an infusion analysis at a constant flow rate of 20 µL/min. For each compound, two mass fragments were monitored with one fragment used for quantification and the other fragment used for the additional confirmation of identity.

General Procedure 1

The procedure below was used for the synthesis of certain nitro compounds mentioned herein.

Triethyl amine (1.5 equivalent) was added to a DMSO (7 mL) solution of the equimolar mixture of 1-Fluoro-4-nitrobenzene and C-substituted PPD derivatives under inert atmosphere. After 24 hours of stirring at 90° C., reaction mixture was cooled and poured into water to induce precipitation. The sticky precipitate was extracted with ethyl acetate and the organic layer was washed thoroughly with water and brine solution. Evaporation of solvent afforded the crude product as red liquid which was purified by silica gel column chromatography.

General Procedure 2

The procedure below was used for the reduction of certain nitro compounds mentioned herein to provide desired final products.

Excess tin(II) chloride was added to an ethanolic solution of a nitro derivative under an inert atmosphere. Concentrated HCl (2.5 mL) was added and the mixture was refluxed for 24 hours. The resulting mixture was poured into ice-water mixture and the pH of the mixture was set at 12 with 20% aqueous NaOH solution. Mixture was extracted with ethyl acetate and the organic layer was quickly washed with water and finally with brine solution. After solvent evaporation residue was dried under vacuum to get the title compound.

General Procedure 3

This procedure relates to the formation of di-imines from 4,4'-diaminodiphenylamine.

Aldehyde (1.1 mmol) was added to an ethanolic suspension of 4,4'-diaminodiphenylamine (1 mmol). Resulting mixture was stirred at room temperature for the time mentioned for the corresponding aldehyde. Resulting crystalline precipitate was filtered and washed with a 1:1 mixture of ethanol and diethyl ether and then finally with diethyl ether. Drying under suction afforded the desired product as crystalline solid. Pure imine was obtained by the recrystallization from a mixture of dichloromethane and hexane.

General Procedure 4

This procedure relates to the formation of di-amines from di-imines

The imine (1 mmol) was dissolved in 12 mL of dry THF in a two-necked round bottom flask under nitrogen atmosphere. To the solution excess sodium borohydride (4 mmol) was added and the mixture was stirred at room temperature for 24 hours. Excess water was added to quench the reaction as well as to quench any unreacted sodium borohydride. THF was removed under vacuum and the residue was extracted with dichloromethane. The DCM extract was washed thrice with water and then with brine solution. After drying over anhydrous $Na_2SO_4$ and removal of solvent in vacuo the desired amines were provided as a crystalline solid.

Example 1

Synthesis of PPD Derivative 1: 4,4'-Diaminodiphenylamine (2)

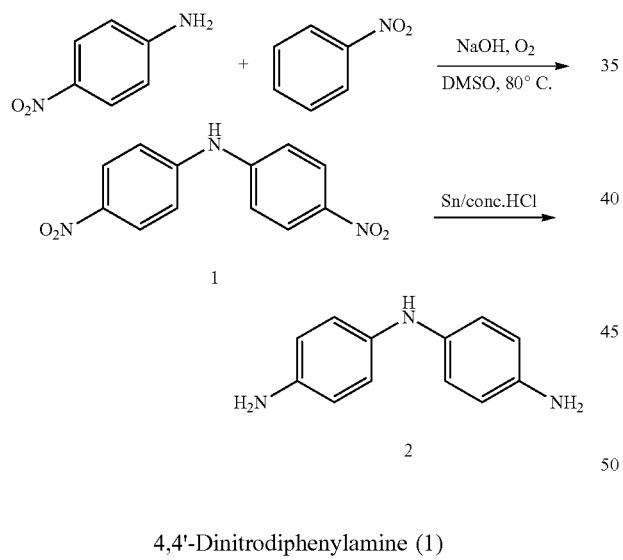

4,4'-Dinitrodiphenylamine (1)

Solid sodium hydroxide (1.65 g, 41 mmol) was added to a DMSO solution of p-nitroaniline (1.4 g, 10 mmol). To the greenish brown mixture, nitrobenzene (3.8 mL, 37 mmol) was added dropwise and the mixture was stirred at 80° C. temperature for 12 hours with a slow stream of air bubbling through. After complete consumption of nitrobenzene, as evident from TLC analysis, the reaction mixture was cooled to room temperature and was added dropwise to water with vigorous stirring, which resulted in a yellow precipitate. The precipitate was collected by filtration, washed thoroughly with water to remove traces of NaOH and then with hexane to remove excess nitrobenzene. The precipitate was dissolved in minimum amount of DCM/acetone mixture and added dropwise to hexane with vigorous stirring. Yellow precipitate was filtered, washed with hexane and dried under suction to provide 2 g of pure product.

$^1$H NMR (500 MHz, DMSO-d6): δ 9.98 (1H, s, amine), 8.21 (4H, d, J=9 Hz), 7.36 (4H, d, J=9 Hz). $^{13}$C NMR (125 MHz, DMSO-d6): δ 147.6, 140.5, 125.8, 117.1.

4,4'-Diaminodiphenylamine (2)

4,4'-Dinitrodiphenylamine (1 g, 3.86 mmol) was suspended in 20 mL of concentrated hydrochloric acid under a nitrogen atmosphere. Fine tin powder (2.46 g, 20.72 mmol) was added portion-wise to the reaction mixture. After complete addition of tin, the reaction mixture was refluxed for 18 hours. The reaction mixture was then cooled to room temperature and diluted with 50 mL of water and the pH of the mixture was adjusted to 12 by dropwise addition of 20% aqueous NaOH solution. A greyish white precipitate formed, which was filtered and washed with water to remove traces of NaOH. After prolonged drying under vacuum, the product was collected as a greyish white powder (0.6 g). Alternatively, the product can be extracted from the alkaline mixture with ethyl acetate, with the organic solvent them being dried ($MgSO_4$) and removed under vacuum to afford the product.

$^1$H NMR (500 MHz, DMSO-d6): δ 6.76 (1H, s, secondary amine), 6.64 (4H, d, J=8 Hz), 6.45 (4H, d, J=8 Hz), 4.48 (4H, s, primary amine). $^{13}$C NMR (125 MHz, DMSO-d6): δ 141.4, 135.6, 118.4, 115.0.

The secondary amine proton in 1 resonates at δ 9.98 ppm, a significantly upfield shift (Δδ 3.22 ppm) of the secondary amine proton was observed in the 1H NMR spectra of 4,4'-Diaminodiphenylamine (2). The amine signals were unambiguously assigned by deuterium exchange experiment.

Example 2

Synthesis of PPD Derivative 2: $N^1,N^4$-bis(4-aminophenyl)-1,4-benzenediamine (4)

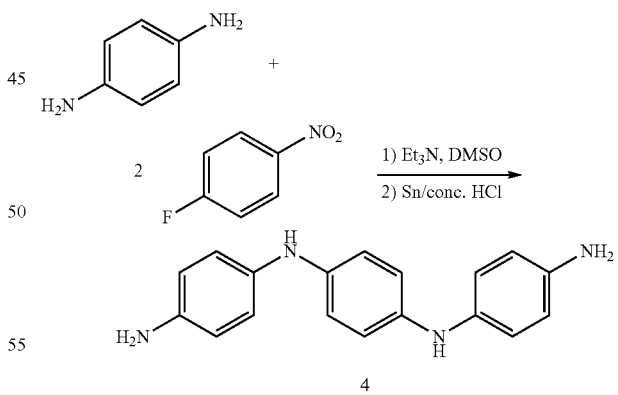

$N^1,N^4$-bis(4-nitrophenyl)-1,4-benzenediamine (3)

1-Fluoro-4-nitrobenzene (2.2 mL, 20.7 mmol) and triethylamine (3 mL, 21.5 mmol) was added successively to 20 ml DMSO solution of p-phenylenediamine (1.08 g, 10 mmol) under inert atmosphere. The dark red solution was stirred at 90° C. for three days, after which the mixture was cooled to room temperature and was dropwise added to 200 ml of chilled water with vigorous stirring. Dark brown precipitate was collected by filtration and washed thoroughly with distilled water. Drying under suction afforded the crude product which was purified by silica gel column chromatography using 20% acetone/DCM mixture as eluent. Alternatively, the title compound can be isolated by washing the crude mixture with 70% DCM/hexane mixture. Yield: 1.12 g (40%).

$^1$H NMR (500 MHz, DMSO-d6): δ 9.31 (s, 2H, secondary amine), 8.10 (d, J=9.3, 4H), 7.28 (s, 4H), 7.04 (d, J=9.3, 4H). $^{13}$C NMR (125 MHz, DMSO-d6): δ 148.1, 141.0, 126.4, 117.6.

N$^1$,N$^4$-bis(4-aminophenyl)-1,4-benzenediamine (4)

This compound was synthesized by the reduction of corresponding dinitro compound 3 (0.6 g, 1.71 mmol) with tin powder (2 g, 16 mmol) by following the method described for the synthesis of 4,4'-Diaminodiphenylamine. Yield: 0.3 g (61%).

$^1$H NMR (500 MHz, DMSO-d6): δ 7.01 (s, 2H), 6.72 (d, J=4.6, 8H), 6.48 (d, J=8.3, 4H), 4.58 (s, 2H). $^{13}$C NMR (125 MHz, DMSO-d6): δ 142.1, 138.0, 134.3, 119.6, 117.0, 114.9.

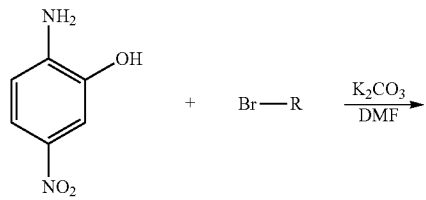

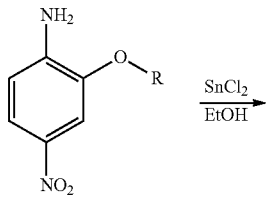

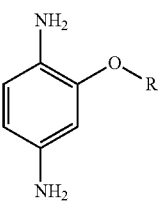

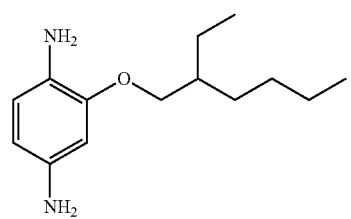

5
R = hexan-2-(ethyl)-yl

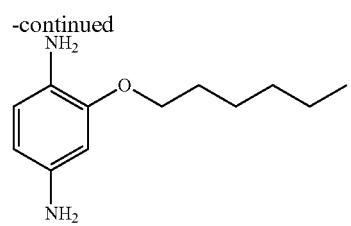

6
R = hexan-2-yl

Example 3

Synthesis of PPD Derivative 3:
2-((2-ethylhexyl)oxy)benzene-1,4-diamine (5)

Synthesis of 2-(2-ethylhexyloxy)-4-nitroaniline 2-amino-5-nitrophenol (1.54 g, 10 mmol) was dissolved in 20 mL of DMF kept under an inert atmosphere and 1.39 g (10 mmol) of K$_2$CO$_3$ was added to the stirring solution. After five minutes of stirring at room temperature, 1-bromo-2-ethylhexane (2.3 ml, 12.93 mmol) was added. Resulting red mixture was refluxed for 18 hours. The dark brown mixture was added dropwise to saturated NaHCO$_3$ solution with vigorous stirring. After 30 minutes the mixture was extracted with DCM and the organic layer was washed 3 times with NaHCO$_3$ solution, 3 times with saturated LiCl solution and finally with brine solution. After drying over anhydrous Na$_2$SO$_4$, solvent was removed under reduced pressure and dried in vacuo. The title compound was isolated as yellowish-green viscous liquid. Yield: 0.8 g (52%).

$^1$H NMR (300 MHz, DMSO) δ 7.72 (dd, J=8.8 Hz, 2.2 Hz, 1H), 7.57 (d, J=2.3 Hz, 1H), 6.67 (d, J=8.8 Hz, 1H), 6.30 (s, 2H), 3.94 (d, J=5.3 Hz, 2H), 1.74 (dt, J=12.0 Hz, 5.9 Hz, 1H), 1.53-1.38 (m, 4H), 1.33-1.26 (m, 4H), 0.92-0.85 (m, 6H). $^{13}$C NMR (75 MHz, DMSO) δ 146.3, 144.3, 136.1, 119.8, 111.2, 106.5, 70.9, 30.1, 28.8, 23.6, 22.8, 14.3, 11.2.

PPD Derivative 3:
2-((2-ethylhexyl)oxy)benzene-1,4-diamine (5)

Excess tin(II) chloride (7.14 g, 37 mmol) was added to an ethanolic solution of 1.31 g (5.5 mmol) of 2-(2-ethylhexyloxy)-4-nitroaniline under inert atmosphere. Concentrated HCl (2.5 mL) was added and the mixture was refluxed for 24 hours. The resulting white cloudy mixture was poured into an ice-water mixture and the pH of the mixture was adjusted to 12 by adding 20% aqueous NaOH solution. The mixture was extracted with ethyl acetate and the organic layer was quickly washed with water and finally with brine solution. After solvent evaporation, the residue was dried under vacuum to provide the title compound.

Yield: 0.6 g (82%). $^1$H NMR (300 MHz, DMSO) δ 7.72 (dd, J=8.8 Hz, 2.2 Hz, 1H), 7.57 (d, J=2.3 Hz, 1H), 6.67 (d, J=8.8 Hz, 1H), 6.30 (s, 4H), 3.94 (d, J=5.3 Hz, 2H), 1.74 (dt, J=12.0 Hz, 5.9 Hz, 1H), 1.53-1.38 (m, 4H), 1.33-1.26 (m, 4H), 0.92-0.85 (m, 6H). 13C NMR (75 MHz, DMSO) δ 146.3, 144.3, 136.1, 119.8, 111.2, 106.5, 70.9, 30.1, 28.8, 23.6, 22.8, 14.3, 11.2.

Example 4

Synthesis of PPD Derivative 4: 2-hexyloxy-1,4-diaminobenzene (6)

Synthesis of 2-hexyloxy-4-nitroaniline

2-Amino-5-nitrophenol (3.083 g, 20.4 mmol) was dissolved in 10 mL of DMF kept under an inert atmosphere. 1-Bromohexane (2.8 ml, 20 mmol) and $K_2CO_3$ (2.83 g 20.5 mmol) were added to the solution. The resulting red mixture was refluxed for 18 hours after which, the resulting dark brown mixture was added dropwise to saturated $NaHCO_3$ solution with vigorous stirring. After 30 minutes, the mixture was extracted with DCM and the organic layer was washed 3 times with $NaHCO_3$ solution, 3 times with saturated LiCl solution and finally with brine solution. After drying over anhydrous $Na_2SO_4$, the solvent was removed under reduced pressure and the resulting mixture oil dried in vacuo. The oily mixture was then purified by gradient column chromatography with ethyl acetate and hexane mixture as eluent. The title compound was eluted with 50% ethyl acetate and hexane mixture and solvent evaporation afforded the product as a bright yellow solid.

Yield: 3.2 g (96.2%). $^1$H NMR (300 MHz, DMSO) δ 7.72 (dd, J=8.8 Hz, 2.4 Hz, 1H), 7.55 (d, J=2.4 Hz, 1H), 6.66 (d, J=8.8 Hz, 1H), 6.34 (s, 2H), 4.04 (t, J=6.4 Hz, 2H), 1.75 (quintet, J=7 Hz, 2H), 1.52-1.39 (m, 2H), 1.31 (m, 4H), 0.88 (t, J=6.9 Hz, 3H). $^{13}$C NMR (75 MHz, DMSO) δ 146.4, 144.2, 136.0, 119.9, 111.2, 106.7, 68.6, 31.4, 28.8, 25.4, 22.4, 14.2

PPD Derivative 4: 2-hexyloxy-1,4-diaminobenzene (6)

A similar synthetic protocol to that to make (5) was used to synthesize the title compound except that excess tin(II) chloride (7.14 g, 37 mmol) was added to an ethanolic solution of 1.31 g (5.5 mmol) of 2-hexyloxy-4-nitroaniline under inert atmosphere.

Yield: 0.6 g (84%). $^1$H NMR (300 MHz, DMSO) δ 6.40 (d, J=8.1 Hz, 1H), 6.20 (d, J=2.1 Hz, 1H), 6.00 (dd, J=8.1 Hz, 2.1 Hz, 1H), 4.04 (s, 4H), 3.84 (t, J=6.4 Hz, 2H), 1.77-1.65 (m, 2H), 1.50-1.38 (m, 2H), 1.32 (m, 4H), 0.90 (t, J=6.7 Hz, 3H). $^{13}$C NMR (75 MHz, DMSO) δ 147.1, 140.3, 128.0, 115.7, 106.9, 100.8, 67.8, 31.4, 29.3, 25.7, 22.5, 14.2.

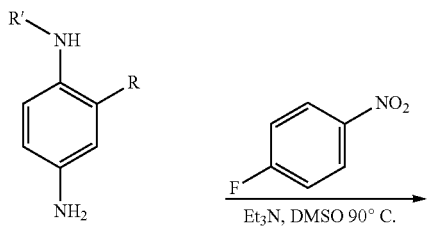

8: R = OC$_6$H$_{13}$; R' = H
9: R = COOC$_6$H$_{13}$; R' = H
10: R = OC$_6$H$_{13}$; R' = C$_6$H$_{13}$

Et$_3$N, DMSO 90° C.

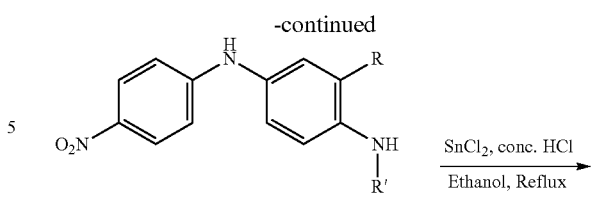

11: R = OC$_6$H$_{13}$; R' = H
12: R = COOC$_6$H$_{13}$; R' = H
13: R = OC$_6$H$_{13}$; R' = C$_6$H$_{13}$

SnCl$_2$, conc. HCl
Ethanol, Reflux

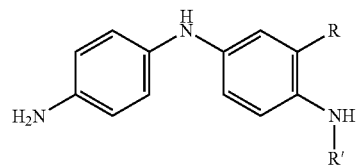

14: R = OC$_6$H$_{13}$; R' = H
15: R = COOC$_6$H$_{13}$; R' = H
16: R = OC$_6$H$_{13}$; R' = C$_6$H$_{13}$

Example 5

Synthesis of PPD Derivative 5: 4-Amino-(3-hexyloxy)-4'-aminodiphenylamine (14)

4-Amino-(3-hexyloxy)-4'-nitrodiphenylamine (11)

Obtained using General Procedure 1 using 1-Fluoro-4-nitrobenzene and 2-hexyloxy-1,4-diaminobenzene (6).

Yield: 0.89 g (89%). $^1$H NMR (300 MHz, DMSO) δ 8.94 (s, 1H), 8.00 (d, J=9.2, 2H), 6.81 (d, J=9.3, 2H), 6.71-6.64 (m, 2H), 6.59 (dd, J=8.3, 1.9, 1H), 4.66 (s, 2H), 3.92 (t, J=6.4, 2H), 1.77-1.67 (m, 2H), 1.42 (dd, J=13.2, 6.0, 2H), 1.34-1.26 (m, 4H), 0.87 (t, J=6.8, 3H). $^{13}$C NMR (75 MHz, DMSO) δ 153.3, 146.3, 136.8, 135.9, 128.8, 126.6, 116.4, 114.3, 112.3, 108.3, 68.2, 31.4, 29.1, 25.6, 22.4, 14.2.

PPD Derivative 5: 4-Amino-(3-hexyloxy)-4'-aminodiphenylamine (14)

The title compound was synthesized by the reduction of 4-Amino-(3-hexyloxy)-4'-nitrodiphenylamine (11) using General Procedure 2.

Yield: 0.85 g (85%). $^1$H NMR (400 MHz, DMSO) δ 6.82 (s, 1H), 6.69 (d, J=8.3, 2H), 6.47 (dd, J=18.3, 9.9, 4H), 6.28 (d, J=7.2, 1H), 4.51 (s, 2H), 4.09 (s, 2H), 3.84 (t, J=6.3, 2H), 1.75-1.66 (m, 2H), 1.46-1.38 (m, 2H), 1.32 (dd, J=9.6, 5.9, 4H), 0.89 (t, J=6.6, 3H). $^{13}$C NMR (75 MHz, DMSO) δ 146.8, 142.1, 137.1, 135.4, 130.4, 119.4, 115.3, 115.2, 109.4, 103.0, 67.0, 31.4, 29.2, 25.6, 22.4, 21.1, 14.5.

Example 6

Synthesis of PPD Derivative 6: Hexyl [2-amino-5-(4-nitrophenylamino)]benzoate (15)

Hexyl [2-amino-5-(4-nitrophenylamino)]benzoate (12)

Obtained using General Procedure 1 using 1-fluoro-4-nitrobenzene (0.12 mL; 1.13 mmol) and hexyl 2,5-diaminobenzoate (0.22 g, 0.93 mmol). Crude product was purified by gradient column chromatography using dcm/hexane mixture and the title compound eluted with 30% dcm/hexane.

Yield: 0.2 g (60%). $^1$H NMR (400 MHz, DMSO) δ 8.97 (s, 1H), 8.02 (d, J=9.2, 2H), 7.55 (d, J=2.3, 1H), 7.20 (dd, J=8.7, 2.4, 1H), 6.85 (d, J=8.8, 1H), 6.78 (d, J=9.2, 2H), 6.66 (s, 2H), 4.20 (t, J=6.5, 2H), 1.71-1.62 (m, 2H), 1.36 (mm 2H), 1.31-1.24 (m, 4H), 0.84 (t, J=6.7, 3H). $^{13}$C NMR (75 MHz, DMSO) δ 167.3, 153.1, 149.3, 137.2, 131.0, 127.3, 126.6, 125.3, 118.1, 112.3, 109.4, 64.4, 31.2, 28.5, 25.6, 22.3, 14.1.

PPD Derivative 6: hexyl 2-amino-5-((4-aminophenyl)amino)benzoate (15)

The title compound was synthesized from the reduction of Hexyl [2-amino-5-(4-nitrophenylamino)]benzoate (12) using General Procedure 2.

$^1$H NMR (400 MHz, DMSO) δ 7.32 (d, J=2.7, 1H), 7.00-6.91 (m, 2H), 6.72-6.62 (m, 3H), 6.52-6.43 (m, 2H), 6.13 (s, 2H), 4.57 (s, 2H), 4.18 (t, J=6.5, 2H), 1.69-1.60 (m, 2H), 1.40-1.34 (m, 2H), 1.32-1.27 (m, 4H), 0.87 (t, J=6.9, 3H). $^{13}$C NMR (75 MHz, DMSO) δ 167.8, 145.2, 142.2, 135.1, 125.9, 119.4, 118.0, 117.1, 115.4, 109.7, 64.0, 31.2, 28.5, 25.5, 22.3, 14.2.

Example 7

Synthesis of PPD Derivative 7: 4-hexylamino-(3-hexyloxy)-4'-aminodiphenylamine (16)

4-hexylamino-(3-hexyloxy)-4'-nitrodiphenylamine (13)

Obtained using General Procedure 1 using 1-Fluoro-4-nitrobenzene and 2-hexyloxy-1,4-diaminobenzene (6).

$^1$H NMR (300 MHz, DMSO) δ 8.97 (s, 1H), 8.00 (d, J=9.2, 2H), 6.81 (d, J=9.3, 2H), 6.68 (d, J=6.6, 2H), 6.53 (d, J=8.9, 1H), 4.55 (t, J=5.9, 1H), 3.94 (t, J=6.4, 2H), 3.07 (dd, J=13.1, 6.6, 2H), 1.78-1.67 (m, 2H), 1.55 (dd, J=13.9, 7.0, 2H), 1.48-1.38 (m, 2H), 1.36-1.25 (m, 10H), 0.87 (t, J=6.9, 6H). $^{13}$C NMR (75 MHz, DMSO) δ 153.3, 146.3, 136.9, 136.4, 128.2, 126.6, 116.4, 112.3, 109.6, 107.7, 68.3, 43.3, 31.5, 31.4, 29.1, 29.0, 26.6, 25.6, 22.5, 22.4, 14.21, 14.20.

PPD Derivative 7: 4-hexylamino-(3-hexyloxy)-4'-aminodiphenylamine (16) was Synthesized from the Reduction of 4-hexylamino-(3-hexyloxy)-4'-nitrodiphenylamine (13)

$^1$H NMR (400 MHz, DMSO) δ 6.85 (s, 1H), 6.70 (d, J=7.6, 2H), 6.51-6.43 (m, 3H), 6.43-6.32 (m, 2H), 4.54 (s, 2H), 3.86 (t, J=6.0, 2H), 2.98 (br, 2H), 1.75-1.66 (m, 2H), 1.52 (dd, J=13.6, 6.8, 2H), 1.48-1.38 (m, 2H), 1.32 (d, J=16.0, 10H), 0.88 (d, J=3.7, 6H).

Example 8

Synthesis of PPD Derivative 8: 4,4'-Bis[(4-aminophenyl)amino]diphenylamine (17)

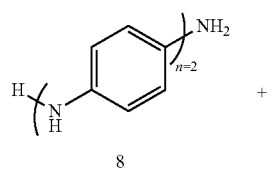

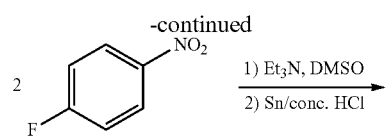

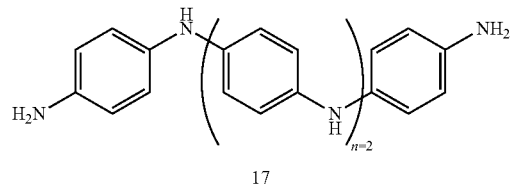

4,4'-Bis[(4-nitrophenyl)amino]diphenylamine

1-Fluoro-4-nitrobenzene (0.8 mL, 7.5 mmol) and triethylamine (1 mL, 7.2 mmol) was added to 7 ml DMSO solution of 4,4'-Diaminodiphenylamine (0.497 g, 2.5 mmol) under an inert atmosphere. The dark red solution was stirred at 90° C. for three days, after which the mixture was cooled to room temperature and was dropwise added to 200 ml of chilled water with vigorous stirring. A dark brown sticky precipitate was extracted with methanol and the supernatant with DCM. Combined extract was evaporated to dryness and the black sticky residue was dissolved in DMF and triturated with a 1:1 mixture of Et$_2$O and hexane to remove excess 1-Fluoro-4-nitrobenzene. Further repeated trituration from DCM and hexane afforded the title compound as dark brown crystalline solid.

Yield: 0.96 g (87%). $^1$H NMR (500 MHz, DMSO-d6): δ 9.13 (s, 2H), 8.23 (s, 1H), 8.06 (d, J=9.3, 4H), 7.14 (q, J=8.9, 8H), 6.92 (d, J=9.3, 4H). $^{13}$C NMR (75 MHz, DMSO-d6): δ 152.0, 140.3, 137.0, 131.7, 126.2, 123.6, 117.6, 112.3.

PPD Derivative 8: 4,4'-Bis[(4-aminophenyl)amino]diphenylamine (17)

This compound was synthesized by the reduction of corresponding dinitro compound (0.5 g, 1.14 mmol) with tin powder (0.667 g, 5.7 mmol) by following the method described in General Procedure 2.

Yield: 0.22 g (50%). $^1$H NMR (400 MHz, DMSO-d6): δ 7.20 (s, 1H), 7.06 (s, 2H), 6.81-6.74 (m, 12H), 6.50 (d, J=8 Hz, 4H) 4.59 (s, 4H). $^{13}$C NMR (75 MHz, DMSO-d6): δ 142.1, 138.0, 134.3, 119.6, 117.0, 114.9.

Example 9

Synthesis of PPD Derivative 9: 4-Amino-4'-[(4-tolylaminomethyl)phenyl]diphenylamine (24)

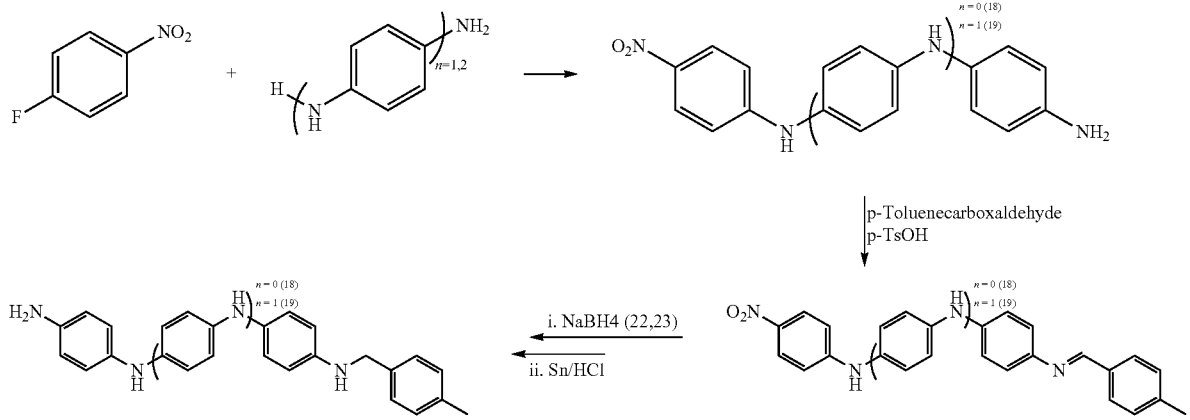

4-Amino-4'-nitrodiphenylamine (18)

Excess potassium carbonate (2.8 g, 20 mmol) was added to a DMSO (10 mL) solution of p-phenylenediamine (1.087 g, 10 mmol) and 1-Fluoro-4-nitrobenzene (1.1 mL, 10.4 mmol) kept under inert atmosphere. The dark red solution was stirred at 90° C. for 24 hours, after which the mixture was cooled to room temperature and was dropwise added to 200 ml of chilled water with vigorous stirring. Resulting red precipitate was collected by filtration. Washing of the filter cake with water and drying under suction afforded the crude product which was purified by silica gel column chromatography. The title compound was eluted with 5% ethyl acetate/DCM mixture.

Yield: 1 g (43%). $^1$HNMR (300 MHz, DMSO-d6): δ 8.88 (s, 1H), 8.00 (d, J=9.2, 2H), 6.92 (d, J=8.5, 2H), 6.76 (d, J=9.2, 2H), 6.61 (d, J=8.5, 2H), 5.08 (s, 2H). $^{13}$C NMR (75 MHz, DMSO-d6): δ153.1, 146.3, 136.4, 127.8, 126.3, 124.7, 114.5, 111.7.

Toluene Imine (20)

p-Toluenecarboxaldehyde (0.36 mL, 3 mmol) and catalytic amount of p-toluenesulphonic acid was added to an ethanolic solution (10 mL) of 4-amino-4'-nitrodiphenylamine (0.682 g, 2.97 mmol) and the mixture was stirred overnight at room temperature under nitrogen atmosphere. Resulting orange precipitate was collected by filtration washed with 20 mL of 20% ethanol/hexane mixture and finally with hexane. Drying over suction afforded pure crystalline solid.

Yield: 0.97 g (98%). $^1$H NMR (300 MHz, DMSO-d6): 9.37 (s, 1H), 8.62 (s, 1H), 8.10 (d, J=9.0, 2H), 7.83 (d, J=7.9, 2H) 7.36-7.26 (m, 6H). 7.07 (d. J=9.1, 2H). 2.38 (s, 3H), $^{13}$C NMR (75 MHz, DMSO-d6): δ 159.1, 150.6, 146.6, 141.3, 138.1, 137.9, 133.6, 129.3, 128.5, 126.1, 122.2, 121.5, 113.4, 21.1.

4-Nitro-4'-[(4-tolylaminomethyl)phenyl]diphenylamine (22)

Excess sodium borohydride (0.25 g, 6.61 mmol) was added to a solution of the imine 20 (0.45 g, 1.36 mmol) in a 2:1 mixture of THF and methanol. The mixture was stirred overnight at room temperature before quenching with water. Volatiles were removed under reduced pressure and the solution pH was adjusted at 9 with careful addition of conc. HCl. Mixture was extracted with DCM. The organic layer was washed with water and then with brine solution, finally dried over anhydrous Na$_2$SO$_4$. Solution was concentrated and pure product was precipitated with the addition of excess hexane. Precipitate was dried under vacuum to get brown powder.

Yield: 0.4 g (88%). $^1$H NMR (300 MHz, DMSO-d6): δ 8.90 (s, 1H), 7.99 (d, J=9.1, 2H), 7.26 (d, J=7.8, 2H), 7.13 (d, J=7.8, 2H), 6.95 (d, J=8.5, 2H), 6.76 (d, J=9.1, 2H), 6.61 (d, J=8.5, 2H), 6.24 (t, J=5.9, 1H), 4.22 (d, J=5.9, 2H), 2.27 (s, 3H). $^{13}$C NMR (75 MHz, DMSO-d6): δ 152.9, 146.3, 137.0, 136.4, 135.6, 128.8, 127.8, 127.1, 126.2, 124.4, 112.8, 111.7, 46.4, 20.6.

PPD Derivative 9: 4-Amino-4'-[(4-tolylaminomethyl)phenyl]diphenylamine (24)

Tin powder (0.612 g, 5 mmol) was added to a 15 mL conc. HCl suspension of 4-Nitro-4'-[(4-tolylaminomethyl)phenyl]diphenylamine 22 (0.334 g, 1 mmol) and the mixture was refluxed overnight. Upon completion of the reaction, the colourless solution was diluted with 50 mL of water and placed in an ice bath and the pH of the mixture was adjusted to 12. White precipitate appeared was filtered, quickly washed with water and dried in vacuo.

Yield: 0.268 g (88%). $^1$H NMR (400 MHz, DMSO) δ 7.24 (d, J=7.9, 2H), 7.12 (d, J=7.8, 2H), 6.78 (s, 1H), 6.66 (dd, J=12.3, 5.3, 5H), 6.49-6.44 (m, 5H), 5.58 (s, 1H), 4.47 (s, 2H), 4.14 (d, J=4.4, 2H), 2.27 (s, 3H).

Example 10

Synthesis of PPD Derivative 10: N$^1$-[4-(4-tolylaminomethyl)phenyl]-N$^4$-(4-aminophenyl)-1,4-benzenediamine (25)

N$^1$-(4-aminophenyl)-N$^4$-(4-nitrophenyl)-1,4-benzenediamine (19)

1-Fluoro-4-nitrobenzene (0.31 mL, 2.9 mmol) and triethylamine (0.8 mL, 5.74 mmol) was added successively to 7 ml DMSO solution of 4,4'-Diaminodiphenylamine (0.5948 g, 2.98 mmol) under inert atmosphere. After 24 hours of stirring at 90° C., reaction mixture was cooled and poured into water to induce precipitation. The dark precipitate was collected by filtration, washed with water and dried under suction. The crude product was purified by gradient column chromatography while the desired product eluted with 2% DCM/ethyl acetate mixture.

Yield: 0.28 g. $^1$H NMR (300 MHz, DMSO-d6): δ 8.98 (s, 1H), 8.01 (d, J=9.1, 2H), 7.53 (s, 1H), 7.01 (d, J=8.6, 2H), 6.83 (dd, J=11.7, 4.9, 6H), 6.55 (d, J=8.5, 2H), 4.76 (s, 2H). $^{13}$C NMR (75 MHz, DMSO-d6): δ 152.7, 144.0, 143.8, 136.6, 131.7, 129.1, 124.3, 122.3, 114.7, 114.4, 111.9.

$N^1$-[(4-imino-p-tolyl)phenyl]-$N^4$-(4-nitrophenyl)-1,4-benzenediamine (21) p-Toluenecarboxaldehyde (0.11 mL, 0.93 mmol) and catalytic amount of p-toluenesulphonic acid was added to an ethanolic solution (10 mL) of $N^1$-(4-aminophenyl)-$N^4$-(4-nitrophenyl)-1,4-benzenediamine (0.278 g, 0.86 mmol) and the mixture was stirred overnight at room temperature under nitrogen atmosphere. Resulting orange precipitate was collected by filtration and washed with 20 mL of 20% ethanol/hexane mixture and finally with hexane. Drying over suction afforded pure crystalline solid.

Yield: 0.31 g (86%). $^1$H NMR (300 MHz, DMSO-d6): δ 9.13 (s, 1H), 8.61 (s, 1H), 8.31 (s, 1H), 8.06 (d, J=9.2, 2H), 7.80 (d, J=8.0, 2H), 7.29 (dd, J=13.4, 8.4, 4H), 7.17-7.08 (m, 6H), 6.93 (d, J=9.2, 2H), 2.37 (s, 3H). $^{13}$C NMR (75 MHz, DMSO-d6): δ 156.6, 151.9, 143.0, 142.2, 140.7, 139.8, 137.0, 133.9, 131.9, 129.3, 128.2, 126.2, 123.5, 122.3, 118.0, 116.7, 112.4, 21.05.

$N^1$-[4-(4-tolylaminomethyl)phenyl]-$N^4$-(4-nitrophenyl)-1,4-benzenediamine (23) 1-Fluoro-4-nitrobenzene (0.12 mL, 1.1 mmol) and triethylamine (0.23 mL, 1.2 mmol) was added successively to 7 ml DMSO solution of 4-amino-4'-[(4-tolylaminomethyl)phenyl]diphenylamine 24 (0.303 g, 1 mmol) under inert atmosphere. The dark red solution was stirred at 90° C. for two days, after which the mixture was cooled to room temperature and was dropwise added to 200 ml of chilled water with vigorous stirring which afforded colloidal suspension. Addition of brine solution produced dark brown precipitate which was collected by filtration, washed with water and dried under suction. The crude product was purified by silica gel column chromatography by elution with pure DCM. Yield: 0.1 g (26%).

Alternatively, this compound was also synthesized by reducing the imine group of (E)-N-(4-methylbenzylidene)-$N^4$-(4-((4-nitrophenyl)amino)phenyl)benzene-1,4-diamine (21) (0.2 g, 0.47 mmol) with sodium borohydride (0.1 g, 2.64 mmol) in a 1:2 mixture of methanol/THF. Work up was performed following the method used for the synthesis of 4-Amino-4'-[(4-tolylaminomethyl)phenyl]diphenylamine. Product was isolated as red solid.

Yield: 0.95 g (95%). $^1$H NMR (300 MHz, DMSO-d6): δ 8.98 (s, 1H), 8.01 (d, J=9.1, 2H), 7.55 (s, 1H), 7.26 (d, J=7.8, 2H), 7.12 (d, J=7.8, 2H), 7.00 (d, J=8.6, 2H), 6.90-6.80 (m, 6H), 6.56 (d, J=8.6, 2H), 5.90 (t, J=5.9, 1H), 4.19 (d, J=5.8, 2H), 2.27 (s, 3H). $^{13}$C NMR (75 MHz, DMSO-d6): δ 152.6, 144.2, 143.8, 137.3, 136.6, 135.4, 131.8, 129.2, 128.7, 127.1, 126.2, 124.2, 122.1, 114.5, 113.1, 111.9, 46.8, 20.6.

PPD Derivative 10: $N^1$-[4-(4-tolylaminomethyl)phenyl]-$N^4$-(4-aminophenyl)-1,4-benzenediamine (25) The nitro compound 23 (0.505 g, 1.2 mmol) was dissolved in 20 mL ethanol. To the dark red solution 1.5 g (7.91 mmol) stannous chloride was added followed by 5 mL conc. HCl. Resulting solution was refluxed until all nitro compounds were consumed, as evident from TLC. After cooling the reaction mixture was diluted with water and pH of the solution was adjusted to 10 by addition of 20% aqueous NaOH solution. The cloudy mixture was extracted with ethyl acetate and organic layer was washed with water, brine and dried over anhydrous sodium sulphate. Evaporation of solvent afforded the title compound as off white powder. Yield: 0.34 g (72%). $^1$H NMR (400 MHz, DMSO) δ 7.25 (d, J=7.6, 2H), 7.12 (d, J=7.6, 2H), 6.99 (d, J=8.1, 2H), 6.78-6.67 (m, 8H), 6.49 (d, J=7.0, 4H), 5.66 (s, 1H), 4.56 (s, 2H), 4.15 (d, J=5.4, 2H), 2.27 (s, 3H). $^{13}$C NMR (75 MHz, DMSO-d6): δ 143.1, 142.5, 137.9, 135.8, 134.9, 134.7, 129.1, 127.6, 120.0, 119.8, 117.5, 117.3, 115.3, 113.7, 104.9, 47.5, 21.0.

Example 11

Synthesis of Symmetrically Capped NHR/NHR Capped Dimers (26-29)

TABLE 1

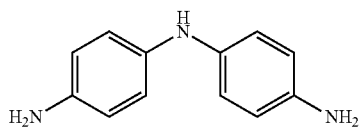

| No. | Aldehyde | Imine |
|---|---|---|
| 1 | 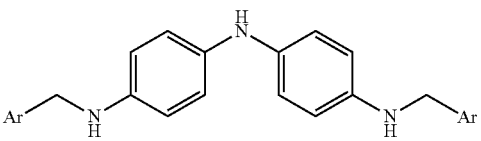 | 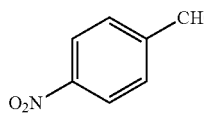 |

TABLE 1-continued
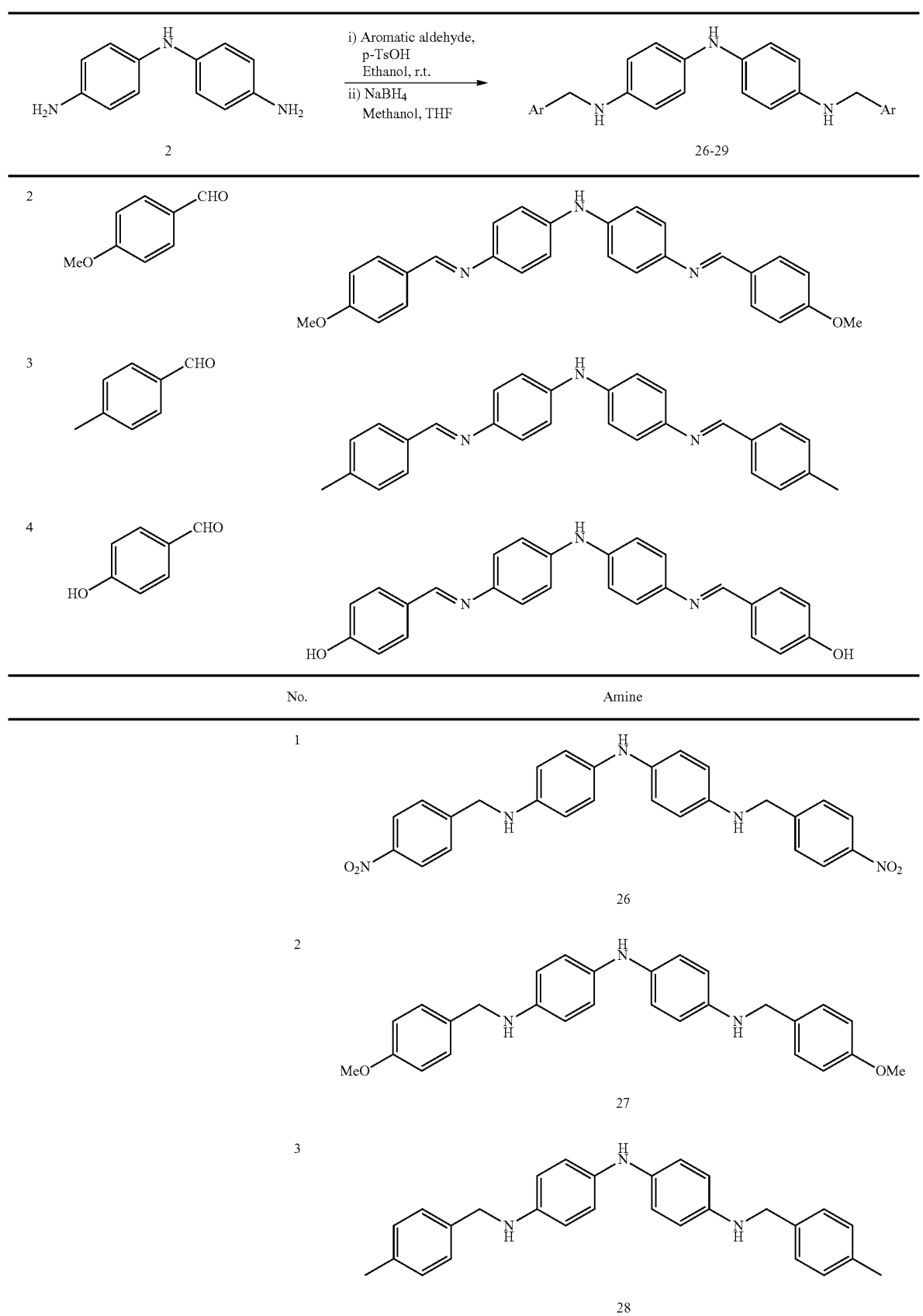

TABLE 1-continued

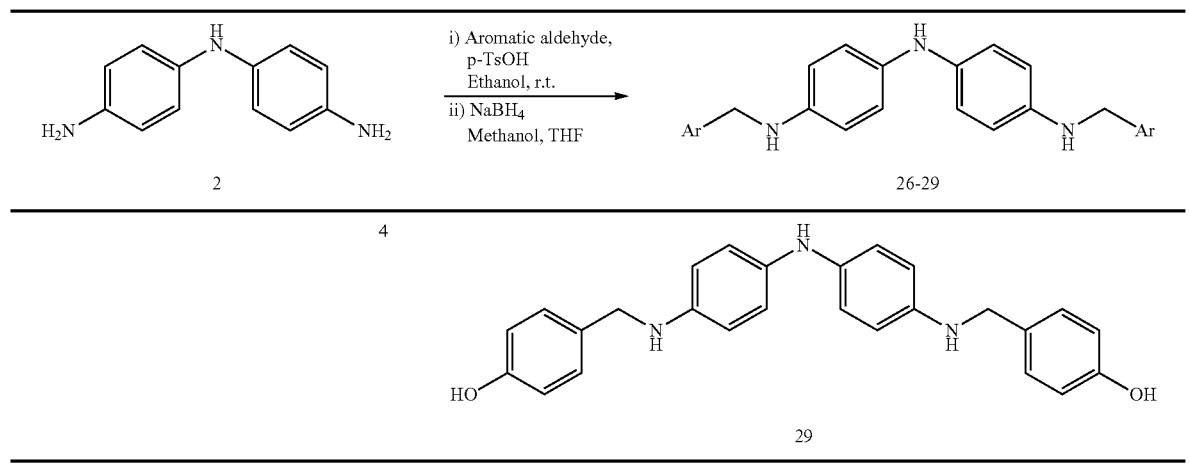

N⁴-[(4-nitrophenyl)methyl]-N¹-[4-[(4-nitrophenyl)methylamino]phenyl]benzene-1,4-diamine (26)

4-[(E)-(4-nitrophenyl)methyleneamino]-N-[4-[(E)-(4-itrophenyl)methyleneamino]phenyl]aniline Using the reagents above and General Procedure 3, where the reaction mixture was stirred at room temperature for 14 hours afforded the title compound, which was isolated as a green powder.

Yield: 0.4 g (95%). $^1$H NMR (400 MHz, DMSO-d6): δ 8.87 (2H, s, C—Himine), 8.71 (1H, s, N—Hamine), 8.36 (4H, d, J=8 Hz, C—HAr), 8.16 (4H, d, J=8 Hz, C—HAr), 7.42 (4H, d, J=8 Hz, C—HAr), 7.20 (4H, d, J=8 Hz, C—HAr). $^{13}$C NMR (100 MHz, DMSO-d6): δ 155.08 (Cimine), 148.85, 143.14, 142.78, 142.70, 129.59, 124.52, 123.64, 117.75. FT-IR (wavenumbers, cm$^{-1}$): vN-H (st) 3416, vN-H (b) 1598, vC=C (st) 1512, vC=N (st) 1621, vN-O (st) 1512, 1332. ESI MS: m/z 465.2.

PPD Derivative 11: N⁴-[(4-nitrophenyl)methyl]-N¹-[4-[(4-nitrophenyl)methylamino]phenyl]-benzene-1,4-diamine (26)

The title compound was synthesized from the corresponding imine using General Procedure 4.

Yield: 0.3 g (82%). $^1$H NMR (400 MHz, DMSO): δ 8.18 (d, J=8.7, 4H), 7.61 (d, J=8.7, 4H), 6.87 (s, 1H), 6.66 (d, J=8.7, 4H), 6.43 (d, J=8.8, 4H), 5.91 (t, J=6.2, 2H), 4.34 (d, J=6.1, 4H). $^{13}$C NMR (100 MHz, DMSO): δ 150.1, 148.8, 142.0, 136.2, 128.6, 123.9, 118.9, 113.9, 47.2.

N⁴-[(4-methoxyphenyl)methyl]-N¹-[4-[(4-ethoxyphenyl)methylamino]phenyl]benzene-1,4-diamine (27)

4-[(E)-(4-methoxyphenyl)methyleneamino]-N-[4-[(E)-(4-methoxyphenyl)methyleneamino]phenyl]aniline Using the reagents above and General Procedure 3, where the reaction mixture was stirred at room temperature for 14 hours afforded the title compound, which was isolated as a golden yellow crystalline powder.

Yield: 0.45 g (84%). $^1$H NMR (400 MHz, DMSO-d6): δ 8.57 (2H, s, C—H imine), 8.34 (1H, s, N—H amine), 7.86 (4H, d, J=8 Hz, C—H Ar), 7.24 (4H, d, J=8 Hz, C—H Ar), 7.12 (4H, d, J=8 Hz, C—H Ar), 7.06 (4H, d, J=8 Hz, C—H Ar), 3.83 (6H, s, OCH3). $^{13}$C NMR (100 MHz, DMSO-d6): δ 161.44 (C imine), 156.37, 143.49, 141.64, 129.94, 129.39, 122.17, 117.19, 114.19, 55.33 (OCH3). FT-IR (wavenumbers, cm$^{-1}$): vN-H (st) 3421, vC-H (st) 2959-2839, vN-H (b) 1604, vC=N (st) 1621, vC=C (st) 1512, vC-O (st) 1250, 1028, vC=C (b) 844. ESI MS: 436.6 (M+H)+.

PPD Derivative 12: N⁴-[(4-methoxyphenyl)methyl]-N¹-[4-((4-ethoxyphenyl)methylaminol-phenyl]benzene-1,4-diamine (27)

The title compound was synthesized from the corresponding imine using general procedure 4.

Yield: 0.37 g (88%). $^1$H NMR (400 MHz, DMSO): δ 7.27 (d, J=8.6, 4H), 6.87 (d, J=8.6, 4H), 6.81 (s, 1H), 6.67 (d, J=8.7, 4H), 6.47 (d, J=8.7, 4H), 5.54 (t, J=6.0, 2H), 4.11 (d, J=6.0, 4H), 3.73 (s, 6H). $^{13}$C NMR (100 MHz, DMSO): δ 150.5, 142.7, 135.9, 132.9, 128.9, 118.8, 114.1, 113.9.

N⁴-(p-tolylmethyl)-N¹-[4-(p-tolylmethylamino)phenyl]benzene-1,4-diamine (28)

4-[(E)-p-tolylmethyleneamino]-N-[4-[(E)-p-tolylmethyleneamino]phenyl]aniline

Using the reagents above and General Procedure 3, where the reaction mixture was stirred at room temperature for 14 hours afforded the title compound, which was isolated as a golden yellow crystalline powder.

Yield: 0.36 g (80%). $^1$H NMR (400 MHz, DMSO-d6): δ 8.62 (2H, s, C—H imine), 8.40 (1H, s, N—H amine), 7.81 (4H, d, J=8 Hz, C—H Ar), 7.32 (4H, d, J=8 Hz, C—H Ar), 7.28 (4H, d, J=8 Hz, C—H Ar), 7.13 (4H, d, J=8 Hz, C—HAr), 2.38 (6H, s, CH3). $^{13}$C NMR (100 MHz, DMSO-d6): δ 157.32 (C imine), 143.78, 142.34, 142.25, 134.46, 129.84, 128.76, 122.83, 117.50, 21.61 (CH3). FT-IR (wavenumbers, cm$^{-1}$): vN-H (st) 3421, vC-H (st) 2959-2839, vN-H (b) 1604, vC=N (st) 1621, vC=C (st) 1512, vC-O (st) 1250, 1028, vC=C (b) 844. ESI MS: 404.6 (M+H)+.

PPD Derivative 13: N⁴-(p-tolylmethyl)-N¹-[4-(p-tolylmethylamino)phenyl]benzene-1,4-diamine (28)

The title compound was synthesized from the corresponding imine using general procedure 4.

Yield: 0.45 g (90%). $^1$H NMR (400 MHz, DMSO): δ 7.23 (d, J=7.9, 4H), 7.10 (d, J=7.9, 4H), 6.79 (s, 1H), 6.66 (d, J=8.7, 4H), 6.45 (d, J=8.7, 4H), 5.58 (t, J=6.1, 2H), 4.13 (d, J=5.9, 4H), 2.34 (s, 6H). $^{13}$C NMR (100 MHz, DMSO): δ 142.7, 138.1, 135.9, 135.8, 129.2, 127.7, 118.8, 113.8, 47.6, 21.1.

4-[[4-[4-[(4-hydroxyphenyl)methylamino]anilino]anilino]methyl]phenol (29)

4-[(E)-[4-[4-[(E)-(4-hydroxyphenyl)methyl-eneamino]anilino]phenyl]iminomethyl]phenol Using the reagents above and General Procedure 3, where the reaction mixture was stirred at room temperature for 14 hours afforded the title compound, which was isolated as a yellow-orange crystalline powder.

Yield: 0.56 g (75%). $^1$H NMR (400 MHz, DMSO-d6): δ 10.03 (2H, s, 0-H), 8.51 (2H, s, C—H imine), 8.31 (1H, s, N—H amine), 7.75 (4H, d, J=8 Hz, C—H Ar), 7.25 (4H, d, J=6.5 Hz, C—H Ar), 7.11 (4H, d, J=7 Hz, C—HAr), 6.88 (4H, d, J=8 Hz, C—HAr). $^{13}$C NMR (100 MHz, DMSO-d6): δ 160.61 (C imine), 157.16, 144.19, 142.00, 130.67, 128.42, 122.57, 117.69, 116.07). ESI MS: 408.5 (M+H)+.

PPD Derivative 14: 4-[[4-[4-[(4-hydroxvphenyl)methylamino]anilino]anilino]methyl]phenol (29)

The title compound was synthesized from the corresponding imine using general procedure 4.

Yield: 0.58 g (67%). $^1$H NMR (300 MHz, DMSO): δ 9.22 (s, 2H), 7.14 (d, J=8 Hz, 2H), 6.81-6.66 (m, 9H), 6.47 (d, J=8 Hz, 4H), 5.45 (t, J=5.4 Hz, 2H), 4.05 (d, J=5.1 Hz, 4H). 13C NMR (100 MHz, DMSO): δ 156.4, 142.7, 135.8, 131.0, 128.8, 122.4, 118.7, 115.3, 113.7, 104.9, 47.4.

Example 12

Synthesis of PPD Derivative 15: Hexyl-2,5-diaminobenzoate (30)

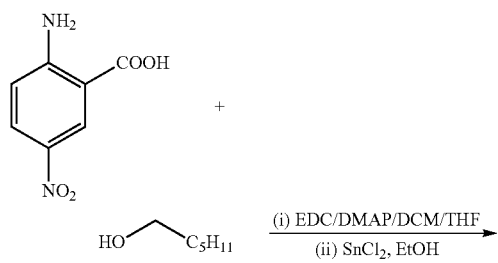

Hexyl-2-amino-5-nitrobenzoate

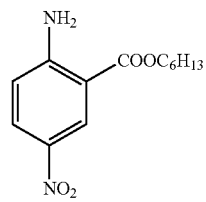

5-nitroanthranilic acid (1.05 g, 5.7 mmol) was dissolved in 1:1 mixture of DCM and THE kept under inert atmosphere and EDC (2.2 g, 11.5 mmol), DMAP (0.35 g, 2.9 mmol) and n-hexanol (0.7 mL, 5.6 mmol) were successively added to the yellow solution. Mixture was stirred vigorously at room temperature for 3 hours. During the course of reaction, a lot of yellow precipitate was formed which slowly dissolved. Volatiles were removed under reduced pressure and the residue was dissolved in DCM and the solution was washed thrice with saturated NaHCO$_3$ solution, thrice with water and finally with brine solution. Evaporation of solvent afforded the crude product as red oil. Pure compound was isolated as bright yellow solid after purification by column chromatography using 60% dcm/hexane mixture.

Yield: 1.4 g (90%). 1H NMR (500 MHz, DMSO) δ 8.59 (d, J=2.7, 1H), 8.09 (dd, J=9.3, 2.8, 1H), 7.85 (s, 2H), 6.90 (d, J=9.4, 1H), 4.27 (t, J=6.6, 2H), 1.73 (t, J=7 Hz, 2H), 1.44-1.36 (m, 2H), 1.35-1.29 (m, 4H), 0.88 (t, J=6.9, 3H). $^{13}$C NMR (125 MHz, DMSO) δ 165.9, 155.8, 135.1, 128.8, 128.1, 116.7, 107.6, 64.7, 30.8, 28.0, 25.1, 21.9, 13.8.

PPD Derivative 15: Hexyl-2,5-diaminobenzoate (30)

Excess tin(II) chloride (2.3 g, 12 mmol) was added to an ethanolic solution of 0.8 g (3 mmol) of hexyl 2-amino-5-nitrobenzoate. Resulting mixture was refluxed for 24 hours. After cooling solvent was evaporated and the residue was taken into water and the pH of the mixture was adjusted at 8 with addition of aqueous K$_2$CO$_3$ solution. Mixture was extracted with ethyl acetate and the organic layer was quickly washed with water and finally with brine solution. After solvent evaporation residue was dried under vacuum to get the title compound. Yield: 0.6 g (84%). $^1$H NMR (500 MHz, DMSO) δ 7.00 (d, J=3 Hz, 1H), 6.69 (dd, J=8.7 Hz, 2.7 Hz, 1H), 6.57 (d, J=8.6 Hz, 1H), 5.87 (s, 2H), 4.43 (s, 2H), 4.17 (t, J=6.6 Hz, 2H), 1.67 (quintet, J=7 Hz, 2H), 1.43-1.35 (m, 2H), 1.35-1.28 (m, 5H), 0.88 (t, J=7 Hz, 3H). $^{13}$C NMR (125 MHz, DMSO) δ 168.1, 143.7, 138.3, 123.7, 118.1, 114.3, 110.1, 64.0, 31.4, 28.8, 25.7, 22.5, 14.4.

Example 13

Synthesis of PPD Derivative 16: (N$^1$-hexyl)(2-hexyloxy)-1,4-diaminobenzene (31)

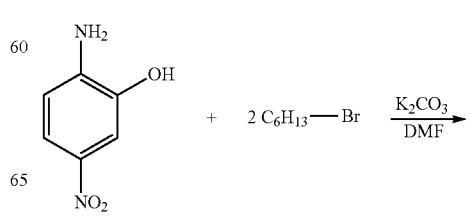

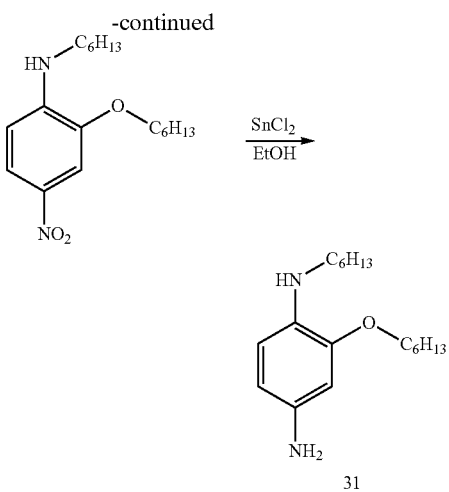

($N^1$-hexyl)(2-hexyloxy)-4-nitroaniline

The title compound was obtained by analogy to the process to make 2-hexyloxy-4-nitroaniline above (Example 4), except that 41 mmol of 1-bromohexane and $K_2CO_3$ were used.

The compound was isolated from the reaction mixture by elution with a 20% ethyl acetate and hexane mixture. A bright yellow viscous liquid was obtained upon evaporation of the effluents.

Yield: 3.2 g (76%). $^1$H NMR (300 MHz, DMSO) δ 7.81 (dd, J=9.0, 2.4, 1H), 7.53 (d, J=2.5, 1H), 6.61 (d, J=9.0, 1H), 6.35 (t, J=5.4 Hz, 1H), 4.07 (t, J=6.4, 2H), 3.23 (dd, J=13.6, 6.6, 2H), 1.82-1.70 (m, 2H), 1.54 (m, 2H), 1.44 (m, 2H), 1.38-1.23 (m, 10H), 0.87 (q, J=6.8, 6H). $^{13}$C NMR (75 MHz, DMSO) δ 145.3, 144.4, 135.4, 120.2, 106.8, 105.6, 68.8, 42.43, 31.3, 28.7, 28.6, 26.4, 25.5, 22.4, 14.2

PPD Derivative 16: ($N^1$-hexyl)(2-hexyloxy)-1,4-diaminobenzene (31)

Following the method for the synthesis of 2-hexyloxy-1,4-diaminobenzene 6, reduction of ($N^1$-hexyl)(2-hexyloxy)-4-nitroaniline (1 g, 3.1 mmol) was performed using 3 g (15.8 mmol) tin(II) chloride in presence of 2 mL of conc. HCl.

Yield: 0.89 g (99%). $^1$H NMR (300 MHz, DMSO) δ 6.31 (d, J=8.2, 1H), 6.21 (d, J=2.1, 1H), 6.06 (dd, J=8.1, 1.6, 1H), 4.27 (s, 2H), 3.84 (t, J=6.3, 2H), 2.93 (t, J=6.7, 2H), 1.77-1.64 (m, 2H), 1.57-1.46 (m, 2H), 1.47-1.37 (m, 3H), 1.30 (m, 10H), 0.87 (q, J=6.8, 6H). $^{13}$C NMR (75 MHz, DMSO) δ 147.2, 139.8, 129.9, 111.9, 106.7, 100.6, 67.9, 44.6, 31.5, 31.4, 29.4, 29.1, 26.7, 25.7, 22.5, 22.4, 14.2

Example 14

Products Formed Through Oxidation of PPD and PPD Derivatives 2-5 (Compounds 4-6, and 14, Respectively)

The oxidations were conducted using a 3% $H_2O_2$ in an ammoniacal medium and were monitored by multiple reaction monitoring mass spectroscopy (MRM).

Sample Preparation Procedure

To 2 mL Eppendorf tubes 0.2 mL of DPBS buffer, 2 μL of 100 μM ANP (IS), 40 μL of concentrated ammonium hydroxide (30%) and 1.0 mL of methylene chloride were added. The tubes were then vortex mixed for 3 min and supernatant was removed. The extraction was repeated again with 1 mL of methylene chloride. During the sample preparation process, the samples were kept at dry ice to avoid the oxidation of PPD to metabolite bandrowski base. Then the organic layer was transferred to 2 mL Eppendorf tubes and evaporated to dryness under a stream of nitrogen, using the TurboVap system at a pressure of 3-5 psi at 35° C. The dried extracts were reconstituted in 200 μL of 0.1% formic acid in acetonitrile and 5 μL was injected into the LC-MS/MS system.

Multiple Reaction Monitoring Mass Spectroscopy Conditions

Compound independent parameters that remained constant for PPD and the tested compounds were as follows under multiple reaction monitoring mass spectroscopy (MRM): curtain gas (CUR): 15 psi; Ion source gas 1 (GS1, sheath gas) 45 psi; Ion source gas 2 (GS2, drying gas) 45 psi; Ion spray voltage (ISV): 5000V; Collision gas (CAD, nitrogen): medium; Interface heater (Ihe) switched on; Quadrupole 1 and quadrupole 3 were maintained at unit resolution. Dwell time set was 100 ms for all compounds.

Calibration Curve Preparation

A stock solution of PPD with a concentration of 10 mM was prepared by dissolving 1.8 mg free base of PPD in 1665 μL Milli-Q water. Stock solutions of MAPPD, BB, DAPPD (1 mg/mL) were prepared separately by dissolving 2 mg of each analyte in 2 mL of methanol. Working solutions were prepared by diluting the stock solutions of each analyte to a final concentration. Different stock standards were used to prepare quality control (QC) samples at the same concentrations. Working calibrators (10 μM, 1 μM, 0.1 μM, 0.01 μM, 0.001 μM, 0.005 μM, 0.0001 μM, 0.00001 μM, 0.000005 μM) for PPD, MAPPD, BB and DAPPD were made in Dulbecco's phosphate buffer saline (DPBS). Low, medium and high quality controls (LQC, MQC and HQC) were also prepared in DPBS at concentration of 7.5, 0.05 and 0.00005 μM for all analytes. A working internal standard containing 1 μM of ANP was prepared by diluting the stock solutions of acetanilide (1.0 mg/mL) with methanol. Stock solutions and working solutions for dimer, trimer and their metabolites were prepared in the same manner as PPD solution. Standard solutions were stored at −20° C. until use.

Method Validation

The method was validated according to USFDA guidelines. Validation parameters such as specificity, sensitivity, linearity, inter- and inter-assay precision, accuracy, recovery, stability were assessed to evaluate method integrity. This method was then used in the skin permeation experiments below.

PPD Oxidation

Oxidation of PPD was performed with 3% $H_2O_2$ in an ammoniacal medium. The reaction was monitored using multiple reaction monitoring mass spectroscopy. The MRM transitions of PPD and metabolites are reflected in Table 2. The compound dependent parameters, such as the collision energy (CE) and de-clustering potential (DP) were adjusted to provide the highest sensitivity.

TABLE 2

| Compound | RT (min) | MRM (m/z) | (CE) (V)* | (DP) (V) | (EP) (V) | (CXP) (V) |
|---|---|---|---|---|---|---|
| PPD | 0.84 | 109.200-92.0 | 13.730 | 154.970 | 12.420 | 10.770 |
| MAPPD | 1.19 | 151.400-92.000 | 20.560 | 76.090 | 11.690 | 8.710 |
| DAPPD | 2.39 | 193.210-109.100 | 36.00 | 54.160 | 27.840 | 6.050 |
| BB | 2.15 | 319.230-303.300 | 26.350 | 109.200 | 4.7600 | 8.720 |
| ANP | 2.62 | 140.200-94.200 | 21.540 | 110.00 | 8.850 | 5.680 |

*V: Volts, CE: collision energy, DP: declustering potential, EP: entrance potential, CXP: collision exit potential.

Figure 2:
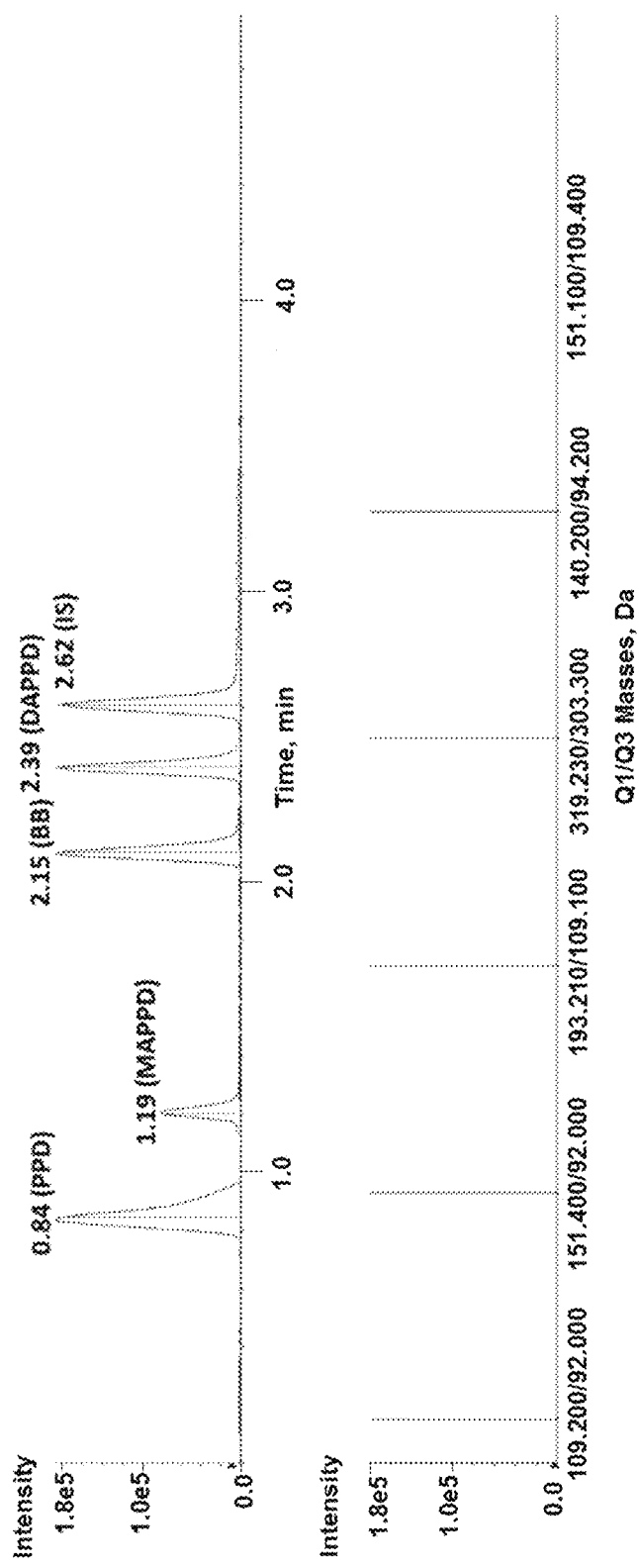

FIG. 2 shows that the major product isolated from the PPD oxidation is the trimeric form of PPD, commonly known as the Bandrowski's base (BB, 32). It was isolated as dark brown black solid with limited solubility in water. In addition to BB, small amount of p-nitroaniline (33) and 4,4'-diaminoazobenzene (34) were also isolated.

Oxidation of PPD Derivatives 1-5 (Compounds 2, 4-6, and 14, Respectively)

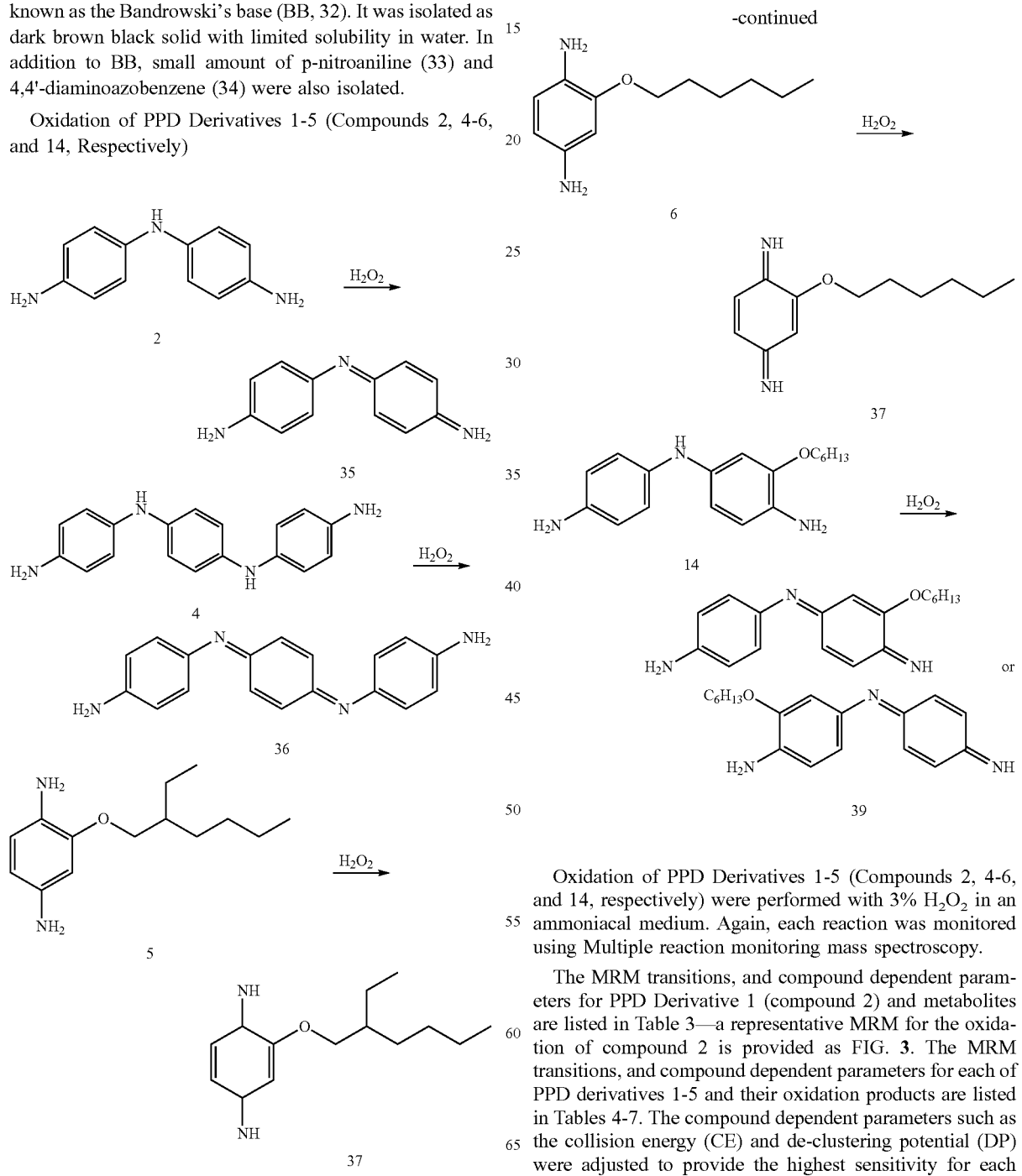

Oxidation of PPD Derivatives 1-5 (Compounds 2, 4-6, and 14, respectively) were performed with 3% $H_2O_2$ in an ammoniacal medium. Again, each reaction was monitored using Multiple reaction monitoring mass spectroscopy.

Figure 3:
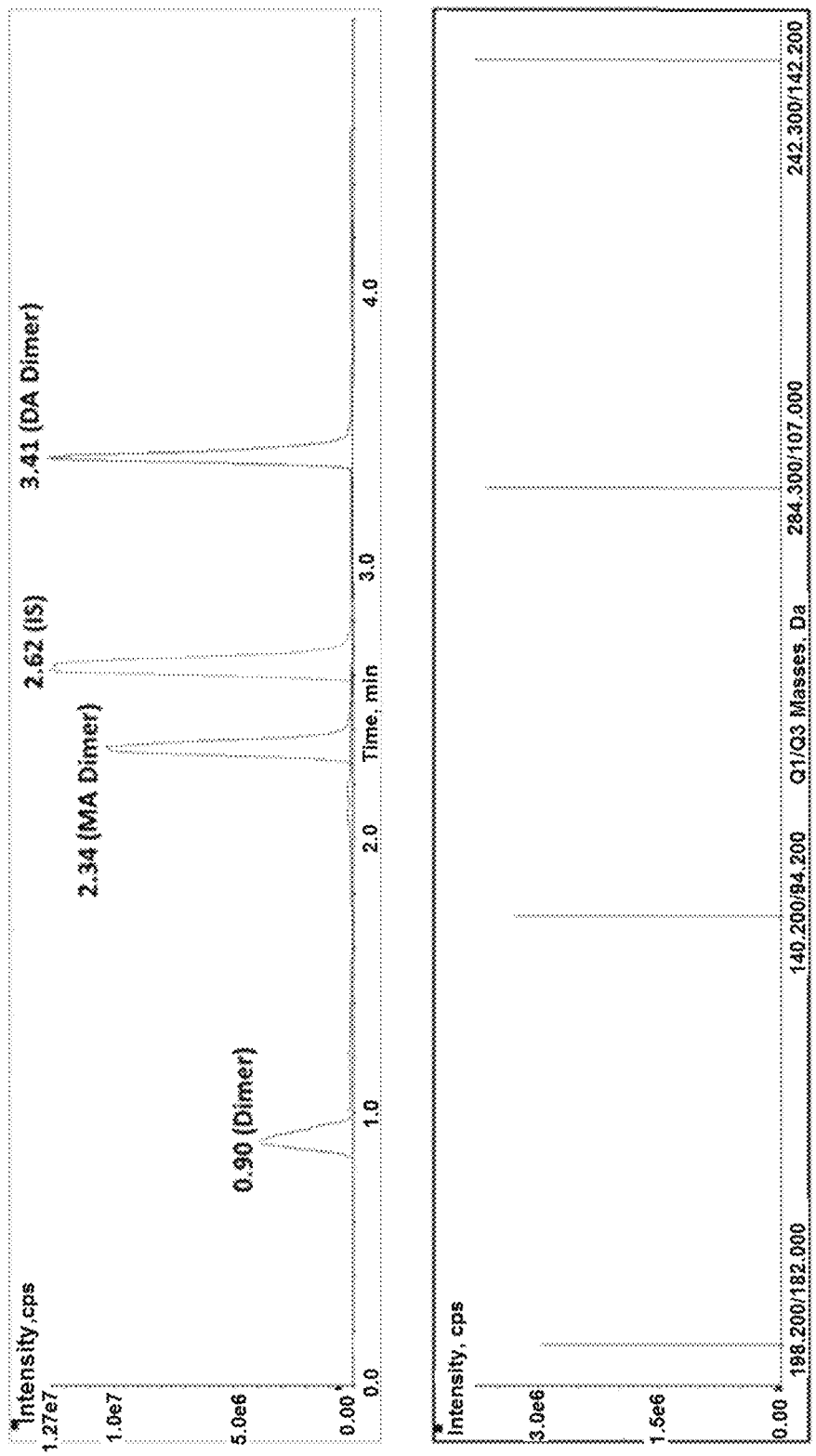

The MRM transitions, and compound dependent parameters for PPD Derivative 1 (compound 2) and metabolites are listed in Table 3—a representative MRM for the oxidation of compound 2 is provided as FIG. 3. The MRM transitions, and compound dependent parameters for each of PPD derivatives 1-5 and their oxidation products are listed in Tables 4-7. The compound dependent parameters such as the collision energy (CE) and de-clustering potential (DP) were adjusted to provide the highest sensitivity for each material.

TABLE 3

| Compound | RT (min) | MRM(m/z) | (CE) (V) | (DP) (V) | (EP) (V) | (CXP) (V) |
|---|---|---|---|---|---|---|
| Derivative 1 | 0.90 | 198.20-182.0 | 27.30 | 72.63 | 7.66 | 10.85 |
| MA Derivative 1 | 2.34 | 242.30-142.20 | 28.51 | 89.56 | 6.02 | 12.23 |
| DA Derivative 1 | 3.41 | 284.30-107.0 | 26.08 | 55.18 | 4.66 | 7.40 |
| ANP | 2.62 | 140.20-94.20 | 21.540 | 110.00 | 8.850 | 5.680 |

TABLE 4

| Compound | RT (min) | MRM(m/z) | (CE) (V) | (DP) (V) | (EP) (V) | (CXP) (V) |
|---|---|---|---|---|---|---|
| Derivative 2 | 0.92 | 289.20-211.00 | 21.59 | 99.46 | 5.80 | 9.01 |
| MA Derivative 2 | 2.45 | 331.30-182.00 | 36.78 | 123.46 | 11.65 | 9.75 |
| DA Derivative 2 | 3.52 | 375.40-175.0 | 39.18 | 179.05 | 8.78 | 11.94 |
| ANP | 2.60 | 140.20-94.20 | 21.540 | 110.00 | 8.850 | 5.680 |

TABLE 5

| Compound | RT (min) | MRM(m/z) | (CE) (V) | (DP) (V) | (EP) (V) | (CXP) (V) |
|---|---|---|---|---|---|---|
| Derivative 3 | 2.52 | 237.300-125.00 | 15.050 | 67.560 | 4.330 | 9.870 |
| MA Derivative 3 | 2.59 | 279.40-149.00 | 19.220 | 78.490 | 6.180 | 8.870 |
| DA Derivative 3 | 2.78 | 321.400-167.100 | 27.900 | 76.470 | 13.610 | 11.250 |
| ANP | 1.58 | 140.20-94.20 | 21.540 | 110.00 | 8.850 | 5.680 |

TABLE 6

| Compound | RT (min) | MRM(m/z) | (CE) (V) | (DP) (V) | (EP) (V) | (CXP) (V) |
|---|---|---|---|---|---|---|
| Derivative 4 | 2.18 | 209.30-125.00 | 17.590 | 93.850 | 10.970 | 7.930 |
| MA Derivative 4 | 2.38 | 251.30-209.30 | 19.840 | 95.780 | 10.200 | 13.880 |
| DA Derivative 4 | 2.52 | 293.30-167.30 | 25.250 | 89.820 | 6.950 | 12.080 |
| ANP | 1.58 | 140.20-94.20 | 21.540 | 110.00 | 8.850 | 5.680 |

TABLE 7

| Compound | RT (min) | MRM(m/z) | (CE) (V) | (DP) (V) | (EP) (V) | (CXP) (V) |
|---|---|---|---|---|---|---|
| Derivative 5 | 2.64 | 298.3-197.0 | 29.420 | 181.470 | 11.530 | 12.310 |
| MA Derivative 5 | 3.03 | 339.4-304.20 | 18.460 | 71.570 | 7.690 | 5.000 |
| DA Derivative 5 | 4.05 | 384.3-258.40 | 21.540 | 110.000 | 8.850 | 5.680 |
| ANP | 1.96 | 140.2-94.20 | 21.540 | 110.000 | 8.850 | 5.680 |

The oxidation of the dimer (4,4'-diaminobiphenyl (2)) resulted in multiple products. Overnight stirring in the presence of 3% $H_2O_2$ in methanol resulted in a purple-pink mixture. The UV-vis study of the reaction mixture the showed appearance of a distinct band at 672 nm, indicating the formation of indamine dye 35. Oxidation of the trimer (4) under similar conditions gave a dark blue coloured solution, which is attributed to the formation of a monoquinonediamine species, often termed as the emeraldine base (36).

Example 15

Hair Dyeing
Hair Bleaching Process
Schwarzkopf BlondMe Premium Lift 9+ bleaching powder and Schwarzkopf BlondMe 12%/40 vol Developer solution were purchased from amazon and used without further purification. Briefly, the two preparations were mixed thoroughly in the ratio 1:2 in terms of weight:volume. The bleaching solution was then applied onto undyed black hair (wrapped in aluminium foil to enhance the bleaching process) and left for 45 mins. After that, the hair was rinsed with deionized water between each bleaching process for a total of 4 bleaching steps. The bleached hair was then left to air-dry overnight.

Preparation of Dye
For each PPD derivative an equimolar mixture of the PPD derivative and resorcinol was made. The pH of the dye was then adjusted to pH 9.5-10, using 20% $Na_2CO_3$ in deionized water, before addition of $H_2O_2$. Details of the composition of the dye solution are provided in Table 8. The final dye preparations were then left for 20 mins in order for the colour to develop.

TABLE 8

| Content of formulation | Dye composition |
|---|---|
| PPD/PPD derivative (200 mM) | 2.25 mL (final concentration: 90 mM) |

TABLE 8-continued

| Content of formulation | Dye composition |
| --- | --- |
| Resorcinol (250 mM) | 1 mL (final concentration: 90 mM) |
| Deionized water | 1.50 mL |
| H$_2$O$_2$ | 0.15 mL (3%) |
| pH adjusted with 20% Na$_2$CO$_3$ solution | pH 9.5-10 |
| Total Volume | 5 mL |

Dyeing Process

Bleached hair (prepared as above) of approximately 12 cm in length was used for each dye sample. The bleached hair samples were immersed into a dyeing solution for 20 mins. Each hair sample was then removed from the dye preparation it had been subjected to and air dried for 30 mins. The same was then washed with deionized water to remove any excess hair dye. The hair samples were then washed twice with Silkpro VitAir Series Daily Balance Shampoo, and were further treated with Silkpro VitAir Series Daily Treatment Masque (hair conditioner) for 5 mins. The dyed hair samples were then left to be air dried overnight. Blow drying was avoided because it did not provide any difference in terms of colouring—instead blow drying it affected the appearance of the hair, making it frizzy and less smooth.

Large Scale Dyeing

The PPD derivatives that were found to have coloured the hair samples were selected and additional hair samples (%75 grey hair) and dyes were prepared, according to Table 9.

TABLE 9

| Content of formulation | Dye composition | | |
| --- | --- | --- | --- |
| | Type I | Type II | Type III |
| PPD/PPD derivative | 2.25 mL (90 mM) | 2.25 mL (90 mM) | 2.25 mL (90 mM) |
| Resorcinol (250 mM) | — | — | 1 mL (90 mM) |
| Deionized water | 2.75 mL | 2.50 mL | 1.50 mL |
| H$_2$O$_2$ | 0.15 mL (3%) | 0.15 mL (3%) | 0.15 mL (3%) |
| pH adjusted with 20% Na$_2$CO$_3$ solution | | pH 9.5-10 | pH 9.5-10 |
| Total Volume | 5 mL | 5 mL | 5 mL |

Hair samples of approximately 35 cm in length and 1 g in weight were used, and dyed using the similar hair dyeing process stated above.

Extraction of PPD and Derivatives from Hair Samples

Approximately 100 mg of dyed hair was cut from the hair samples dyed according to the procedure in 2b.1.4, at time points corresponding to Day 1 (i.e. on the day of dyeing), Day 2 and Day 7. The hair samples were then dissolved in 2 mL of 1.5 M KOH in 20% ethanol. 100 mg of blank hair samples (unbleached, undyed hair & bleached, undyed hair) were also cut and dissolved to serve as controls. In order to have full extraction of the hair dye from the hair sample, the 100 mg of hair was left to be dissolved overnight. Samples were then frozen by liquid nitrogen and freeze dried overnight. The lyophilized samples were then reconstituted with 5 mL of methanol, centrifuged at 6000 rpm for 10 mins and the supernatant extracted out for further analysis.

LCMS Method Development for Quantification of PPD and PPD Derivatives

For qualitative and quantitative analysis of the extracted samples, LCMS was employed to detect for presence of the PPD derivative/PPD derivative-resorcinol complexes in the extracted hair samples.

The LCMS/MS sample analysis was performed using Agilent 1290 Infinity ultra-high pressure liquid chromatography (UHPLC) (Agilent Technologies Inc., Santa Clara, Calif., USA) interfaced with the AB SCIEX QTRAP 5500 tandem mass spectrometry (MS/MS) system (AB SCIEX, Framingham, Mass., USA). The sample injection volume was 5 µL, and the separation was performed on ACQUITY UPLC BEH C18, 1.7 µM, 2.1×100 mm column (Waters, Mildord, Mass., USA) maintained at 45° C. and the sample at 4° C. Solvent A was composed of 0.1% [v/v] formic acid in Milli-Q water while solvent B was composed of 0.1% [v/v] formic acid in acetonitrile. The solvents were pumped into the column at a flow rate of 0.4 mL/min. The gradient program for PPD was as follows: the initial gradient of 95% B was maintained for 0.5 min, reduced to 50% B over 0.5 min, maintained for 1 min and increased to 95% B over 0.5 min. The column was equilibrated for 1 min resulting in a total run time of 3 min. The injection volume was 5.0 µL. To prevent compound accumulation on the needle, 50% methanol in ACN was used as needle wash for 30 s per sample.

Mass spectrometry parameters for PPD and derivatives are reported in Table 2-7.

Preparation of Calibration Curves of PPD and Selected PPD Derivatives for UV and LC-MS Standard concentrations of 0.0001-1000 µM of PPD, selected PPD derivatives were prepared, using stock solutions of 10 mM. 2 µL of each of the above concentrations were transferred into 2 mL Eppendorf tubes and the volumes made up to 200 µL using 0.1% formic acid in methanol, to make 100× dilutions of the concentrations. 2 µL of an internal standard, ANP of concentration 100 µM was added such that the final concentration of ANP was 1 µM. 100 µL of each standard solution concentration was then transferred to a 96 well plate and stored at 4° C. until LCMS analysis. The UV spectroscopy calibration curve was made using the same concentrations. The absorbance was measured vs concentration of the PPD and PPD derivatives. Using the calibration curves, concentrations of the PPD and PPD derivatives from the extracted hair samples were obtained, and graphs were plotted to observe any change in the concentration of hair dye over the 7 days.

Quantification of PPD and PPD Derivatives in Extracted Hair Samples by UV Spectroscopy UV absorbance wavelengths of each compound were then measured using a Shimadzu UV-1800 UV-VIS spectrophotometer. Approximately 2 mL of the extracted samples were then pipetted into a quartz cuvette, and the absorbance of the concentrations measured using the obtained wavelengths. Table 10 lists the wavelength of the PPD and PPD derivatives obtained in different formulation types.

TABLE 10

Wavelength of the PPD and PPD derivatives in different formulation types.

| Formulation type | Wavelength (nm) | | |
|---|---|---|---|
| | PPD | PPD derivative 1 | PPD derivative 2 |
| Without oxidant ($H_2O_2$) | 237 | 288 | 407 |
| With $H_2O_2$ | 290 | 528 | 560 |
| With coupler (Resorcinol) and $H_2O_2$ | 290 | 525 | 567 |

Results of Dyeing Experiments

Hair dyeing experiments showed that dyes produced from PPD derivative 1-5 were able to impart a colour. However, for all PPD derivatives, a main issue was that solubility in water was limited, and required organic solvents in order to dissolve them. Only derivative 1 showed solubility in a mixture of 10% methanol in water, while the other derivative required fully organic solvents. Hence, PPD derivatives 1-5 were synthesized as the HCl salt form to increase their water solubility and were selected to conduct large scale dyeing as well for investigation of the dye permanence after multiple washes.

On large scale dyeing with the above compounds, it was found that derivatives 1 and 2 produced vibrant colours (see Table 11), in contrast to the bleached hair tone. This opens up the possibility of derivatives 1 and 2 being incorporated into hair dye preparations to provide persistent, bright colours.

It is noted that the colours reported in Table 11 are specific for bleached hair. In the experiments with 75% grey hair, the dye had to undergo oxidation with 3% $H_2O_2$ to provide the same colours as those reported in the second column of Table 11. In other words, the PPD derivatives also colour grey hair, provided the dye formulation includes $H_2O_2$ (in accordance with Type II dye composition listed in Table 9). This is because dyeing grey hair is more difficult and the use of peroxide is needed to enable the dyeing to occur.

TABLE 11

| PPD | PPD + $H_2O_2$ | PPD + Resorcinol + $H_2O_2$ |
|---|---|---|
| PPD no colour | Black | Brown |
| PPD derivative 1 Black | PPD derivative1 + $H_2O_2$ Black | PPD derivative1 + resorcinol + $H_2O_2$ Dark Brown |
| PPD derivative 2 Bluish purple | PPD derivative 2 + $H_2O_2$ Grey | PPD derivative 2 + resorcinol + $H_2O_2$ light Grey |
| PPD derivative 3 Purple | PPD derivative 3 + $H_2O_2$ Black | PPD derivative 3 + resorcinol + $H_2O_2$ Black |
| PPD derivative 4 Magenta | PPD derivative 4 + $H_2O_2$ Black | PPD derivative 4 + resorcinol + $H_2O_2$ Dark magenta |
| PPD derivative 5 Black | PPD derivative5 + $H_2O_2$ Black | PPD derivative 5 + resorcinol + $H_2O_2$ Dark brown |
| PPD derivative 6 Green | PPD derivative 6 + $H_2O_2$ Dark Green | — |
| PPD derivative 15 Brown | PPD derivative 15 + $H_2O_2$ Black | — |

Results of Quantification by LCMS

Using the calibration curves, the amount of PPD/PPD derivative were determined and reported in Table 12. The results showed that, despite numerous washes of the hair sample, PPD and derivatives 1 and 2 were still able to be retained in the hair samples, as concentrations of all three compounds remained fairly constant.

TABLE 12

Quantification of compounds from extracted hair samples using LCMS.

| | | Concentration of PPD (mg) | | |
|---|---|---|---|---|
| LC-MS | Day | PPD only | PPD + $H_2O_2$ | PPD + resorcinol + $H_2O_2$ |
| | 1 | 0.001517 | 0.00086 | 0.001337 |
| | 2 | 0.001568 | 0.00085 | 0.00142 |
| | 7 | 0.001264 | 0.001138 | 0.001504 |

| | Concentration of PPD derivative 1 (mg) | | |
|---|---|---|---|
| Day | Dimer only | Dimer + $H_2O_2$ | PPD derivative 1 + resorcinol + $H_2O_2$ |
| 1 | 2.7319E−05 | 0.218766614 | 0.12092588 |
| 2 | 2.25666E−05 | 0.218345598 | 0.154687989 |
| 7 | 2.46108E−05 | 0.244077254 | 0.122707619 |

| | Concentration of PPD derivative 2 (mg) | | |
|---|---|---|---|
| Day | Trimer only | Trimer + $H_2O_2$ | PPD derivative 2 + resorcinol + $H_2O_2$ |
| 1 | 0.247302 | 0.197543 | 0.097643 |
| 2 | 0.224219 | 0.143284 | 0.122804 |
| 7 | 0.232342 | 0.175174 | 0.105353 |

Results of Quantification by UV Spectroscopy

The dyed hair samples which were dyed using a mixture of resorcinol and PPD or its derivatives, each showed different colours with variations in wavelength as shown in Table 13. This may be due to the differences in the complex formed between resorcinol with PPD and each of its derivatives. UV absorbance of the complexes formed in the extracted hair samples was then measured. For all three compounds, the UV absorbance remained fairly constant, supporting the data obtained above in Table 10 and thus further supporting the fact that all three compounds/complexes were able to be retained in the hair samples.

TABLE 13

| UV spectroscopy | Day | PPD only | PPD + $H_2O_2$ | PPD + resorcinol + $H_2O_2$ |
|---|---|---|---|---|
| | 1 | 0.257 | 0.423 | 0.458 |
| | 2 | 0.232 | 0.418 | 0.452 |
| | 7 | 0.268 | 0.482 | 0.469 |

PPD (Absorbance at 290 nm)

| | Day | PPD derivative 1 only | PPD derivative 1 + $H_2O_2$ | PPD derivative 1 + resorcinol + $H_2O_2$ |
|---|---|---|---|---|
| | 1 | 1.76 | 3.57 | 1.735 |
| | 2 | 1.47 | 3.50 | 1.68 |
| | 7 | 1.48 | 3.47 | 1.71 |

PPD derivative 1 (Absorbance at 525 nm)

| | Day | PPD derivative 2 only | PPD derivative 2 + $H_2O_2$ | PPD derivative 2 + resorcinol + $H_2O_2$ |
|---|---|---|---|---|
| | 1 | 0.561 | 0.639 | 0.733 |
| | 2 | 0.549 | 0.675 | 0.721 |
| | 7 | 0.612 | 0.701 | 0.698 |

PPD derivative 2 (Absorbance at 567 nm)

From the hair dyeing experiments, PPD derivatives 1-5 can be considered as potential alternative chemicals to PPD for hair dyeing. The derivatives produced vibrant colours, in contrast to bleached hair, and the results from UV spectroscopy and LCMS have proven that they are able to be retained in the hair, despite repeated washing. In fact, the PPD derivative compounds by themselves were able to produce strong colours alone on bleached hair, even without the presence of resorcinol and hydrogen peroxide. This could be beneficial in the long run, as hydrogen peroxide is known to damage the hair, and resorcinol is a potential sensitizer as well.

Colour Intensity Measurement

Table 14 presents the results of the hair dyeing performance of the PPD, PPD derivatives 1-5 in compositions of the invention compared with that of PPD (Compound 1 in the table) and various analogues of PPD using, derivatives alone (Type A), derivatives with the oxidant hydrogen peroxide (Type B) and derivatives with coupler resorcinol (Type C). For these evaluations, equimolar amounts of primary dye intermediate (0.09 M) and coupling agent (0.09 M) were used (for example see Table 9). The primary intermediate and coupling agent were mixed with 3% vol hydrogen peroxide and aged for 45 mins to allow reaction to take place. The mixture was subsequently applied to a blend of bleached hair swatches with a treatment period of 30-45 mins at room temperature. Thereafter the dyed hair was rinsed with water and shampoo and dried.

Delfin-Skin Color Catch-Colour intensity chromometer was used to measure the colour of the hair.

The following parameters were measured using this instrument.

L*—indicates lightness of the colour of hair, ranging from black to white (0-100)

a*—is the axis of green to red shades (−128 to +127)

b*—is the axis of blue to yellow shades (−128 to +127)

$L_0$, $a_0$, $b_0$—values measured from the natural hair

In Table 14A L*, a* and b* represent the standard Hunter Tristimulus values, which measure the depth and tonality of the colour. In the hunter method, the parameters a* and b* may be positive or negative and define the chromatic condition of the hair. Similarly, positive b value indicates the yellowness, while negative b values indicate blueness. The L* parameter is a measure of colour intensity and has a value of 0 for absolute black to 100 for absolute white.

The difference in the color tone is measure by $\Delta H$, $\Delta H = \sqrt{(a^*-a_0)+(b^*-b_0)^2}$ and total colour difference, as determined by $\Delta E$, $\Delta E = \sqrt{(L^*-L_0)+(a^*-a_0)+(b^*-b_0)^2}$ Results

TABLE 14A

Hair dyeing performance of PPD versus PPD substituted derivatives of the present invention (PPD analogues) without any oxidant (A), with oxidant $H_2O_2$ (B), with coupling agent Resorcinol (C)

| Analogues | Natural hair | $L^0$ 9 | L* | $a_0$ 0 | a* | $b_0$ 1 | b* | $\Delta E$ | $\Delta H$ |
|---|---|---|---|---|---|---|---|---|---|
| PPD | A | | 57 | | 0 | | 30 | 8.77 | 5.38 |
| | B | | 14 | | 1 | | 3 | 2.82 | 1.73 |
| | C | | 9 | | 0 | | 1 | 0 | 0 |
| PPD derivative1 | A | | 11 | | 1 | | 2 | 2 | 1.41 |
| | B | | 9 | | 1 | | 1 | 1 | 1 |
| | C | | 9 | | 1 | | 1 | 1 | 1 |
| PPD derivative 2 | A | | 22 | | 4 | | 1 | 4.12 | 2 |
| | B | | 35 | | 5 | | 0 | 5.47 | 2 |
| | C | | 49 | | 8 | | 8 | 7.41 | 3.87 |
| PPD derivative 3 | A | | 17 | | 13 | | 2 | 4.69 | 3.74 |
| | C | | 9 | | 6 | | 1 | 2.44 | 2.44 |
| PPD derivative 4 | A | | 16 | | 7 | | 0 | 3.6 | 2.44 |
| | C | | 21 | | 10 | | 3 | 4.89 | 3.46 |
| PPD derivative 5 | A | | 9 | | 0 | | 1 | 0 | 0 |
| | B | | 11 | | 1 | | 2 | 2 | 1.41 |
| | C | | 9 | | 1 | | 1 | 1 | 1 |
| PPD derivative 6 | A | | 45 | | 3 | | 1 | 6.2 | 1.7 |
| | B | | 9 | | 6 | | 1 | 2.4 | 2.4 |
| PPD derivative 15 | A | | 14 | | 1 | | 3 | 3.1 | 2.2 |
| | B | | 9 | | 0 | | 1 | 0 | 0 |

According to the Red-Green-Blue (RGB) Index, the values were converted as follows in Table 14B.

TABLE 14B

RGB index. TYPES: A: derivative only, B: derivative with $H_2O_2$, C: derivative with resorcinol.

| Analogues | | R | G | B |
|---|---|---|---|---|
| | Natural hair | 26 | 25 | 26 |
| | Bleach Hair | 206 | 184 | 145 |
| PPD | 1A | 200 | 177 | 135 |
| | 1B | 62 | 31 | 37 |
| | 1C | 26 | 25 | 26 |
| PPD derivative 1 | 2A | 29 | 28 | 31 |
| | 2B | 26 | 25 | 26 |
| | 2C | 26 | 25 | 26 |
| PPD derivative 2 | 3A | 34 | 57 | 54 |
| | 3B | 75 | 83 | 81 |
| | 3C | 67 | 63 | 64 |
| PPD derivative 3 | 4A | 26 | 25 | 26 |
| | 4C | 34 | 35 | 54 |
| PPD derivative 4 | 5A | 30 | 38 | 32 |
| | 5C | 60 | 42 | 48 |
| PPD derivative 5 | 6A | 29 | 28 | 31 |
| | 6B | 26 | 25 | 26 |
| | 6C | 26 | 25 | 26 |

As it can be seen from Tables 14A and 141B, PPD alone has values close to the bleached hair, meaning that it is unable to stain the hair on its own. Conversely, when used in combination with other agents, it provided an intense color (similar to natural black hair). The test PPD derivatives used herein showed RGB index values comparable to natural black hair, even without the additional oxidation provided by hydrogen peroxide. This suggests the feasibility of having one product in a single bottle—without the need for a peroxide or a coupling compound, such as resorcinol.

Example 16

Assessment of Skin Penetration and Interactions of PPD Analogues with Proteins & Enzymes Methods Skin Permeation/Penetration Porcine ears were generously provided by the NUS Department of Surgery. The ears were frozen at −80° C. until use (up to 3 months) and thawed at room temperature on the day preceding the experiment. Prior to the experiment, the skin was separated from the cartilage and dermatomed to a thickness of ~1.0 mm using an Acculan™ 3Ti dermatome (Aesculap, Inc., B. Braun, USA).

The PPD and derivatives were dissolved in deionized water at 1% w/v. The PPD and PPD derivatives 1-5 solutions were purged with argon gas to minimize oxidation of the donor solution.

Skin penetration studies were carried out using vertical Franz diffusion cells (PermeGear, USA) immersed in a 37° C. water bath. The donor and receptor volumes were 900 □L and 5 mL, respectively; the mean surface area of penetration was 0.64 cm². Upon insertion of the skin pieces into the Franz cells, the skin was equilibrated for 45 min with PBS in the receptor compartment. After equilibration, the skin's trans-epidermal water loss (TEWL) was measured using an Aquaflux AF300 (Biox, UK) to assess the integrity of the skin's stratum corneum barrier. The donor solution, consisting of PPD or derivative 1-5 (n=3 Franz cells each), was then added to the donor compartment and the penetration experiments were conducted for 8 h. The receptor solutions were continuously stirred with magnetic stirrers. At fixed time points, aliquots of 200 μL were taken from the receptor solution of each cell and the receptor solution topped up with 200 μL of fresh PBS. At the end of the experiment, the donor and receptor solutions were removed and the cells dismantled. For the purpose of mass balance on the PPD, PPD derivatives 1-5 the skin pieces and swabs of their outer surfaces were collected and stored in acetonitrile for PPD or derivative 1-5 extraction. The donor solution as well as PBS used to thoroughly wash each part of the Franz cells were also collected.

PPD, PPD derivatives 1-5 and metabolite concentrations in all permeation and mass balance samples were measured by LCMS. PPD steady state fluxes and permeability coefficients were calculated by fitting the solution to Fick's second law of diffusion at the steady state to the linear part of each experimental cumulative amount curve.

LCMS

Figure 4:
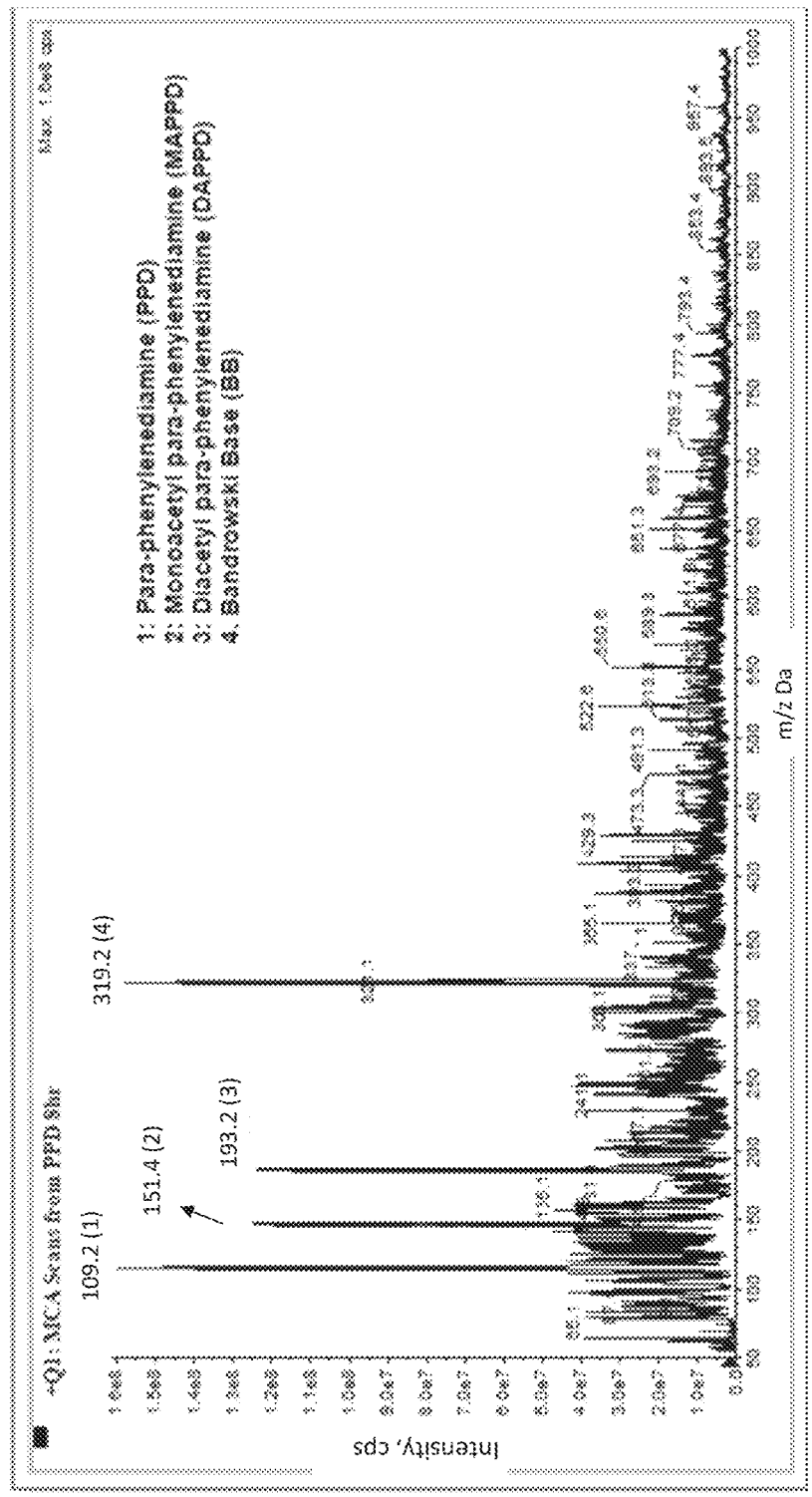
Figure 5:
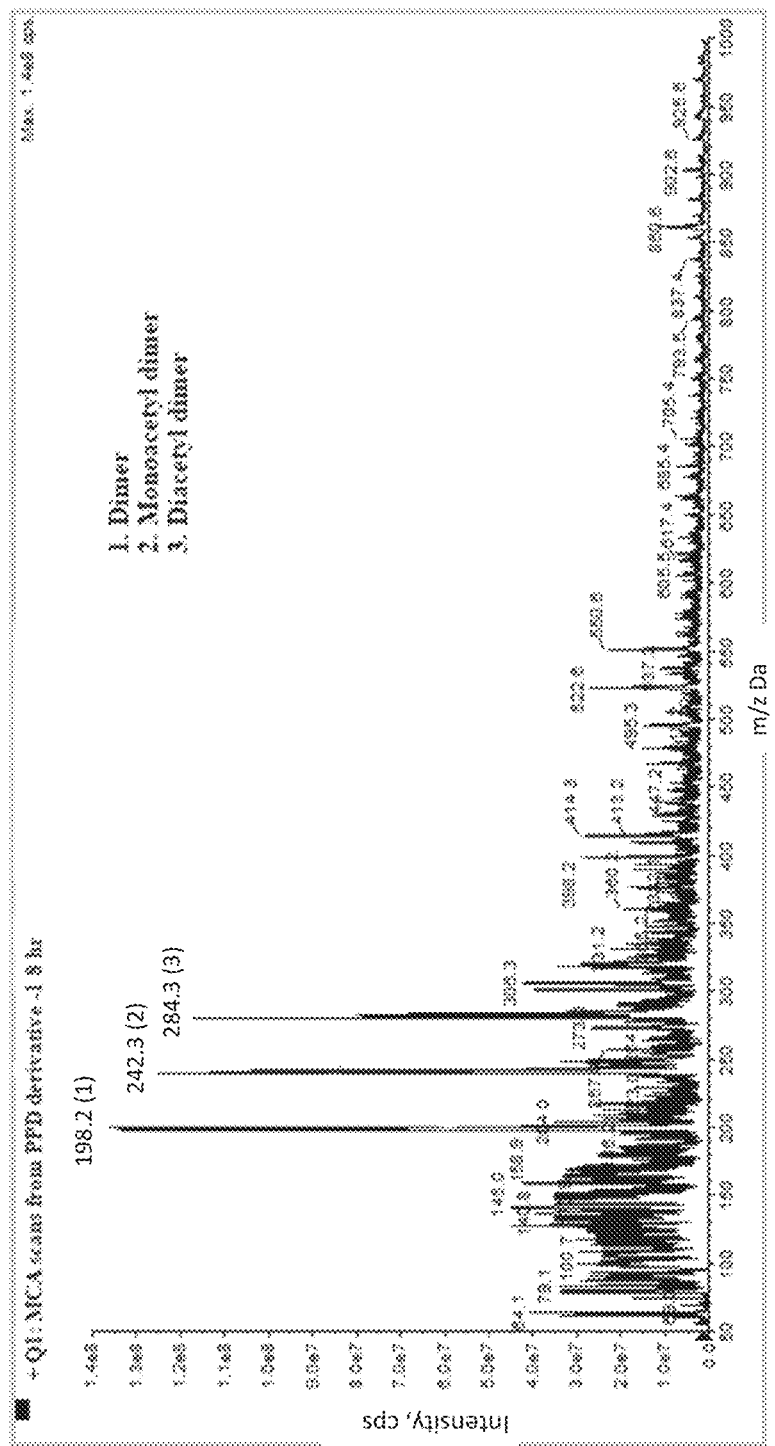

The validated method LCMS was applied to quantify PPD, PPD derivative 1-5 and metabolites from skin permeation study samples. FIGS. 3 and 4 show LCMS spectra for the identification of PPD and PPD derivatives 1 and 2 and metabolites from skin permeation study experiment.

Raman Spectroscopy

Solutions of PPD and derivatives in deionized water (1% w/v) were applied to samples of organotypic (OTC) skin developed in the PB group (IMB, A*STAR). Following a 30 min exposure at room temperature, the solution was gently washed off the OTC pieces using PBS. The OTC pieces were placed on the window of a confocal Raman spectroscope (gen2-SCA, RiverD, Netherlands) for spectroscopy in the fingerprint (400-1800 cm$^{-1}$) region. Reference spectra of the solutions were obtained and incorporated into the analysis software (SkinTools 2.0, RiverD, Netherlands) for regression fits to the skin OTC Raman spectra.

Results and Discussion

Skin Permeation

Thicknesses and TEWL values of the porcine ear skin pieces are reported in Table 15. Both parameter values are consistent across the skin pieces. TEWL values are somewhat higher that the cut-off value used of 13 gm$^{-2}$h$^{-1}$ in published in vitro experiments. We expect more precise handling of the skin and a longer equilibration time (1 hour) to further reduce the TEWL values.

TABLE 15

Thickness and TEWL values measured prior to the permeation experiment. Skin pieces #1-3 were used for PPD permeation, skin pieces #4-6 for the PPD derivative 1.

| Skin # | 1 | 2 | 3 | 4 | 5 | 6 | Mean ± SD |
|---|---|---|---|---|---|---|---|
| Thickness [mm] | 1.10 | 1.22 | 1.04 | 1.01 | 1.01 | 0.94 | 1.05 ± 0.09 |
| TEWL [g m$^{-2}$ h$^{-1}$] | 16.0 | 14.9 | 16.0 | 15.3 | 20.5 | 17.6 | 16.7 ± 1.88 |

PPD and its metabolites were detected post skin permeation, however with different trends in the amount present with respect to time. PPD and its metabolites were already present within the first 30 mins on skin exposure to PPD, and this could be attributed to the fast permeation of PPD through the skin.

Figure 7:
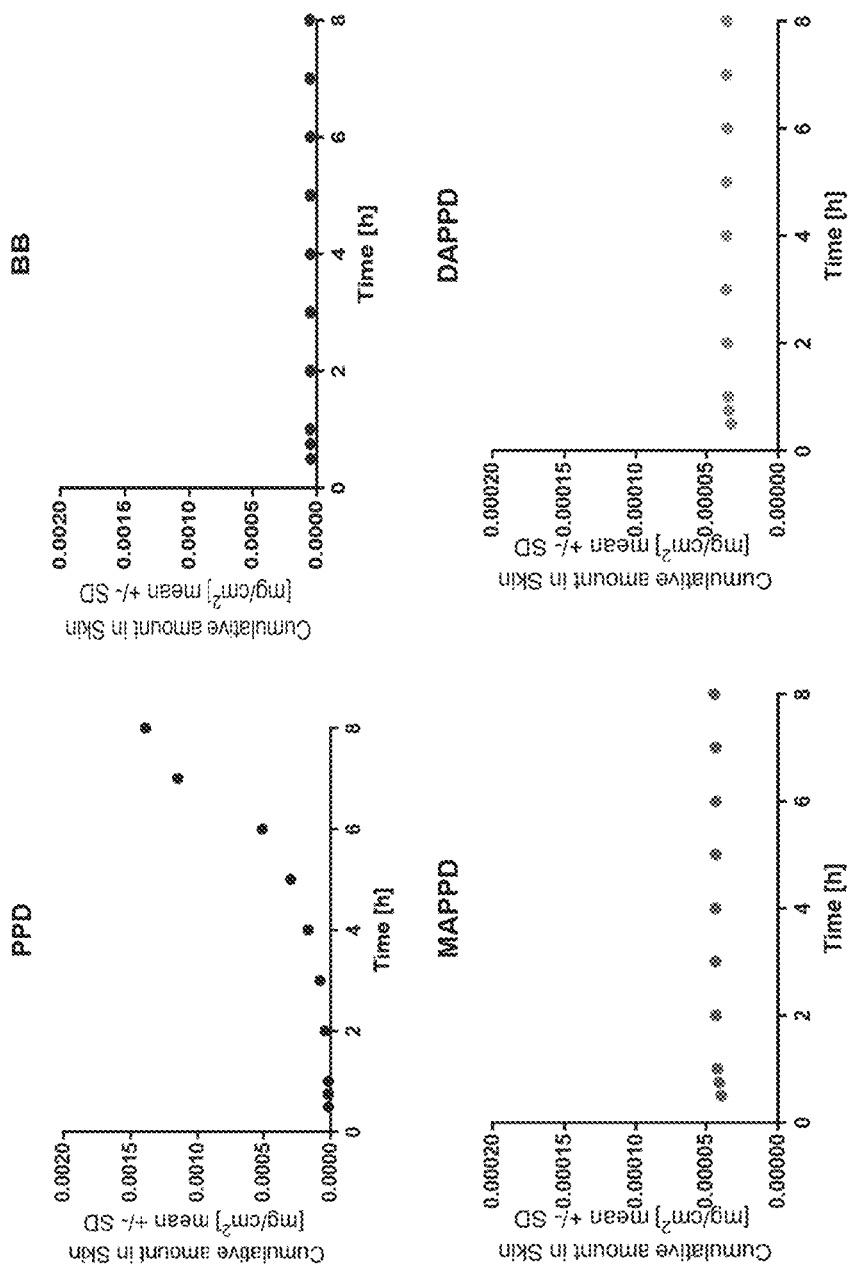

FIG. 7 shows the PPD and associated metabolite cumulative amount profiles obtained after the 8 h permeation experiments. Mass balances on PPD in the Franz cells (>99%) indicated that most of the PPD and Bandrowski's base were recovered in each Franz cell.- The PPD transport parameters calculated from the data in FIG. 7 are summarized in Table 16.1. BB, DAPPD and MAPPD permeation through the skin into the receptor were significantly smaller than PPD permeation.

TABLE 16.1

PPD steady state transport parameter
means and standard deviations (parentheses).

| $K_{s/d}$ | $D_m \cdot 10^4$ [cm$^{-2}$ h$^{-1}$] | $t_{lag}$ [h] | $J_{ss} \cdot 10^4$ [mg cm$^{-2}$ h$^{-1}$] | $k_p \cdot 10^5$ [cm h$^{-1}$] |
|---|---|---|---|---|
| 0.010 (0.0003) | 5.00 (0.58) | 4.2 (0.20) | 4.3 (0.27) | 4.3 (0.26) |

$K_{s/d}$: skin-donor partition coefficient,
$D_s$: diffusion coefficient in skin,
$t_{lag}$: lag time,
$J_{ss}$: steady state flux,
$k_p$: steady state permeability coefficient.

Figure 8:
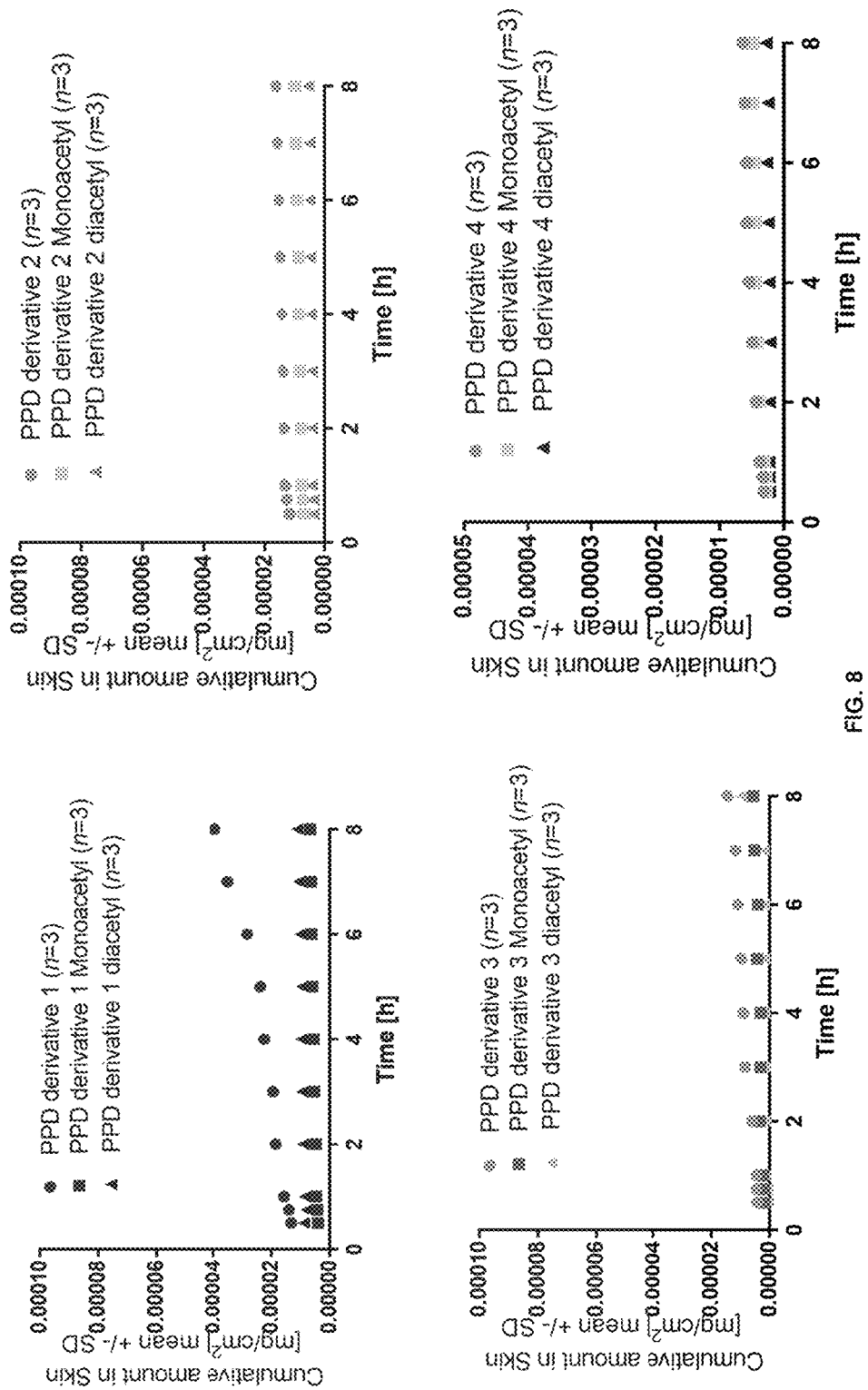

FIG. 8 juxtaposes the PPD derivatives and their metabolites (monoacetyl & diacetyl) permeation (a. derivative 1, b. derivative 2, c. derivative 3, d. derivative 4)

Figure 9:
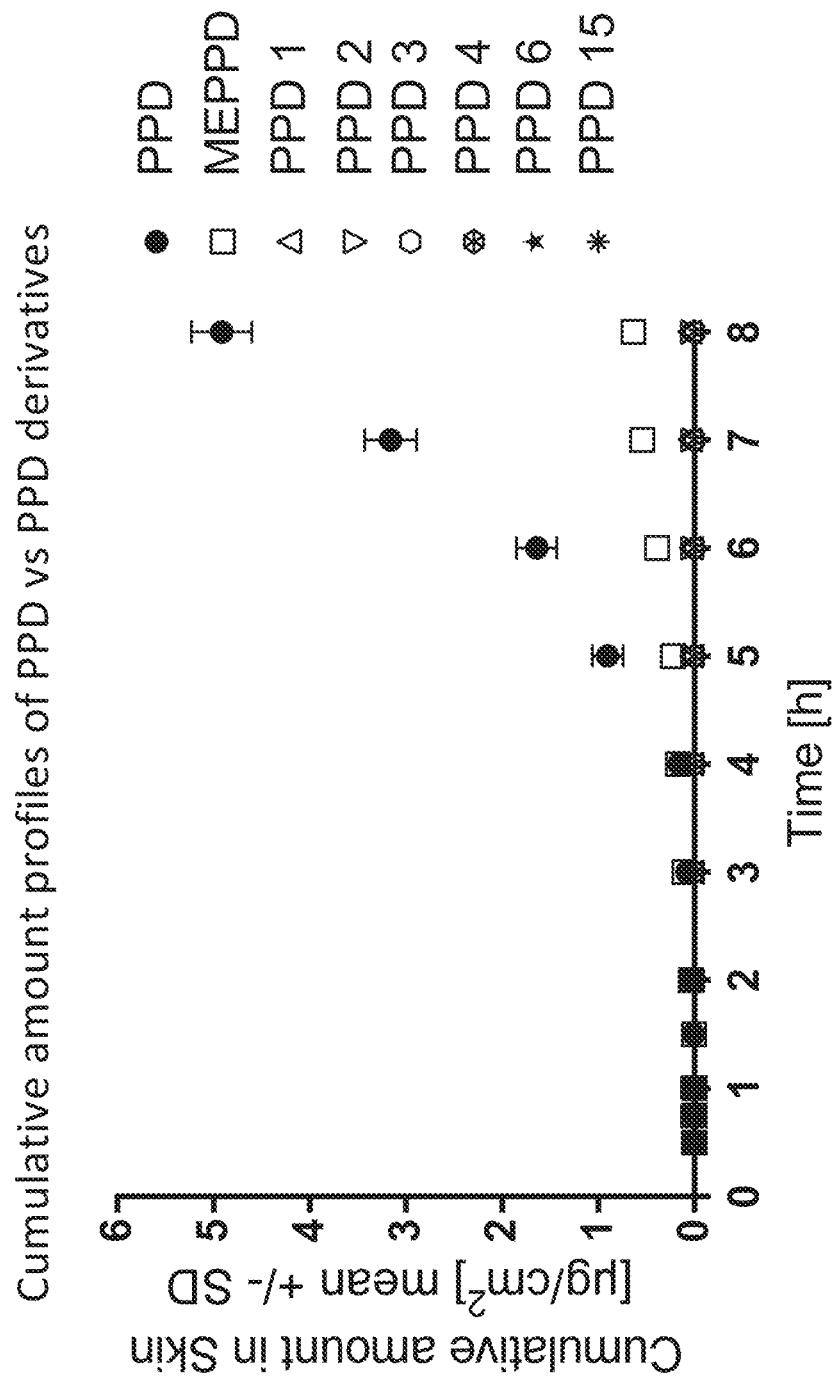

FIG. 9 shows the cumulative amount comparison profile of PPD vs PPD derivatives. As shown in FIG. 9, PPD displayed a higher extent of permeation than MEPPD throughout the course of the experiment. In fact, none of the derivatives permeated at a higher level than PPD at any time points.

Importantly, at the end of the 8 h experiment, PPD had the highest extent of skin permeation amongst the tested compounds, being about 7.5 times greater than ME-PPD (which showed the second highest extent of skin permeation). MEPPD showed 8 fold decreased permeation than PPD in view of increased Log P and molecular weight (which are factors reported to be inversely correlated with the extent of skin permeation, for example, see Magnusson, B. M., et al., Journal of Investigative Dermatology, 2004. 122(4): p. 993-999). MEPPD has the second highest skin permeation (see Table 16.3) and this is due to a marked decrease in its melting point (88-90° C.), relative to the other compounds. It is known that an inverse relationship between melting point and skin permeability exists, as compounds with lower melting points tend to have a higher solubility in skin lipids, resulting in increased percutaneous absorption (for example, see Yuan, X. and A. C. Capomacchia, Journal of Pharmaceutical Sciences, 2013. 102(6): p. 1957-1969; and Golla, S., et al., Chemical Biology and Drug Design, 2012. 79(4): p. 478-487).

With regards to our series of compounds, an increase in the chain length at ortho position (compounds 3-6 and 15) of PPD and substitution of symmetrically amine capped PPD derivatives 1 and 2 could result in a several fold decrease in the permeation. In our PPD series, the effect of increased log P (>1.5 except for PPD 1), molecular weight (>200 except for PPD 1) and melting point (>150° C. for all our compounds) (Table 16.3), correlated with a decrease in permeation across the skin membrane throughout the 8 h duration of experiment. As shown in Table 16.2, PPD 1 permeated 51 times less than PPD, PPD 2 permeated 93 times less than PPD. PPD derivatives 3,4 permeated 360-503 times less than PPD. PPD 5 is impermeable through porcine skin and PPD 6 and 15 permeated about 2 order of magnitude less than PPD.

TABLE 16.2

Mass balance profile of PPD and PPD derivatives.

| Parent compound | % dose applied | % converted to metabolite (mean) | % Parent compound Recovery (mean) | % Parent compound Penetrated (mean) | Penetration profile PPD vs derivatives |
|---|---|---|---|---|---|
| PPD | 1% W/V | 3.17 | 90.27 | 0.162 | |
| PPD 1 | 1% W/V | 0.0104 | 93.85 | 0.00314 | 51.6 |
| PPD 2 | 1% W/V | 0.008 | 96.4 | 0.00173 | 93.6 |
| PPD 3 | 1% W/V | 0.0123 | 94.5 | 0.00045 | 360 |
| PPD 4 | 1% W/V | 0.0121 | 94.34 | 0.000322 | 503.1 |
| PPD 5 | 1% W/V | 0.0118 | 98 | 0 | N/A |
| PPD 6 | 1% W/V | 0.01 | 95.4 | 0.00015 | 1080 |
| PPD 15 | 1% W/V | 0.0108 | 96.7 | 0.0001 | 1620 |
| MEPPD | 1% W/V | 0.019 | 95.39 | 0.02 | 8.1 |

TABLE 16.3

Physico-chemical properties of PPD derivatives.

| Compound | logP o/w | Mol Wt | Melting point (° C.)[a] | HBA | HBD | PSA |
|---|---|---|---|---|---|---|
| PPD | −0.61 | 108.14 | 145.3-147.3 (±0.26-0.11) | 2 | 4 | 52.04 |
| PPD 1 | 0.93 | 199.25 | 158.7-160.2 (±0.78-0.15) | 3 | 5 | 64.07 |
| PPD 2 | 1.86 | 290.36 | >300 | 4 | 6 | 76.1 |
| PPD 3 | 2.56 | 236.35 | 225-226 (±0.3-0.4) | 3 | 4 | 61.27 |
| PPD 4 | 2.14 | 208.3 | 204.2-205.2 (±0.36-0.2) | 3 | 4 | 61.27 |
| PPD 5 | 2.21 | 299.41 | 182.5-183.5 (±0.2-0.3) | 4 | 4 | 78.34 |
| PPD 6 | 3.18 | 327.41 | 180.0-181.0 (±0.1-0.2) | 3 | 3 | 47.28 |
| PPD 15 | 2.94 | 236.31 | 176-177.0 (±0.2-0.3) | 3 | 3 | 36.09 |
| MEPPD | −0.90 | 152.19 | 88.3-90.3 (±0.25-0.35) | 3 | 4 | 61.27 | logPo/w: partition coefficient of the compound in octanol/water.
HBA: Hydrogen bond acceptor;
HBD: Hydrogen Bond Donor;
PSA: polar surface area.
[a]Experiments were performed in triplicate.

The visual aspect of the porcine skin at the end of the PPD and PPD derivatives experiments were compared. While the skin exposed to PPD has turned brown or black in colour due to formation of the Bandrowski's base, the skin exposed to the derivatives 1-4 is unstained, with no formation of Bandrowki's base.

Raman Spectroscopy

Figure 10:
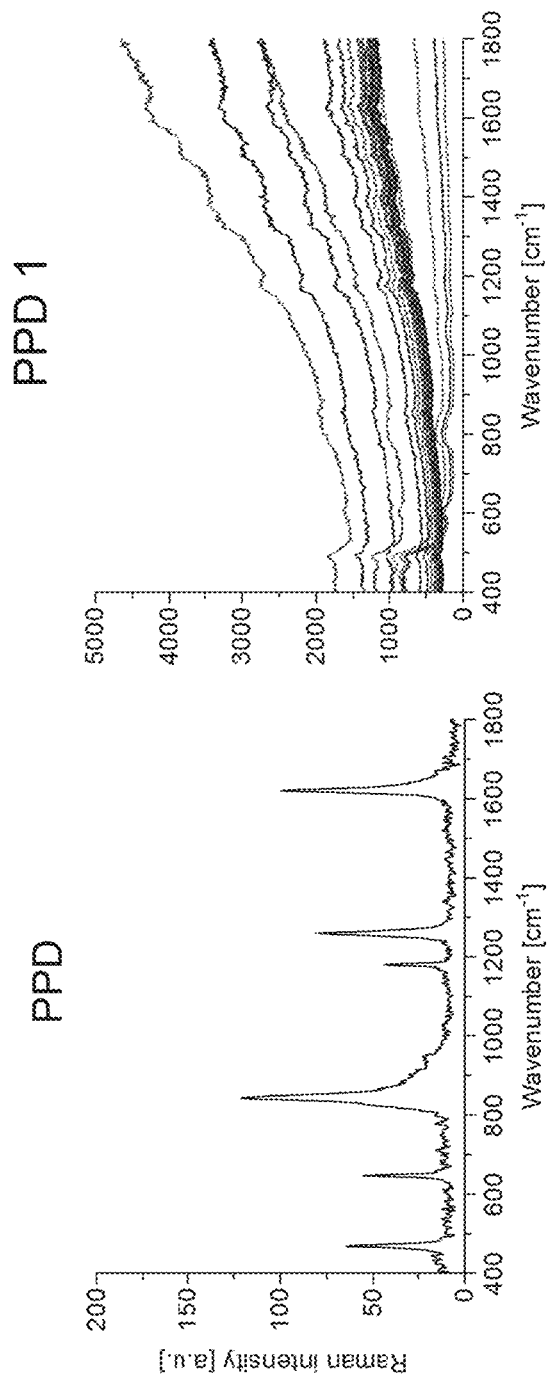

FIG. 10 shows the reference Raman spectra of PPD and the –PPD 1. Whereas the PPD spectrum shows peaks at distinct wavenumbers, in agreement with literature data, the dimer spectrum is broad without any distinct maxima. The dimer spectrum is typical of polymeric compounds, where multiple 3D molecular configurations give rise to a variety of vibrations and indistinct Raman spectra.

Figure 11:
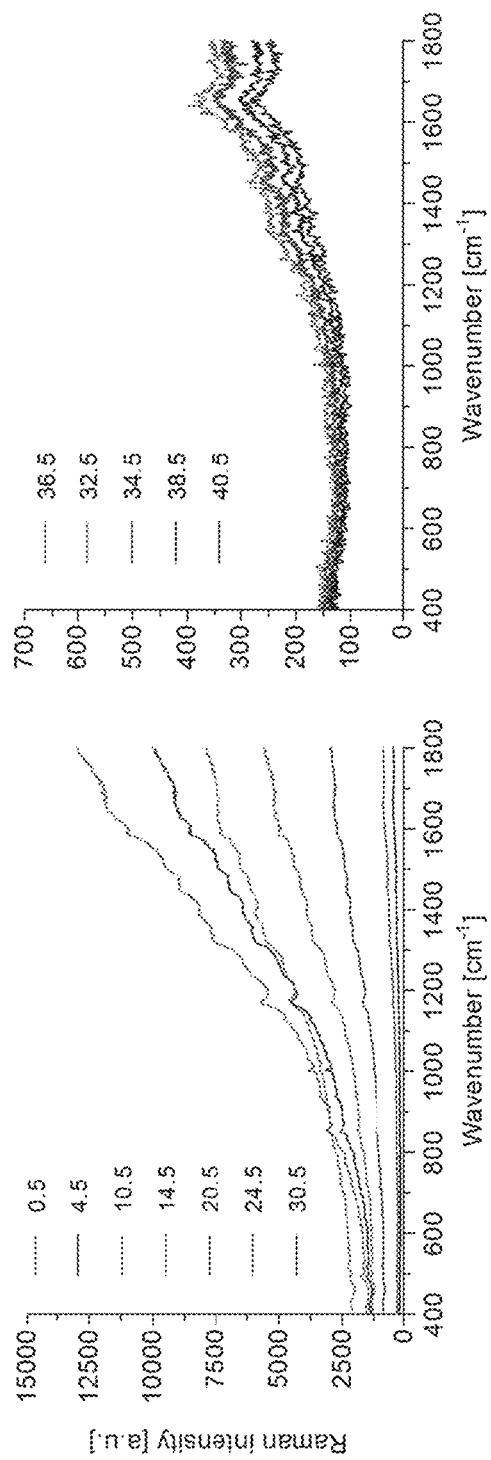

In skin OTC, the dimer yields qualitatively similar spectra to the solution, masking any of the Raman peaks associated with skin at each skin depth (FIG. 11). Further work is required to determine whether the dimer and intrinsic skin spectra can be deconvoluted, and if the trimer gives a similar profile.

Example 17

In Vitro Cell Cytotoxicity Assay on HaCaT Cells

Material

HaCaT (human, adult, low calcium, high temperature, human adult skin keratinocytes) cells were obtained from the IMB (Institute of Medical Biology) Skin Cell Bank. Fetal bovine serum (FBS), Dulbecco's minimum essential medium (DMEM) and trypsin EDTA solution were purchased from GE healthcare life sciences, Utah. Penicillin/streptomycin, dimethyl sulfoxide (DMSO), and phosphate buffered saline (PBS) were from Fisher Scientific (Singapore). Para-phenylenediamine (PPD) was purchased from Sigma Aldrich (Singapore). PPD analogues such as Dimer, trimer, ethyl hexyl para-phenylenediamine (EHPPD), hexyl para-phenylenediamine (HPPD), Bandrowski base (BB) were synthesized in house.

Cell Culture and Incubation

Cell viability was essentially determined using the MTT assay as described in the literature. The HaCaT cells were grown in DMEM with 10% FBS and 1% penicillin/streptomycin. The cells in T-75 $cm^2$ culture flasks were incubated with 5% $CO_2$ at 37° C. in a humidified incubator. The HaCaT cells were grown to expected confluency and then they were harvested by trypsinizing the cell with 0.25% trypsin/EDTA and incubated at 37° C. for 5 min to obtain the complete cell detachment. After the incubation, cell pellets were resuspended, and washed twice with 1×PBS. The cell suspension in 1×PBS was counted and adjusted to $1 \times 10^5$/mL. A HaCaT keratinocyte suspension (100 μL in 1×PBS) with a cell concentration of $1 \times 10^5$ cells/mL) and a test solution (100 μL in milli-Q water) were combined in each well of two 96-well plates. Test solutions with a desired concentration were prepared by serial dilutions of the stock solutions with 1×PBS.

For the cytotoxicity experiment, cells were seeded at a density of $5 \times 10^3$ in 200 ul of medium into each well of 96-well plates. Cells were seeded as three sets of four replicates for each concentration. After 24 h of incubation, the cells were washed with PBS and cultured for 72 h with 200 ul of 10% FBS containing DMEM medium, together with the different concentrations of the test compounds ranging from 500 μM to 1.9 μM for PPD and analogues 1-5 and standard in a serial dilution. Then the medium was removed and 100 μl of MTT [3-(4,5-dimethylthiazol-2yl)-2,5-diphenyl-2H-tetrazolium bromide](1 mg/ml) (Alfa Aesar, Singapore) in PBS was added. At the end of 4 h incubation, the plates were removed from the incubator and plates were shaken for 5 min. The absorbance at 570 nm was determined using Bio-Tek plate reader. The cell viability rates were calculated from absorbance readings and represented as percentages of control value (untreated cells).

Figure 6:
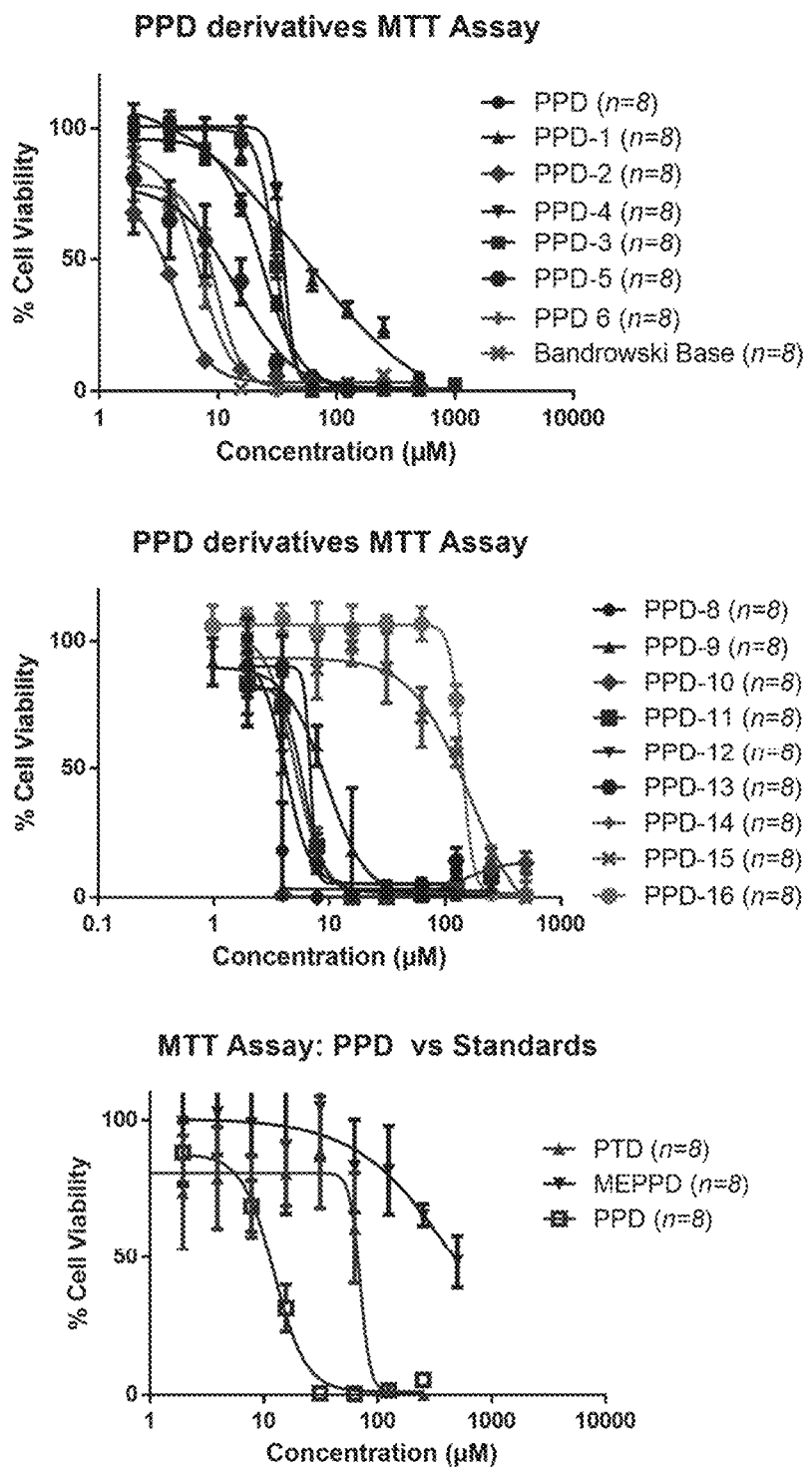

Establishment of a universal positive control for these studies was challenging because of the potency of the positive control towards the HaCaT cells is weaker for most of the compounds tested. As shown in the Table 17, in total 5 positive control compounds were tested for the cytotoxic property. Among the compound tested, Simvastatin (11) was selected as positive control for this study with the $IC_{50}$ value of 9.15 μM as other compounds neglected due to solubility issues and weaker inhibitory potency. Examples of concentration-response curves for PPD dye compounds in HaCaT cells are shown in FIG. 6.

TABLE 17

| No | Hair Dye compounds | $IC_{50}$ |
|---|---|---|
| 1 | p-Phenylenediamine | 23.50 μM |
| 2 | PPD derivative 1 | 49.3 μM |
| 3 | PPD derivative 2 | 4.14 μM |
| 4 | PPD derivative 3 | 31.0 μM |
| 5 | PPD derivative 4 | 34.83 μM |
| 6 | PPD derivative 5 | 14.3 μM |
| 7 | PPD derivative 6 | 10.5 μM |
| 8 | PPD derivative 8 | 6.92 μM |
| 9 | PPD derivative 9 | 6.8 μM |
| 10 | PPD derivative 10 | 1.8 μM |
| 11 | PPD derivative 11 | 6.4 μM |
| 12 | PPD derivative 12 | 4.3 μM |
| 13 | PPD derivative 13 | 5.2 μM |
| 14 | PPD derivative 14 | 5.4 μM |
| 15 | PPD derivative 15 | 160.5 μM |
| 16 | PPD derivative 16 | 139.5 μM |
| 17 | para-toluenediamine (PTD) | 73.10 μM |
| 18 | 2-(methoxymethyl)benzene-1,4,-diamine (MEPPD) | 543.5 μM |
| 19 | Bandrowski Base | 6.09 μM |
| | Positive Controls | |
| 20 | Menadione | 3.56 μM |
| 21 | Tertbutylhydroquinone | 27.87 μM |
| 22 | Doxorubicin | <390 nM |
| 23 | Diethylmaleate | >100 μM |
| 24 | Simvastatin | 28.6 μM (9.15 μM)* |

*The $IC_{50}$ of 9.15 μM was based on an old batch of simvastatin, which appeared to show stability issues. When replaced with a new batch of simvastatin, the $IC_{50}$ value of 28.6 μM was consistently obtained.

Results & Discussion

FIG. 6 shows the viability of human skin HaCaT keratinocytes exposed to several concentrations of a PPD and its analogues in PBS along with the control without test compounds. Based on the immediate cell viability data shown in FIG. 6 and the cell viability percentage listed in Table 17, PPD 1 showed an IC50 value of 49.3 μM. This is almost a 2-fold increase in the IC50 value as compared to PPD, which displayed an IC50 value of 23.5 μM, suggesting that the increase from a monomer (PPD) to a dimer (PPD 1) was less cytotoxic. This was further confirmed by other monomeric compounds, PPD 3 & PPD 4, with an IC50 of 31.0 and 34.8 μM: their profile was intermediate between PPD and the dimeric PPD 1, suggesting that substituents at the ortho position are beneficial to cells, especially when a long chain is used, although less favourable than a dimeric structure. The further addition of an aromatic group (from dimer to trimer) proved to be detrimental to cells: indeed, the trimer PPD 2 exhibited high cytotoxicity, with the lowest IC50 value of 4.14 μM, leading to a 6-fold increase in the cytotoxicity profile as compared to PPD 1. Not surprisingly, comparable results were observed for BB (IC50 value of 6.09 μM), which is also trimeric in nature. On the other hand, PPD 16, which differs from PPD 4 in the additional substitution at one of the NH2 groups with an alkyl chain, had a high IC50 value of 139.5 µM, indicating that the amino groups should be substituted to reduce cytotoxicity. Interestingly, ortho substitution with an ester (PPD 15, IC50=160.5 uM) further ameliorated the cell viability by about 5 times in comparison to PPD 4. Derivatives 11-14 showed lower IC50 values, similar to derivatives 9 & 10, indicating that further amine conjugations to the amino groups of dimeric PPD 1 will have a detrimental effect on cells. MEPPD displayed the highest IC50 value of 453.5 µM, which is a 19-fold increase compared to PPD, most likely due to stronger electron-donating groups than 3 & 4 at the ortho position.

Example 18

Direct Peptide Reactivity Assay for Determination of Skin Sensitization Potential The elicitation of allergy involves an initial exposure of the chemical or hapten to the skin and then binding of the chemical to a protein carrier in a process known as haptenisation. Mostly, the chemical allergens possess electrophilic moiety or can be converted to electrophiles (reactive metabolites) enzymatically. Direct Peptide Reactivity Assay (DPRA) was first invented by Frank Gerberick and colleagues in 2004[1] and was further developed in 2007 (Gerberick et al., 2007). DPRA is designed to mimic the covalent binding of electrophilic chemicals to nucleophilic centres in skin proteins by quantifying the reactivity of chemicals towards the model synthetic peptides containing cysteine and lysine.

The results of the use of DPRA in published studies suggest that the accuracy of DPRA in discriminating between non-sensitisers and sensitisers is 80%, with a sensitivity of 80% and a specificity of 77%, when compared with the local lymph node assay (LLNA).

The reactivity type of each derivative was assessed based on the following prediction model provided by Table 18.

TABLE 18

Recommended classification of reactivity class and sensitisation potential based on the DPRA data (cysteine 1:10/lysine 1:50 model). Depletion of the DPRA peptides can be used to classify chemicals into four different categories of reactivity allowing discrimination between non-sensitising and sensitising chemicals.

| Mean of cysteine and lysine % depletion | Reactivity Class | DPRA prediction |
| --- | --- | --- |
| 0% ≤ mean % depletion ≤ 6.38% | No or minimal activity | Negative |
| 6.38% ≤ mean % depletion ≤ 22.62% | Low activity | |

TABLE 18-continued

Recommended classification of reactivity class and sensitisation potential based on the DPRA data (cysteine 1:10/lysine 1:50 model). Depletion of the DPRA peptides can be used to classify chemicals into four different categories of reactivity allowing discrimination between non-sensitising and sensitising chemicals.

| Mean of cysteine and lysine % depletion | Reactivity Class | DPRA prediction |
| --- | --- | --- |
| 22.62% ≤ mean % depletion ≤ 42.47% | Moderate activity | |
| 42.47% ≤ mean % depletion ≤ 100% | High reactivity | Positive |

In the Direct Peptide Reactivity Assay, peptide depletion is generally performed with cysteine peptide with different test chemicals following 20 mins and 24 h co-incubation period, respectively. Reactivity with lysine peptide has been suggested as an important mechanism for generating modified protein targets in Allergic Contact Dermatitis (ACD) (see Alvarez-Sanchez, R., et. al., Chem. Res. Toxicol. 16, 627-637; Eilstein, G, A. et. al, Bioorg. Med. Chem. 16, 5482-548; Gerberick, F. et. al. The report and recommendations of ECVAM Workshop 64. ATLA). Although many chemical sensitizers are reactive toward thiol-containing molecules, formation of antigenic structures due to lysine reactivity may have synergistic effects on the amount and diversity of modified protein products. It is proved that haptens covalently linked to lysine residues have been shown to play a role in MHC recognition and activation of T lymphocytes (Weltzien, H. U., et. al., Toxicology, 107, 141-151). Characterizing the potential for chemical-induced modification of lysine in chemico may contribute to the development of an integrated testing strategy for risk assessments.

Direct Lysine- and Cysteine-Peptide Incubation Conditions.

Sample Processing and Analysis by HPLC/MS/MS.

Direct reactivity of test chemical to lysine-based synthetic peptide was determined in reactions containing 100 mM ammonium acetate buffer (pH 10.2). The final concentration of lysine peptide was 20 µM in a final reaction volume of 0.3 ml. Direct reactivity of test chemicals to cysteine-based synthetic peptide was determined in 100 mM Sodium Phosphate buffer of pH 7.5. Similar to Lysine DPRA, the final concentration of cysteine peptide was 20 µM in a final reaction volume of 0.3 ml. Further details of the reaction set-up are provided in Table 19.

TABLE 19

DPRA reaction set up.

| | | Compound | Initial Concentration (µM) | Aliquot volume (µL) | Final concentration (µM) | Final Volume (µL) |
| --- | --- | --- | --- | --- | --- | --- |
| Lysine | 1 | Ammonium Acetate Buffer | — | 225 | | 300 |
| | 2 | Lysine | 200 | 30 | 20 | |
| | 3 | Deferoxamine Mesylate | 100 | 30 | | |
| | 4 | Test Compound | 20,000 | 15 | 1000 | |
| Cysteine | 1 | Sodium Phosphate Buffer | — | 237 | — | 300 |
| | 2 | Cysteine | 200 | 30 | 20 | |
| | 3 | Deferoxamine Mesylate | 100 | 30 | | |
| | 4 | DL-dithiothreitol | 16 mM | | | |
| | 5 | Test Compound | 20,000 | 3 | 200 | |

For the DPRA, incubation mixtures were prepared using each peptide to test compound ratios of both 1:10 for cysteine peptide and 1:50 for lysine peptide, according to Table 19. Deferoxamine mesylate and peptide solutions were prepared freshly before the start of the experiment. Sample reactions were initiated by adding 3 µl of a test chemical stock solution for cysteine and 15 µl stock solution for lysine peptide. These mixtures were then placed in a temperature-controlled shaking incubator at 25° C.

At each time point (20 mins/24 hours), the incubation mixtures were quenched with 75 µL of 95% ACN/H$_2$O, and mildly vortexed (600 rpm, 3 seconds). For Lysine DPRA experiment, 10 µl of aliquot was diluted with 2% ACN/H$_2$O, vortexed and stored at −80° C. until analysis by LC-MS/MS. For cysteine DPRA, an additional step was performed. 10 µl of cysteine reaction mixture, at time points 20 min and 24 h were diluted in 180 µl of 2% ACN/H$_2$O. To which, a 10 µl aliquot of a 16 mM dithiothreitol solution (prepared in water) was then added, and samples were heated in a 45° C. oven for 30 min, then allowed to cool to room temperature prior to analysis. The peptide depletion (PD) percentage was obtained using this equation.

$$\% \text{ Peptide depletion} = \frac{\text{Mean peak area of control samples} - \text{Peak area of test compound}}{\text{Mean peak area of control samples}} \times 100$$

Analysis was designed to selectively monitor two analytes: the cysteine peptide (monomer) and leucine enkephalin internal standard (IS) and, in a separate method, the lysine peptide and IS. The LC-MS/MS methodology employed an Agilent 1290 Infinity ultra-high pressure liquid chromatography (UHPLC) binary pump, autosampler, vacuum degasser, and column oven (Agilent Technologies Inc., Santa Clara, Calif., USA) and ACQUITY UPLC BEH C18, 1.7 µM, 2.1×100 mm column (Waters, Mildord, Mass., USA), were used for chromatographic separations. The mass spectrometric analysis was performed by use of a AB SCIEX QTRAP 5500 tandem mass spectrometry (MS/MS) system (AB SCIEX, Framingham, Mass., USA) operating in triple quadrupole positive mode (ESI+) equipped with an AB Sciex Turbo Ion Spray interface. Acquisition and analysis of data were performed with Analyst software ver. 1.6.2 (Applied Biosystems).

Results

Direct peptide reactivity assay (DPRA) was used in this study to evaluate PPD derivatives according to the reactivity classes and sensitizing potential reported in literature. Two model heptapeptides containing nucleophilic aminoacids such as cysteine (Ac-RFAACAA-COOH, 96.05%) and Lysine (Ac-RFAAKAA-COOH, 95.5%) containing heptapeptide have been chosen as surrogate protein and the usage of these peptides has also been validated. Mean percent depletion values of cysteine (1:10) and lysine (1:50) is recommended by OECD as proper model for predicting skin sensitization potential of the haptens or prohaptens. For an allergen to elicit a positive skin reaction, it must first penetrate the stratum corneum of the skin, and then react with skin proteins to form immunogenic haptens. Here, we studied PPD, an established skin sensitizer, and its novel derivatives, carefully designed with higher molecular weight (thus, a bigger molecule), high log P, increased hydrogen bonding capability, increased electron density by ortho position electron donating substituents and decreased oxidation susceptibility to lower the skin sensitizing potentials.

DPRA conducted at 24 h allows classification and comparison of substances according to their skin sensitizing potentials. DPRA at 20 min, however, was conducted by us to simulate the hair dyeing time in salon. We hypothesised that our PPD derivatives will have lower sensitizing potentials compared to PPD owing to their molecular structure with suitable substituents possessing different electronic properties. PPD undergoes auto-oxidation to form an electrophilic imine intermediate that is reactive to nucleophilic amino acids. Similarly, for our PPD derivatives to be reactive to nucleophilic amino acids, such an imine intermediate is expected to form. However, by modifying and substituting the PPD at ortho position (PPD 3,4), and blocking the extension of conjugation with substituted benzyl groups (PPD 9-14) and long chain aliphatic group (PPD 16) at the one end of the amine functionality, we aimed to reduce the oxidation tendency of PPD in order to form no or less reactive imines, and thus, be less reactive than PPD.

Peptide depletion results on 5 PPD derivatives (PPD Derivative 1-5) using cysteine and lysine peptides are shown in tables 20-23. The ratios of peptide to chemical used were 1:10 for Cysteine and 1:50 for lysine. The results indicate correlation between allergenic potency and depletion of unreacted peptides. As seen in the Table 20, PPD showed low reactivity to cysteine for 20 mins; however, the reactivity of the PPD towards the cysteine increased substantially as time progress (Table 21). These data are in correlation with literature data. Among the newly synthesized PPD analogues, derivatives 3 and 4 showed moderate reactivity to cysteine at 20 mins. Interestingly, the reactivity of these derivatives did not increase after 24 hour incubation (Table 21). A similar trend was observed for the derivative 5.

TABLE 20

Direct Peptide Reactivity with PPD derivatives following 20 min Incubation with Cysteine Peptide

| Test Chemical | Concentration of peptide:Concentration of Test Chemical (1:10) % of Cysteine depletion at 20 min Cysteine (0.02 mM):Test Chemical (0.2 mM) | | | | |
|---|---|---|---|---|---|
| | Rep 1 | Rep 2 | Rep 3 | Avg | Reactivity Class |
| PPD | 16.2 | 14 | 15.2 | 15.1 | Low |
| Derivative 1 | 42.6 | 40.5 | 41.5 | 41.5 | Moderate |
| Derivative 2 | 55.6 | 53.6 | 52.6 | 54.0 | High |
| Derivative 3 | 32.4 | 32 | 31.4 | 31.9 | Moderate |
| Derivative 4 | 30.8 | 31.8 | 33.8 | 32.8 | Moderate |
| Derivative 5 | 50.9 | 52.9 | 49.9 | 51.2 | Moderate to High |

TABLE 20-continued

Direct Peptide Reactivity with PPD derivatives following 20 min Incubation with Cysteine Peptide Concentration of peptide:Concentration of Test Chemical (1:10)
% of Cysteine depletion at 20 min
Cysteine (0.02 mM):Test Chemical (0.2 mM)

| Test Chemical | Rep 1 | Rep 2 | Rep 3 | Avg | Reactivity Class |
|---|---|---|---|---|---|
| Bandrowski Base | 42.5 | 44.5 | 45.5 | 44.2 | High |
| p-Benzoquinone | 72.7 | 73.7 | 72.0 | 72.8 | High |
| Lactose | 0 | 0 | 0 | 0 | No or Minimal |

TABLE 21

Direct Peptide Reactivity with PPD derivatives following 24 h Incubation with Cysteine Peptide Concentration of peptide:Concentration of Test Chemical (1:10) % of Cysteine depletion at 24 h
Cysteine (0.02 mM): Test Chemical (0.2 mM)

| Test Chemical | Rep 1 | Rep 2 | Rep 3 | Avg | Reactivity Class |
|---|---|---|---|---|---|
| PPD | 77.7 | 78 | 77.2 | 77.6 | High |
| Derivative 1 | 69.5 | 69.6 | 69.3 | 69.4 | High |
| Derivative 2 | 65.6 | 65.6 | 61.2 | 64.1 | High |
| Derivative 3 | 34.8 | 31.7 | 31.8 | 32.7 | Moderate |
| Derivative 4 | 40 | 41 | 41.5 | 40.8 | Moderate |
| Derivative 5 | 53.5 | 53.8 | 54.1 | 53.8 | Moderate to High |
| Bandrowski Base | 71.8 | 69.9 | 70.4 | 70.7 | High |
| p-Benzoquinone | 89.6 | 89.5 | 90 | 89.7 | High |
| Lactose | 0 | 1 | 1 | 0.6 | No or Minimal |

TABLE 22

All replicate peptide depletion values for Lysine after 20 min of incubation with a Test Chemical.

Concentration of peptide:Concentration of Test Chemical (1:50) % of Lysine depletion at 20 min
Lysine (0.02 mM):Test Chemical (1 mM)

| Test Chemical | Rep 1 | Rep 2 | Rep 3 | Avg | Reactivity Class |
|---|---|---|---|---|---|
| PPD | 14.9 | 14.4 | 14.6 | 14.6 | Low |
| Derivative 1 | 7.89 | 6.48 | 9.01 | 7.79 | Low |
| Derivative 2 | 10.1 | 11.8 | 11.8 | 11.2 | Low |
| Derivative 3 | 5.07 | 5.63 | 7.89 | 6.2 | No or Minimal |
| Derivative 4 | 1.13 | 0.845 | 1.41 | 1.1 | No or Minimal |
| Derivative 5 | 6.76 | 5.92 | 6.2 | 6.3 | No or Minimal |
| Bandrowski Base | 9.58 | 7.89 | 2.54 | 6.7 | Low |
| p-Benzoquinone | 22.5 | 20.6 | 20 | 21.0 | Low |
| Lactose | 0 | 0 | 0 | 0 | No or Minimal |

TABLE 23

All replicate peptide depletion values for Lysine after 24 h of incubation with a Test Chemical.

Concentration of peptide:Concentration of Test Chemical (1:50) % of Lysine depletion at 24 h
Lysine (0.02 mM):Test Chemical (1 mM)

| Test Chemical | Rep 1 | Rep 2 | Rep 3 | Avg | Reactivity Class |
|---|---|---|---|---|---|
| PPD | 32.8 | 33.1 | 33.9 | 33.3 | Moderate |
| Derivative 1 | 21 | 28 | 22.3 | 23.8 | Moderate |
| Derivative 2 | 8.97 | 9.79 | 8.28 | 9.08 | Low |
| Derivative 3 | 12.8 | 19.7 | 13.8 | 15.48 | Low |
| Derivative 4 | 11.3 | 15 | 13.9 | 13.4 | Low |
| Derivative 5 | 13.8 | 15.2 | 13.8 | 14.3 | Low |
| Bandrowski Base | 5.4 | 6.0 | 5.5 | 5.6 | Low |
| p-Benzoquinone | 87.0 | 87.5 | 91.6 | 88.7 | High |
| Lactose | 0 | 0 | 0 | 0 | No or Minimal |

The results of the lysine DPRA are shown in Tables 22 and 23. At 20 mins incubation, almost all the derivatives are less reactive towards the Lysine. Interestingly derivative 3 to 5 showed no or minimal activity towards the Lysine at 20 mins. Continuous incubation for 24 h resulted in increase in the reactivity for the PPD and PPD derivative 1. However, for other derivatives 2 to 5, we observed low reactivity towards lysine. Overall, among PPD derivatives 1-5, analogues 3 and 4 represented the best candidate with the moderate reactivity for cysteine peptide and analogues 2-5 emerged as best molecules for lysine peptide with low reactivity. The results signify the importance of having substituents at the ortho-position of PPD and PPD dimeric structure with large chain to minimize the reactivity to peptides and skin sensitization potential.

Further Analysis

Figure 12:
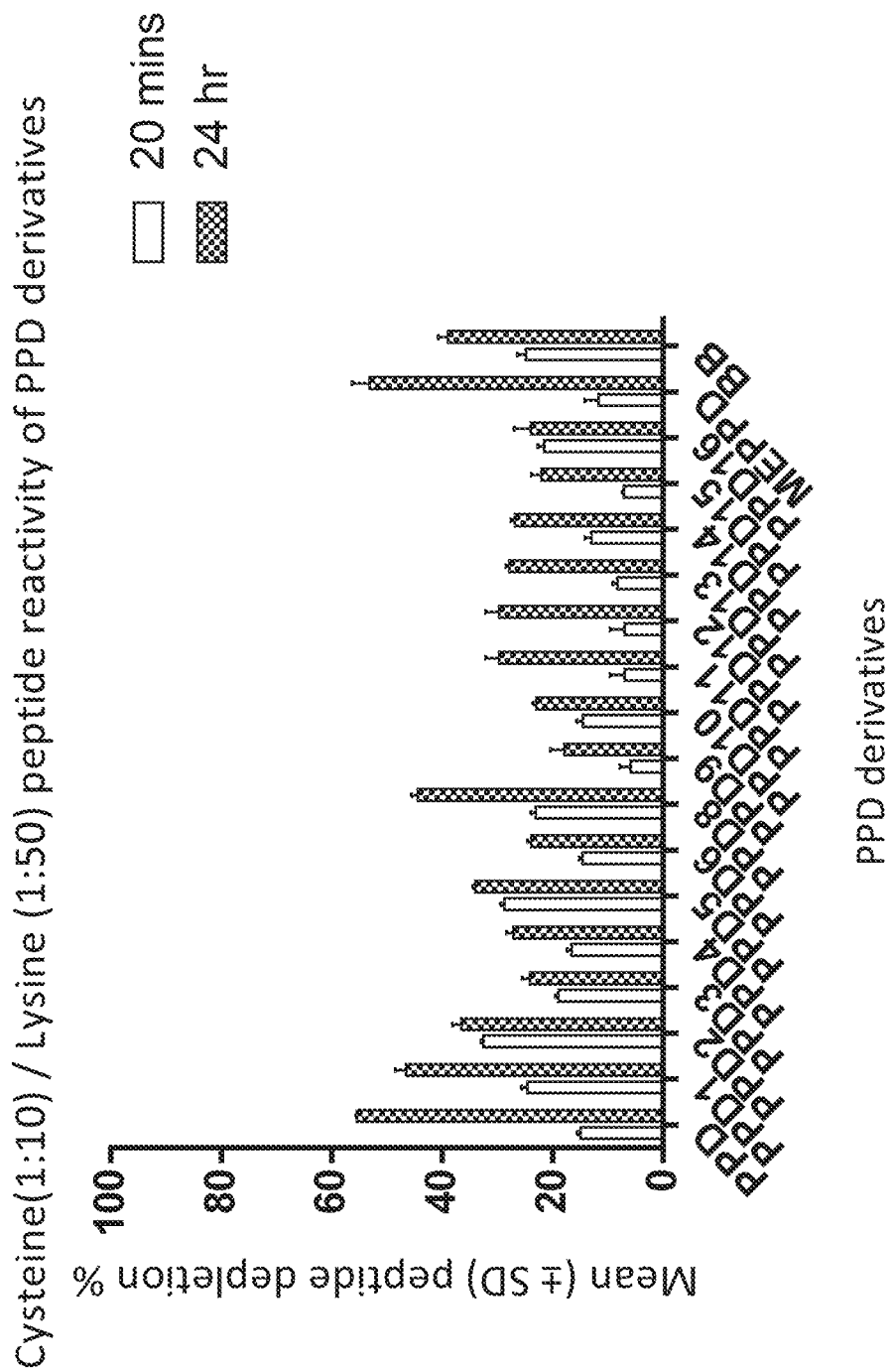

Further peptide depletion results on PPD derivatives using cysteine and lysine peptides are shown in FIG. 12 and discussed below. The results were obtained from procedures as mentioned above and the reaction setup in Table 19.

From DPRA results (FIG. 12), PPD is again proven to be a strong sensitizer. This classification is consistent with existing literature and thus, PPD serves as a relative standard in this DPRA for our test compounds.

Among the synthesized derivatives, PPD 9, 10 showed lowest mean peptide depletion with 17.9% & 23.0% respectively, proven to be a weak sensitizer in the whole PPD derivatives series. In both derivatives (PPD 9 & 10), one end of the amine functionality has been blocked by benzyl substituent, which resulted in the unavailability of the amine for oxidation to form imine conjugate intermediate, and this could have contributed to the less binding with peptides. Next to the PPD 9 & 10, we noticed, PPD 3, 4 & 16 appeared to have performed better in DPRA assays within the range 24.1% to 25.5% and showed 2 times less binding than PPD and emerged as a moderate sensitizer. Both derivatives have strong electron donating substituents at ortho position of PPD which could render the benzene ring electron rich and make it less available for nucleophilic protein interaction. A lower value of mean depletion observed for PPD 16 vs PPD 4 as it had an additional N-hexyl substitution which makes compound more lipophilic, which reduced the binding with hydrophilic peptides and further blocked the amine functionality to avoid the oxidation to imines. Of note, the moderate sensitizing potential of PPD 3, 4 & 16 was predicted from a borderline mean peptide depletion (within the range 24.1% to 25.5%) quite close to weak sensitizers (mean peptide depletion <22.62%). Interestingly, PPD 6, 15, which are ortho ester substituted derivatives, showed lower peptide depletion of 22-24%, despite the moderate electron withdrawing groups, suggesting that the presence moderate withdrawing groups did not influence the electrophilic character of the benzene.

As for the other derivatives (PPD 1, 2, 8) with high mean peptide depletion values, demonstrated properties of high sensitizing agents, possibly due to them being bigger molecules with more sites being reactive to the model heptapeptides. Interestingly, dimeric form of the PPD 1 displayed lower binding potential than trimer PPD 2 and tetramer PPD 8, which could be the result of less log P value of PPD 1 (log P of 0.93) as compared to PPD 2& 8 (1.86 & 3.02). This observation reminds us to be heedful of the balance between attempting to use the increase in molecular size (and molecular weight) as a strategy to lower the extent of skin permeation of PPD derivatives, and the unintended introduction of additional reactive sites for forming imines and subsequent adducts with peptides. As expected, another trimeric form of the PPD, the Bandrowski base, showed similar mean peptide depletion (38.9%) as PPD 2 and is considered a moderate sensitizer as compared to PPD.

With regards to another series of PPD derivatives, i.e. symmetrically alkyl capped oligo anilines PPD 11-14, they emerged as border line moderate-weak sensitizer. As all of these 4 derivatives showed increasing log P trend from 4-OH benzyl substituents (PPD 11) to 4-CH3 benzyl substituents (PPD 14) at the terminal amines of the dimeric form of the PPD, it was not surprising that the mean peptide depletion decreased with increasing the log P from PPD 11-14. This is the result of both unavailability of the amine for oxidation and marked increase in the log P, which make them less available for nucleophilic binding with proteins. Another class of commercially available PPD derivative, ME-PPD (which has being recently launched in hair dye products as safer alternative to PPD) showed higher mean peptide depletion of 53.2%, which is only slightly lower than PPD. This suggested that the addition of weaker electron donating group (CH2OCH3) at the ortho position of the PPD did not improve the log P and the electron density of the benzene ring could not alter the binding efficiency with model peptides, thus resulting as strong sensitizer (similar to PPD) in our experiments.

Nonetheless, all the novel PPD Derivatives tested (PPD 3, 4, 6 &15, 9 &10, 11-14,) showed mean peptide depletion percentages ranges from 17.9%-33.4% in comparison with PPD (55.5%), thus corroborating the hypothesis that their structural diversity with enhanced log P and molecular weight, as well as the protection of the terminal amine by benzyl substituents might indeed be responsible for their less sensitizing potential in cosmetic products. The results also signify the importance of having strong electron donating substituents at ortho position of PPD and PPD dimeric structure with large chain to minimize the reactivity to peptides and skin sensitization potential. As noted by the developers and other researchers, this classification system is a preliminary screening tool to estimate the sensitizing potential of test compounds based on peptide depletion 19 and skin sensitization depends on skin penetration of the test compounds as well. Therefore, we have conducted skin permeation studies to shed light on how PPD derivatives 1-6 &15 and ME-PPD behave when applied to skin.

Example 19: Preliminary Enzyme-Linked Immunosorbent Assay (ELISA) Studies

Methods:
Cytokine and Surface Marker Assays
For cytokine profiling in THP-1, supernatants from wells were collected and then used for cytokine analysis by a Chemokine immunosorbent assay Bio-legend ELISA Max kit. The levels of available IL-8 protein from THP-1 cell supernatants was estimated using this kit which are regulated upon activation of THP-1 model. Surface receptor expression of human CD-86, CD-54, MHC-I and IL-T3 were analyzed by flow cytometry using standard BD FACS analyzer with PE and FITC fluorescent labeled antibodies from Biolegend and e Bioscience.

Results and Discussion:
In order to understand the effect of modified PPD hairdyes on THP-1 immune sensitization, a certain degree of Cytotoxicity at CV75% viable where 25% cell death is required before evaluation of supernatants in THP-1 models for expression of cytokine IL-8 and receptor expression of CD86, CD54, MHC-I and IL-T3 surface receptors upon treatment with standard PPD and modified hair dye compounds. Most allergens show a specific dose-dependent alteration of CD86 and/or CD54 expression or secretion of cytokine profiles. But depending on chemical, the alteration pattern may vary.

Figure 13:
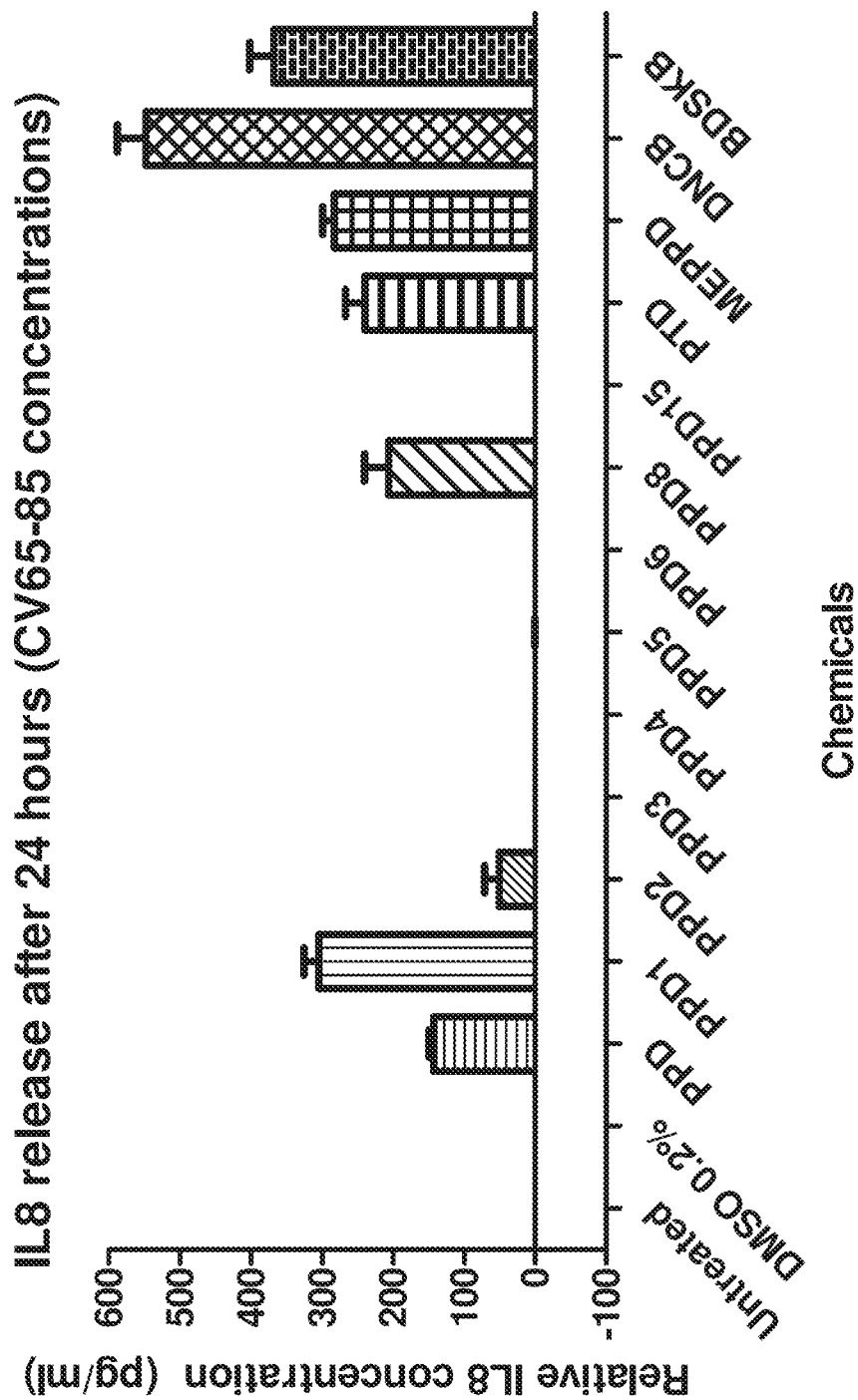
FIG. 13 depicts relative IL8 release elicited by PPD derivatives and commercial dyes in a preliminary ELISA study.
Figure 14:
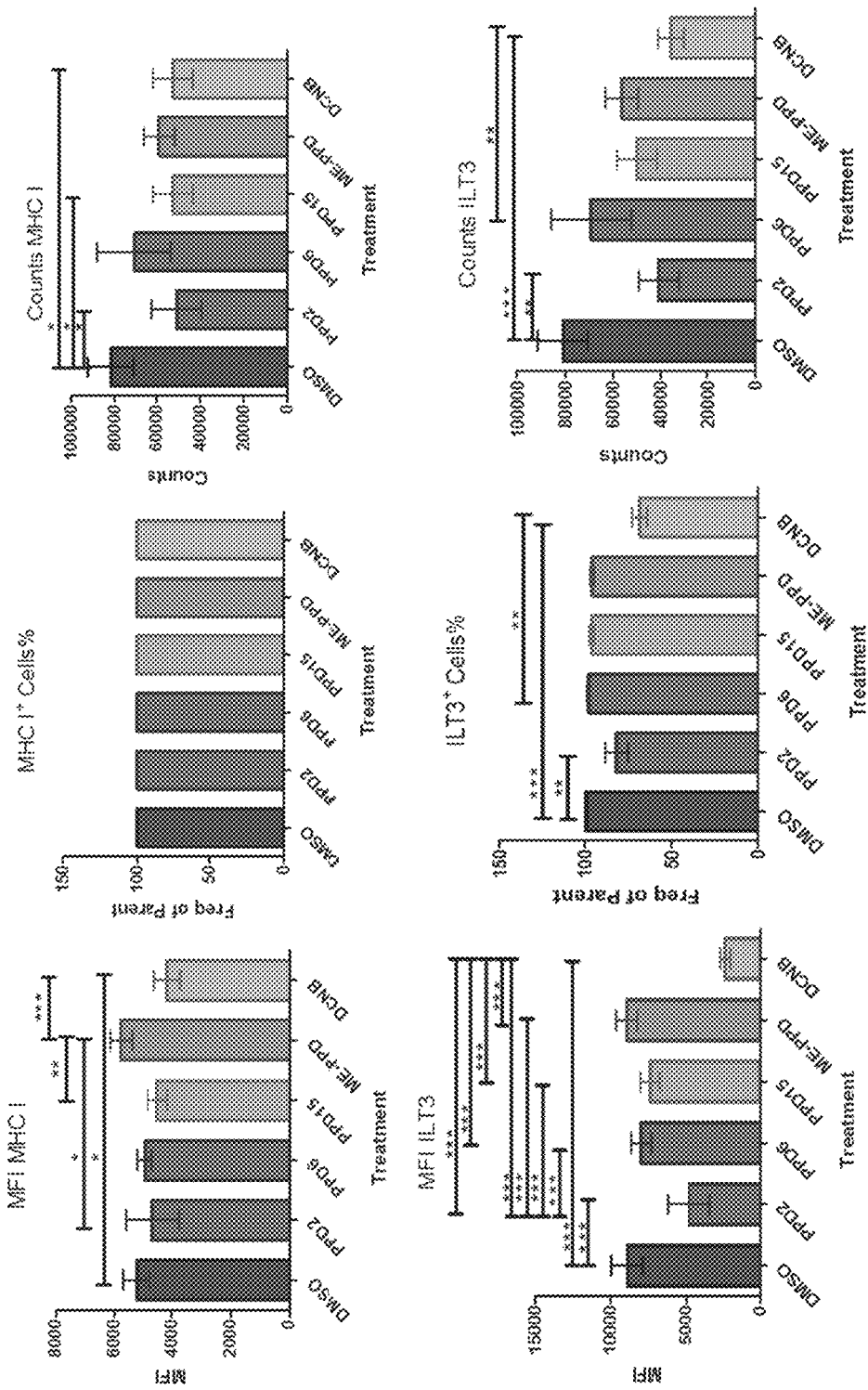
FIGS. 14 & 15 depict the results of the cytokine markers (MHC-1, ILT3, CD86 and CD54) analysis.
Figure 15:
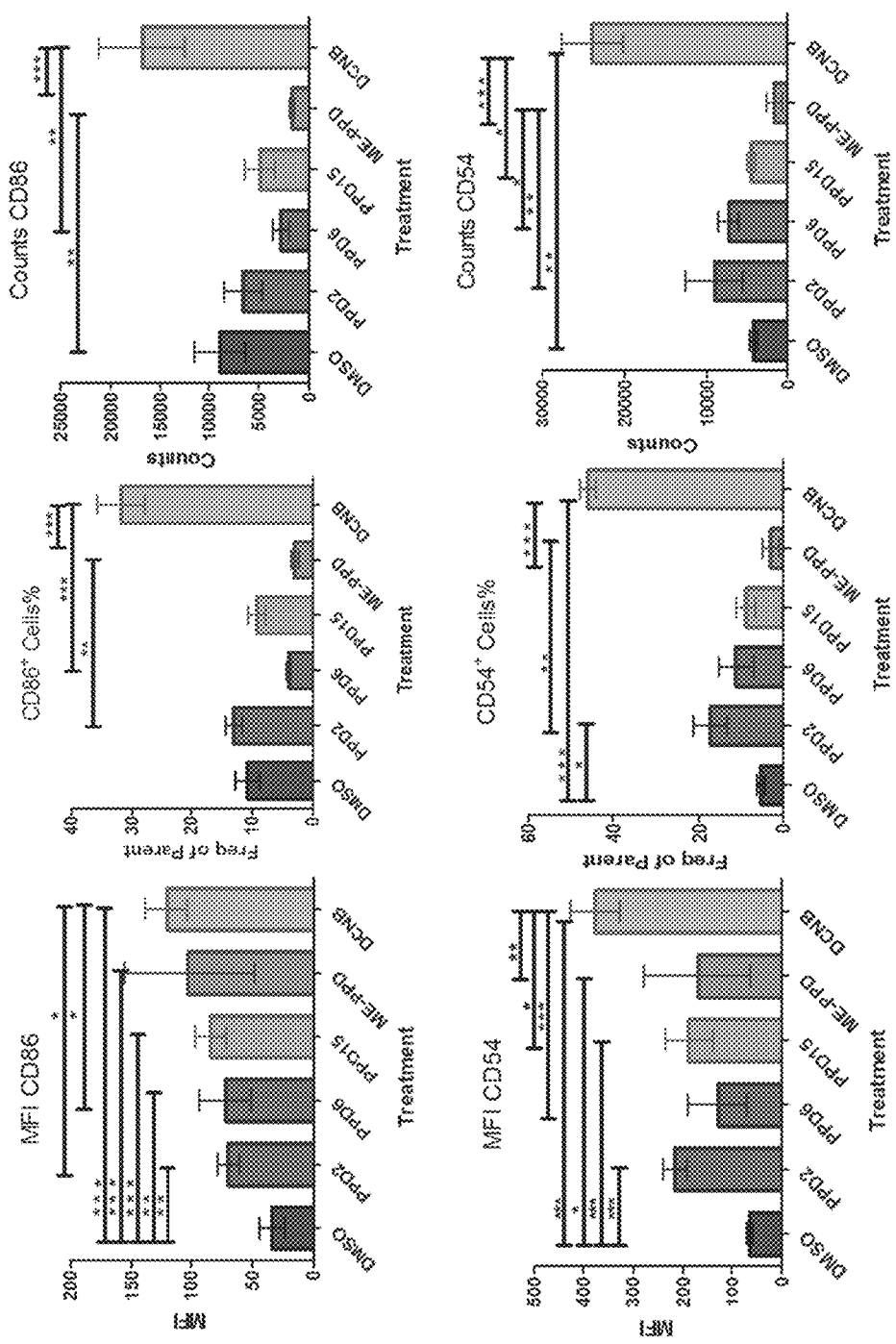

As shown in FIGS. 13-15, increased expression of IL-8 with standard hair dyes PPD, PTD, ME-PPD, DNCB control, BBB and new hair dye compounds PPD-1, 8 is observed while other modified hair dyes PPD 6, 15 do not stimulate IL-8 expression suggestive of lack of sensitization. Moreover, increased expression of CD86 (co-stimulatory activation marker) and CD54 (intercellular adhesion molecule), suggestive of THP-1 immune cell maturation and alarm response. Expression of CD86 and CD 54 is not stimulated by PPD-15 and PPD-6 suggesting lack of sensitization by these hair dye compounds. In comparison to DCNB, PPD2, 6, PPD15 and ME-PPD increased ILT3 (inhibitory receptor) expression, which suggest that these compounds stimulate specific signaling pathways opposing sensitization for immune inflammatory response These preliminary analyses indicate activation and deactivation of these receptors or secretion of cytokines suggesting hair dye effect on THP-1 models. In skin the activated mature dendritic cells will subsequently migrate to lymphoid tissue carrying antigen acquired in the skin and induce an adaptive immune response that will provide subsequent protection due to sensitization and inflammatory response.

The invention claimed is:

1. A compound of formula I:

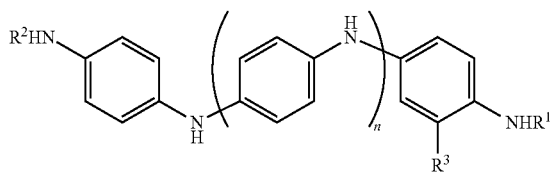

I wherein:

$R^1$ and $R^2$ independently represent H, $CH_2$Phenyl or $C_{5-10}$ alkyl, which phenyl group is substituted by $NO_2$, $OCH_3$, $CH_3$ or OH, and which $C_{5-15}$ alkyl group is unsubstituted or substituted with one or more substituents selected from:

$C_{1-10}$ alkyl, which group is unsubstituted or substituted by one or more substituents selected from OH, nitro, CN, $OR^{4a}$, $NR^{4b}R^{4c}$, aryl and $Het^1$;

$Cy^1$, which $Cy^1$ group is unsubstituted or substituted by one or more substituents selected from nitro, CN, $C_{1-10}$ alkyl (which $C_{1-10}$ alkyl group is unsubstituted or substituted by one or more substituents selected from OH, =O, $C_{1-4}$ alkyl and $C_{1-4}$ alkoxy), and $OR^{5a}$, $S(O)_qR^{5b}$, $S(O)_2NR^{5c}R^{5d}$, $NR^{5e}S(O)_2R^{5f}$, $NR^{5g}R^{5h}$;

$Het^a$, which $Het^a$ group is unsubstituted or substituted by one or more substituents selected from nitro, CN, $C_{1-6}$ alkyl (which $C_{1-6}$ alkyl group is unsubstituted or substituted by one or more substituents selected from OH, =O, halo, $C_{1-4}$ alkyl and $C_{1-4}$ alkoxy), $OR^{6a}$, $S(O)_qR^{6b}$, $S(O)_2NR^{6c}R^{6d}$, $NR^{6e}S(O)_2R^{6f}$, $NR^{6g}R^{6h}$; and $OR^{7a}$, $S(O)_qR^{7b}$, $S(O)_2NR^{7c}R^{7d}$, $NR^{7e}S(O)_2R^{7f}$ and $NR^{7g}R^{7h}$, $R^3$ represents H, $OC_{1-10}$ alkyl, $C(O)OC_{1-10}$ alkyl or $OC(O)C_{1-10}$ alkyl, which $OC_{1-10}$ alkyl, $C(O)OC_{1-10}$ alkyl and $OC(O)C_{1-10}$ alkyl groups are unsubstituted or substituted with one or more substituents selected from:

$C_{1-10}$ alkyl, which group is unsubstituted or substituted by one or more substituents selected from OH, nitro, CN, $OR^{8a}$, $NR^{8b}R^{8c}$, aryl and $Het^2$;

$Cy^2$, which $Cy^2$ group is unsubstituted or substituted by one or more substituents selected from nitro, CN, $C_{1-6}$ alkyl (which $C_{1-6}$ alkyl group is unsubstituted or substituted by one or more substituents selected from OH, =O, $C_{1-4}$ alkyl and $C_{1-4}$ alkoxy), and $OR^{9a}$, $S(O)_qR^{9b}$, $S(O)_2NR^{9c}R^{9d}$, $NR^{9e}S(O)_2R^{9f}$, $NR^{9g}R^{9h}$;

$Het^b$, which $Het^b$ group is unsubstituted or substituted by one or more substituents selected from nitro, CN, $C_{1-6}$ alkyl (which $C_{1-6}$ alkyl group is unsubstituted or substituted by one or more substituents selected from OH, =O, halo, $C_{1-4}$ alkyl and $C_{1-4}$ alkoxy), $OR^{10a}$, $S(O)_qR^{10b}$, $S(O)_2NR^{10c}R^{10d}$, $NR^{10e}S(O)_2R^{10f}$, $NR^{10g}R^{10h}$; and $OR^{11a}$, $S(O)_qR^{11b}$, $S(O)_2NR^{11c}R^{11d}$, $NR^{11e}S(O)_2R^{11f}$ and $NR^{11g}R^{11h}$, $Het^1$ and $Het^2$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{12a}$ and $C_{1-10}$ alkyl, which $C_{1-10}$ alkyl group is unsubstituted;

Cy$^1$ and Cy$^2$ represent, independently at each occurrence, a 3- to 6-membered aromatic, fully saturated or partially unsaturated carbocyclic ring;

R$^{4a}$ to R$^{4c}$, R$^{5a}$ to R$^{5h}$, R$^{6a}$ to R$^{6h}$, R$^{7a}$ to R$^{7h}$, R$^{8a}$ to R$^{8c}$, R$^{9a}$ to R$^{9h}$, R$^{10a}$ to R$^{10h}$, R$^{11a}$ to R$^{11h}$, independently represent, at each occurrence, H, or C$_{1-10}$ alkyl (which C$_{1-10}$ alkyl group is unsubstituted or substituted by one or more substituents selected from C$_{1-6}$ alkyl, OR$^{12b}$), or R$^{5-7c}$ and R$^{5-7d}$, R$^{9-11c}$ and R$^{9-11d}$, R$^{5-7g}$ and R$^{5-7h}$, R$^{9-11g}$ and R$^{9-11h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and C$_{1-6}$ alkyl;

Het$^a$ and Het$^b$ independently represent 4- to 14-membered heterocyclic groups containing one or more heteroatoms selected from O, S and N;

R$^{12a-b}$ independently represents, at each occurrence, H or C$_{1-4}$ alkyl, and n represents 0 to 4, or a physiologically acceptable salt or solvate, or an oxidised derivative thereof of the compound of formula I, provided that when R$^1$ and R$^2$ are H, and n is 0, 1 or 2, R$^3$ is not H.

2. A method of dyeing hair or of applying a temporary tattoo, which method comprises applying a composition comprising a compound of formula I or a physiologically acceptable salt or solvate, or an oxidised derivative thereof, to the hair or skin of a subject, wherein the compound of formula I has the structure:

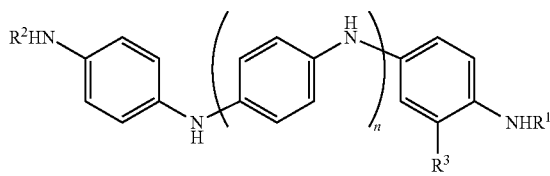

I wherein:

R$^1$ and R$^2$ independently represent H, CH$_2$Phenyl or C$_{5-10}$ alkyl, which phenyl group is substituted by NO$_2$, OCH$_3$, CH$_3$ or OH, and which C$_{5-10}$ alkyl group is unsubstituted or substituted with one or more substituents selected from:

C$_{1-10}$ alkyl, which group is unsubstituted or substituted by one or more substituents selected from OH, nitro, CN, OR$^{4a}$, NR$^{4b}$R$^{4c}$, aryl and Het$^1$;

Cy$^1$, which Cy$^1$ group is unsubstituted or substituted by one or more substituents selected from nitro, CN, C$_{1-6}$ alkyl (which C$_{1-6}$ alkyl group is unsubstituted or substituted by one or more substituents selected from OH, =O, C$_{1-4}$ alkyl and C$_{1-4}$ alkoxy), and OR$^{5a}$, S(O)$_q$R$^{5b}$, S(O)$_2$NR$^{5c}$R$^{5d}$, NR$^{5e}$S(O)$_2$R$^{5f}$, NR$^{5g}$R$^{5h}$;

Het$^a$, which Het$^a$ group is unsubstituted or substituted by one or more substituents selected from nitro, CN, C$_{1-6}$ alkyl (which C$_{1-6}$ alkyl group is unsubstituted or substituted by one or more substituents selected from OH, =O, halo, C$_{1-4}$ alkyl and C$_{1-4}$ alkoxy), OR$^{6a}$, S(O)$_q$R$^{6b}$, S(O)$_2$NR$^{6c}$R$^{6d}$, NR$^{6e}$S(O)$_2$R$^{6f}$, NR$^{6g}$R$^{6h}$; and OR$^{7a}$, S(O)$_q$R$^{7b}$, S(O)$_2$NR$^{7c}$R$^{7d}$, NR$^{7e}$S(O)$_2$R$^{7f}$ and NR$^{7g}$R$^{7h}$, R$^3$ represents H, C$_{1-10}$ alkyl, OC$_{1-10}$ alkyl, C(O)OC$_{1-10}$ alkyl or OC(O)C$_{1-10}$ alkyl, which C$_{1-10}$ alkyl, OC$_{1-10}$ alkyl, C(O)OC$_{1-10}$ alkyl or OC(O)C$_{1-10}$ alkyl groups are unsubstituted or substituted with one or more substituents selected from:

C$_{1-10}$ alkyl, which group is unsubstituted or substituted by one or more substituents selected from OH, nitro, CN, OR$^{8a}$, NR$^{8b}$R$^{8c}$, aryl and Het$^2$;

Cy$^2$, which Cy$^2$ group is unsubstituted or substituted by one or more substituents selected from nitro, CN, C$_{1-6}$ alkyl (which C$_{1-6}$alkyl group is unsubstituted or substituted by one or more substituents selected from OH, =O, C$_{1-4}$ alkyl and C$_{1-4}$ alkoxy), and OR$^{9a}$, S(O)$_q$R$^{9b}$, S(O)$_2$NR$^{9c}$R$^{9d}$, NR$^{9e}$S(O)$_2$R$^{9f}$, NR$^{9g}$R$^{9h}$;

Het$^b$, which Het$^b$ group is unsubstituted or substituted by one or more substituents selected from nitro, CN, C$_{1-6}$ alkyl (which C$_{1-6}$ alkyl group is unsubstituted or substituted by one or more substituents selected from OH, =O, halo, C$_{1-4}$ alkyl and C$_{1-4}$ alkoxy), OR$^{10a}$, S(O)$_q$R$^{10b}$, S(O)$_2$NR$^{10c}$R$^{10d}$, NR$^{10e}$S(O)$_2$R$^{10f}$, NR$^{10g}$R$^{10h}$; and OR$^{11a}$, S(O)$_q$R$^{11b}$, S(O)$_2$NR$^{11c}$R$^{11d}$, NR$^{11e}$S(O)$_2$R$^{11f}$ and NR$^{11g}$R$^{11h}$, Het$^1$ and Het$^2$ represent, independently at each occurrence, a 4- to 14-membered heterocyclic group containing one or more heteroatoms selected from O, S and N, which heterocyclic groups may comprise one, two or three rings and may be substituted by one or more substituents selected from OR$^{12a}$ and C$_{1-10}$ alkyl, which C$_{1-10}$ alkyl group is unsubstituted;

Cy$^1$ and Cy$^2$ represent, independently at each occurrence, a 3- to 6-membered aromatic, fully saturated or partially unsaturated carbocyclic ring;

R$^{4a}$ to R$^{4c}$, R$^{5a}$ to R$^{5h}$, R$^{6a}$ to R$^{6h}$, R$^{7a}$ to R$^{7h}$, R$^{8a}$ to R$^{8c}$, R$^{9a}$ to R$^{9h}$, R$^{10a}$ to R$^{10h}$, R$^{11a}$ to R$^{11h}$, independently represent, at each occurrence, H, or C$_{1-10}$ alkyl (which C$_{1-10}$ alkyl group is unsubstituted or substituted by one or more substituents selected from C$_{1-6}$ alkyl, OR$^{12b}$), or R$^{5-7c}$ and R$^{5-7d}$, R$^{9-11c}$ and R$^{9-11d}$, R$^{5-7g}$ and R$^{5-7h}$, R$^{9-11g}$ and R$^{9-11h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and C$_{1-10}$ alkyl;

Het$^a$ and Het$^b$ independently represent 4- to 14-membered heterocyclic groups containing one or more heteroatoms selected from O, S and N;

R$^{12a-b}$ independently represents, at each occurrence, H or C$_{1-4}$ alkyl, n represents 0 to 4, or a physiologically acceptable salt or solvate, or an oxidised derivative thereof of the compound of formula I, provided that when R$^1$ and R$^2$ are H, and n is 0, R$^3$ is not H.

3. The compound according to claim 1, wherein in the compound of formula I, R$^1$ and R$^2$ independently represent H or C$_{6-8}$ alkyl, which C$_{6-8}$ alkyl group is unsubstituted or substituted with one or more substituents selected from C$_{1-3}$ alkyl, Cy$^1$ (which Cy$^1$ group is unsubstituted or substituted by one or more substituents selected from nitro, C$_{1-3}$ alkyl, and OR$^{5a}$), Het$^a$ (which Het$^a$ group is unsubstituted or substituted by one or more substituents selected from nitro, $C_{1-3}$ alkyl, and $OR^{6a}$), and $OR^{7a}$.

4. The compound according to claim 1, wherein in the compound of formula I, $R^3$ represents $O-C_{1-6}$ alkyl, or $C(O)OC_{1-6}$ alkyl, which $O-C_{1-6}$ alkyl and $C(O)OC_{1-6}$ alkyl groups are unsubstituted or substituted with one or more substituents selected from $C_{1-3}$ alkyl.

5. The compound according to claim 1, wherein in the compound of formula I, $Cy^1$ when present represents independently a phenyl ring.

6. The compound according to claim 1, wherein n represents 1 to 3.

7. The compound according to claim 1, wherein the compound of formula I is selected from the list:
(i) 4-Amino-(3-hexyloxy)-4'-aminodiphenylamine;
(ii) hexyl [2-amino-5-(4-aminophenylamino)]benzoate;
(iii) 4-hexylamino-(3-hexyloxy)-4'-aminodiphenylamine;
(iv) 4-Amino-4'-[(4-tolylaminomethyl)phenyl]diphenylamine;
(v) $N^1$-[4-(4-tolylaminomethyl)phenyl]-$N^4$-(4-aminophenyl)-1,4-benzenediamine;
(vi) $N^4$-[(4-nitrophenyl)methyl]-$N^1$-[4-[(4-nitrophenyl)methylamino]phenyl]-benzene-1,4-diamine;
(vii) $N^4$-[(4-methoxyphenyl)methyl]-$N^1$-[4-[(4-ethoxyphenyl)methylamino]-phenyl]benzene-1,4-diamine;
(viii) $N^4$-(p-tolylmethyl)-$N^1$-[4-(p-tolylmethylamino)phenyl]benzene-1,4-diamine; and
(ix) 4-[[4-[4-[(4-hydroxyphenyl)methylamino]anilino]anilino]methyl]phenol.

8. The compound according to claim 7, wherein the compound of formula I is hexyl [2-amino-5-(4-aminophenylamino)]benzoate.

9. The method according to claim 2, wherein the compound of formula I is selected from the list of:
(a) $N^1,N^4$-bis(4-aminophenyl)-1,4-benzenediamine;
(b) 4-Amino-(3-hexyloxy)-4'-aminodiphenylamine;
(c) hexyl [2-amino-5-(4-aminophenylamino)]benzoate;
(d) 4-hexylamino-(3-hexyloxy)-4'-aminodiphenylamine;
(e) 4,4'-Bis[(4-aminophenyl)amino]diphenylamine;
(f) 4-Amino-4'-[(4-tolylaminomethyl)phenyl]diphenylamine;
(g) $N^1$-[4-(4-tolylaminomethyl)phenyl]-$N^4$-(4-aminophenyl)-1,4-benzenediamine;
(h) $N^4$-[(4-nitrophenyl)methyl]-$N^1$-[4-[(4-nitrophenyl)methylamino]phenyl]-benzene-1,4-diamine;
(i) $N^4$-[(4-methoxyphenyl)methyl]-$N^1$-[4-[(4-ethoxyphenyl)methylamino]-phenyl]benzene-1,4-diamine;
(j) $N^4$-(p-tolylmethyl)-$N^1$-[4-(p-tolylmethylamino)phenyl]benzene-1,4-diamine; and
(k) 4-[[4-[4-[(4-hydroxyphenyl)methylamino]anilino]anilino]methyl]phenol.

10. The method according to claim 9, wherein the compound of formula I is hexyl [2-amino-5-(4-aminophenylamino)]benzoate.

11. A compound of formula II:

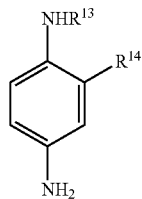

II wherein:
$R^{13}$ represents H or $C_{6-10}$ alkyl, which $C_{6-10}$ alkyl group is unsubstituted or substituted with one or more substituents selected from:
$C_{1-10}$ alkyl, which group is unsubstituted or substituted by one or more substituents selected from OH, nitro, CN, $OR^{15a}$, $NR^{15b}R^{15c}$, aryl and $Het^3$;
$Cy^3$, which $Cy^3$ group is unsubstituted or substituted by one or more substituents selected from nitro, CN, $C_{1-6}$ alkyl (which $C_{1-6}$ alkyl group is unsubstituted or substituted by one or more substituents selected from OH, =O, $C_{1-4}$ alkyl and $C_{1-4}$ alkoxy), and $OR^{16a}$, $S(O)_qR^{16b}$, $S(O)_2NR^{16c}R^{16d}$, $NR^{16e}S(O)_2R^{16f}$, $NR^{16g}R^{16h}$;
$Het^c$, which $Het^c$ group is unsubstituted or substituted by one or more substituents selected from nitro, CN, $C_{1-6}$ alkyl (which $C_{1-6}$ alkyl group is unsubstituted or substituted by one or more substituents selected from OH, =O, halo, $C_{1-4}$ alkyl and $C_{1-4}$ alkoxy), $OR^{17a}$, $S(O)_qR^{17b}$, $S(O)_2NR^{17c}R^{17d}$, $NR^{17e}S(O)_2R^{17f}$, $NR^{17g}R^{17h}$; and
$OR^{18a}$, $S(O)_qR^{18b}$, $S(O)_2NR^{18c}R^{18d}$, $NR^{18e}S(O)_2R^{18f}$ and $NR^{18g}R^{18h}$,
$R^{14}$ represents $C_{1-10}$ alkyl, $OC_{1-10}$ alkyl, $C(O)OC_{1-10}$ alkyl or $OC(O)C_{1-10}$ alkyl, which $OC_{1-10}$ alkyl is substituted with one or more substituents selected from:
$Cy^4$, which $Cy^4$ group is unsubstituted or substituted by one or more substituents selected from nitro, CN, $C_{1-6}$ alkyl (which $C_{1-6}$ alkyl group is unsubstituted or substituted by one or more substituents selected from OH, =O, $C_{1-4}$ alkyl and $C_{1-4}$ alkoxy), and $OR^{20a}$, $S(O)_qR^{20b}$, $S(O)_2NR^{20c}R^{20d}$, $NR^{20e}S(O)_2R^{20f}$, $NR^{20g}R^{20h}$;
$Het^d$, which $Het^d$ group is unsubstituted or substituted by one or more substituents selected from nitro, CN, $C_{1-10}$ alkyl (which $C_{1-10}$ alkyl group is unsubstituted or substituted by one or more substitutents selected from OH, =O, halo, $C_{1-4}$ alkyl and $C_{1-4}$ alkoxy), $OR^{21a}$, $S(O)_qR^{21b}$, $S(O)_2NR^{21c}$, $R_{21d}$, $NR^{21e}S(O)_2R^{21f}$, $NR^{21g}R^{21h}$; and
$OR^{22a}$, $S(O)_qR^{22b}$, $S(O)_2NR^{22c}R^{22d}$, $NR^{22e}S(O)_2R^{22f}$ and $NR^{22g}R^{22h}$; and p1 and which $C_{1-10}$ alkyl, $C(O)OC_{1-10}$ alkyl and $OC(O)C_{1-10}$ alkyl groups are unsubstituted or substituted with one or more substituents selected from:
$C_{1-10}$ alkyl, which group is unsubstituted or substituted by one or more substituents selected from OH, nitro, CN, $OR^{19a}$, $NR^{19b}R^{19c}$, aryl and $Het^4$;
$Cy^4$, which $Cy^4$ group is unsubstituted or substituted by one or more substituents selected from nitro, CN, $C_{1-6}$ alkyl (which $C_{1-6}$ alkyl group is unsubstituted or substituted by one or more substituents selected from OH, =O, $C_{1-4}$ alkyl and $C_{1-4}$ alkoxy), and $OR^{20a}$, $S(O)_qR^{20b}$, $S(O)_2NR^{20c}R^{20d}$, $NR^{20e}S(O)_2R^{20f}$, $NR^{20g}R^{20h}$;
$Het^d$, which $Het^d$ group is unsubstituted or substituted by one or more substituents selected from nitro, CN, $C_{1-10}$ alkyl (which $C_{1-6}$ alkyl group is unsubstituted or substituted by one or more substituents selected from OH, =O, halo, $C_{1-4}$ alkyl and $C_{1-4}$ alkoxy), $OR^{21a}$, $S(O)_qR^{21b}$, $S(O)_2NR^{21c}R^{21d}$, $NR^{21e}S(O)_2R^{21f}$, $NR^{21g}R^{21h}$; and
$OR^{22a}$, $S(O)_qR^{22b}$, $S(O)_2NR^{22c}R^{22d}$, $NR^{22e}S(O)_2R^{22f}$ and $NR^{22g}R^{22h}$,
$Het^3$ and $Het^4$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{23a}$ and $C_{1-10}$ alkyl, which $C_{1-10}$ alkyl group is unsubstituted;

$Cy^3$ and $Cy^4$ represent, independently at each occurrence, a 3- to 6-membered fully saturated or partially unsaturated carbocyclic ring;

$R^{15a}$ to $R^{15c}$, $R^{16a}$ to $R^{16h}$, $R^{17a}$ to $R^{17h}$, $R^{18a}$ to $R^{18h}$, $R^{19a}$ to $R^{19c}$, $R^{20a}$ to $R^{20h}$, $R^{21a}$ to $R^{21h}$, $R^{22a}$ to $R^{22h}$, independently represent, at each occurrence, H, or $C_{1-10}$ alkyl (which $C_{1-10}$ alkyl group is unsubstituted or substituted by one or more substituents selected from $C_{1-6}$ alkyl, $OR^{23b}$), or $R^{16-18c}$ and $R^{16-18d}$, $R^{20-22c}$ and $R^{20-22d}$, $R^{16-18g}$ and $R^{16-18h}$, $R^{20-22g}$ and $R^{20-22h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and $C_{1-6}$ alkyl;

$Het^c$ and $Het^d$ independently represent 4- to 14-membered heterocyclic groups containing one or more heteroatoms selected from O, S and N;

$R^{23a-b}$ independently represents, at each occurrence, H or $C_{1-4}$ alkyl, or an oxidised derivative thereof of the compound of formula II, provided that when $R^{13}$ is H, $R^{14}$ is not n-hexyl.

12. A method of dyeing hair or of applying a temporary tattoo, which method comprises applying a composition comprising a compound of formula II or a physiologically acceptable salt or solvate, or an oxidised derivative thereof, to the hair or skin of a subject, wherein the compound of formula II has the structure:

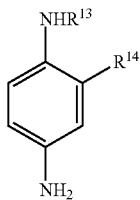

II wherein:

$R^{13}$ represents H or $C_{6-10}$ alkyl, which $C_{6-10}$ alkyl group is unsubstituted or substituted with one or more substituents selected from:
$C_{1-10}$ alkyl, which group is unsubstituted or substituted by one or more substituents selected from OH, nitro, CN, $OR^{15a}$, $NR^{15b}R^{15c}$, aryl and $Het^3$;
$Cy^3$, which $Cy^3$ group is unsubstituted or substituted by one or more substituents selected from nitro, CN, $C_{1-6}$ alkyl (which $C_{1-6}$ alkyl group is unsubstituted or substituted by one or more substituents selected from OH, =O, $C_{1-4}$ alkyl and $C_{1-4}$ alkoxy), and $OR^{16a}$, $S(O)_qR^{16b}$, $S(O)_2NR^{16c}R^{16d}$, $NR^{16e}S(O)_2R^{16f}$, $NR^{16g}R^{16h}$;
$Het^c$, which $Het^c$ group is unsubstituted or substituted by one or more substituents selected from nitro, CN, $C_{1-6}$ alkyl (which $C_{1-6}$ alkyl group is unsubstituted or substituted by one or more substituents selected from OH, =O, halo, $C_{1-4}$ alkyl and $C_{1-4}$ alkoxy), $OR^{17a}$, $S(O)_qR^{17b}$, $S(O)_2NR^{17c}R^{17d}$, $NR^{17e}S(O)_2R^{17f}$, $NR^{17g}R^{17h}$; and
$OR^{18a}$, $S(O)_qR^{18b}$, $S(O)_2NR^{18c}R^{18d}$, $NR^{18e}S(O)_2R^{18f}$ and $NR^{18g}R^{18h}$, $R^{14}$ represents $C_{1-10}$ alkyl, $OC_{1-10}$ alkyl, $C(O)OC_{1-10}$ alkyl or $OC(O)C_{1-10}$ alkyl, which $C_{1-10}$ alkyl, $OC_{1-10}$ alkyl, $C(O)OC_{1-10}$ alkyl and $OC(O)C_{1-10}$ alkyl groups are unsubstituted or substituted with one or more substituents selected from:
$C_{1-10}$ alkyl (which group is unsubstituted or substituted by one or more substituents selected from OH, nitro, CN, $OR^{19a}$, $NR^{19b}R^{19c}$, aryl and $Het^4$);
$Cy^4$ (which $Cy^4$ group is unsubstituted or substituted by one or more substituents selected from nitro, CN, $C_{1-6}$ alkyl (which $C_{1-6}$ alkylgroup is unsubstituted or substituted by one or more substituents selected from OH, =O, $C_{1-4}$ alkyl and $C_{1-4}$ alkoxy), and $OR^{20a}$, $S(O)_qR^{20b}$, $S(O)_2NR^{20c}R^{20d}$, $NR^{20e}S(O)_2R^{20f}$, $NR^{20g}R^{20h}$);
$Het^d$ (which $Het^d$ group is unsubstituted or substituted by one or more substituents selected from nitro, CN, $C_{1-10}$ alkyl (which $C_{1-10}$ alkyl group is unsubstituted or substituted by one or more substituents selected from OH, =O, halo, $C_{1-4}$ alkyl and $C_{1-4}$ alkoxy), $OR^{21a}$, $S(O)_qR^{21b}$, $S(O)_2NR^{21c}R^{21d}$, $NR^{21e}S(O)_2R^{21f}$, $NR^{21g}R^{21h}$); and
$OR^{22a}$, $S(O)_qR^{22b}$, $S(O)_2NR^{22c}R^{22d}$, $NR^{22e}S(O)_2R^{22f}$ and $NR^{22g}R^{22h}$, $Het^3$ and $Het^4$ represent, independently at each occurrence, a 4- to 14-membered heterocyclic group containing one or more heteroatoms selected from O, S and N, which heterocyclic groups may comprise one, two or three rings and may be substituted by one or more substituents selected from $OR^{23a}$ and $C_{1-10}$ alkyl, which $C_{1-10}$ alkyl group is unsubstituted;

$Cy^3$ and $Cy^4$ represent, independently at each occurrence, a 3- to 6-membered fully saturated or partially unsaturated carbocyclic ring;

$R^{15a}$ to $R^{15c}$, $R^{16a}$ to $R^{16h}$, $R^{17a}$ to $R^{17h}$, $R^{18a}$ to $R^{18h}$, $R^{19a}$ to $R^{19c}$, $R^{20a}$ to $R^{20h}$, $R^{21a}$ to $R^{21h}$, $R^{22a}$ to $R^{22h}$, independently represent, at each occurrence, H, or $C_{1-10}$ alkyl (which $C_{1-10}$ alkyl group is unsubstituted or substituted by one or more substituents selected from $C_{1-6}$ alkyl, $OR^{23b}$), or $R^{16-18c}$ and $R^{16-18d}$, $R^{20-22c}$ and $R^{20-22d}$, $R^{16-18g}$ and $R^{16-18h}$, $R^{20-22g}$ and $R^{20-22h}$ represent, together with the nitrogen atom to which they are attached, a 3- to 14-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, and $C_{1-6}$ alkyl;

$Het^c$ and $Het^d$ independently represent 4- to 14-membered heterocyclic groups containing one or more heteroatoms selected from O, S and N;

$R^{23a-b}$ independently represents, at each occurrence, H or $C_{1-4}$ alkyl, or an oxidised derivative thereof of the compound of formula II.

13. A compound selected from the list:
(i) 4-2-((2-ethylhexyl)oxy)benzene-1,4-diamine;
(ii) hexyl-2,5-diaminobenzoate; and
(iii) ($N^1$-hexyl)(2-hexyloxy)-1,4-diaminobenzene.

14. The compound according to claim 13, wherein the compound is selected from the list:
   (i) 4-2-((2-ethylhexyl)oxy)benzene-1,4-diamine; and
   (iii) hexyl-2,5-diaminobenzoate.

15. The method according to claim 12, wherein the compound of formula II is selected from the list:
   (i) 4-2-((2-ethylhexyl)oxy)benzene-1,4-diamine;
   (ii) 2-hexyloxy-1,4-diaminobenzene;
   (iii) hexyl-2,5-diaminobenzoate; and
   (iv) ($N^1$-hexyl)(2-hexyloxy)-1,4-diaminobenzene.

16. The method according to claim 15, wherein the compound of formula II is selected from the list:
   (i) 4-2-((2-ethylhexyl)oxy)benzene-1,4-diamine; and
   (ii) ($N^1$-hexyl)(2-hexyloxy)-1,4-diaminobenzene.

17. The method according to claim 15, wherein the compound of formula II is hexyl-2,5-diaminobenzoate.

18. A composition for dyeing hair or tattooing skin, comprising:
   a compound of formula I as defined in claim 1; and
   water.

19. A kit of parts comprising:
   (i) a composition according to claim 18; and
   (ii) a developing composition comprising an oxidising agent.

20. A composition for dyeing hair or tattooing skin, comprising:
   a compound of formula II as defined in Claim 12; and
   water.

21. A kit of parts comprising:
   (i) a composition according to Claim 20; and
   (ii) a developing composition comprising an oxidising agent.

* * * * *